(12) United States Patent
Li

(10) Patent No.: US 8,993,861 B2
(45) Date of Patent: Mar. 31, 2015

(54) SOYBEAN PROMOTERS SC194 AND FLOWER-PREFERRED EXPRESSION THEREOF IN TRANSGENIC PLANTS

(75) Inventor: Zhongsen Li, Hockessin (DE)

(73) Assignee: E I du Pont de Nemours and Company, Wilmington, DE (US)

( * ) Notice: Subject to any disclaimer, the term of this patent is extended or adjusted under 35 U.S.C. 154(b) by 1198 days.

(21) Appl. No.: 12/908,435

(22) Filed: Oct. 20, 2010

(65) Prior Publication Data

US 2011/0035842 A1 Feb. 10, 2011

Related U.S. Application Data

(63) Continuation of application No. 12/152,375, filed on May 14, 2008, now abandoned.

(60) Provisional application No. 60/930,877, filed on May 17, 2007.

(51) Int. Cl.
   *A01H 5/00* (2006.01)
   *A01H 5/10* (2006.01)
   *A01H 1/00* (2006.01)
   *C12N 15/82* (2006.01)

(52) U.S. Cl.
   CPC .......... *C12N 15/823* (2013.01); *C12N 15/8222* (2013.01)
   USPC ........ 800/323.2; 800/298; 800/278; 800/290; 536/24.1; 435/320.1; 435/410; 435/419

(58) Field of Classification Search
   None
   See application file for complete search history.

(56) References Cited

U.S. PATENT DOCUMENTS

| | | | |
|---|---|---|---|
| 4,945,050 | A | 7/1990 | Sanford et al. |
| 5,004,863 | A | 4/1991 | Umbeck |
| 5,107,065 | A | 4/1992 | Shewmaker et al. |
| 5,159,135 | A | 10/1992 | Umbeck |
| 5,231,020 | A | 7/1993 | Jorgensen et al. |
| 5,416,011 | A | 5/1995 | Hinchee et al. |
| 5,463,174 | A | 10/1995 | Moloney et al. |
| 5,569,834 | A | 10/1996 | Hinchee et al. |
| 6,072,050 | A | 6/2000 | Bowen et al. |

FOREIGN PATENT DOCUMENTS

| | | |
|---|---|---|
| WO | WO 9217598 A1 | 10/1992 |
| WO | WO 9836083 A1 | 8/1998 |
| WO | WO 9953050 A1 | 10/1999 |
| WO | WO 0037662 A2 | 6/2000 |
| WO | WO 0200904 A2 | 1/2002 |

OTHER PUBLICATIONS

Benfey et al (1990, Science 250:959-966).*
Benfey et al (1989, EMBO J, 8(8):2195-2202).*
Hsiang Chang et al., Overproduction of Cytokinins in Petunia Flowers Transformed with PSAG12-IPT Delays Corolla Senescence and Decreases Sensitivity to Ethylene, Plant Physiol., Aug. 2003 vol. 132, No. 4:2174-2183.
Odell et al., "Identification of DNA sequences required for activity of the cauliflower mosaic virus 35S promoter," Nature vol. 313. pp. 810-812 (1985).
P. R. Ebert et al., "Identification of an Essential upstream element in the nopaline synthase . . . ," Proc. Natl. Acad. Sci. U.S.A., vol. 84, pp. 5745-5749 (1987).
R. A. Jefferson et al., "GUS fusions: β-glucuronidase as a sensitive and versatile gene fusion marker in higher plants," EMBO J. vol. 6, No. 13, pp. 3901-3907 (1987).
Klein et al., "High-Velocity microprojectiles for delivering nucleic acids into living cells," Letter of Nature (London) vol. 327, pp. 70-73 (1987).
Lawton et al., "Expression of a soybean β-conclycinin gene under the control of the Cauliflower Mosiac Virus 35S and 198 . . . ," Plant Mol. Biol. 9:315-324 (1987).
J. C. Walker et al., "DNA sequences required for anaerobic expression of the maize alcohol dehydrogenase 1 gene," Proc. Natl. Acad. Sci, vol. 84, pp. 6624-6628 (1987).
Raschke et al., "Nucleotide Sequence Analysis of Soybean Small Heat Shock Protein Genes Belonging to two Different Multigene . . . ," J. Mol. Biol. 199(4), pp. 549-557 (1988).
V. L. Chandler et al., "Two Regulartory Genes of the Maize Anthocyanin Pathway Are Homologous: Isolation of B Utilizing R Genomic . . . ," Plant Cell, vol. 1, pp. 1175-1183 (1989).
J. K. Okamuro et al, "Regulation of plant gene expression: general principles," Biochemistry of Plants 15:1 82 (1989).
M. J. Battraw et al., "Histochemical analysis of CaMV 35S promoter-β-gluouronidase gene expression in transgenic rice plants," Plant Mal. Blot. 15:527-538 (1990).
J. Callis et al., "Ubiquitin Extension Proteins of *Arabidopsis thaliana*," J. Biol. Chem. 265(21):12486-12493 (1990).
Neuhaus et al., "Plants transformation by microinjection techniques," Physiol. Plant. 79:213-217 (1990).
M. Sanger et al., "Characteristics of a strong promoter from figwort mosaic virus: comparison with the analogous 35S promoter . . . ," Plant Mol. Biol. 14:433-443 (1990).
N. S. Yang et al., "Maize sucrose synthase-1 promoter directs phloem cell-specific expression of Gus gene . . . ," Proc. Natl. Acad. Sci. 87:4144-4148 (Jun. 1990).
Pelese-Siebenbourg et al., "A pair of genes coding for lipid-transfer proteins in *Sorghum vulgare*," Gene 148:305-308 (1994).
A. L. Plant et al., "Regulation of an *Arabidopsis oleosin* gene promoter in transgenic *Brassica napus*," Plant Mol. Biol. 25:193-205 (1994).
S. Thoma et al., Tissue-Specific Expression of a Gene Encoding a Cell Wall-Localized Lipid Transfer Protein from Arabidopsis, Plant Physiol. 105:35-45 (1994).
Vignols et al., "Characterization of a rice gene coding for a lipid transfer protein," Gene 142:265-270 (1994).
S. Holtorf et al., "Comparison of different constitutive and inducible promoters for the . . . *Arabidopsis thaliana*," Plant Mol. Biol. 29:637-646 (1995).

(Continued)

*Primary Examiner* — Stuart F Baum

(57) ABSTRACT

The promoters of a soybean SC194 polypeptide and fragments thereof and their use in promoting the expression of one or more heterologous nucleic acid fragments in plants are described.

16 Claims, 7 Drawing Sheets

(56) References Cited

OTHER PUBLICATIONS

Figure 1:
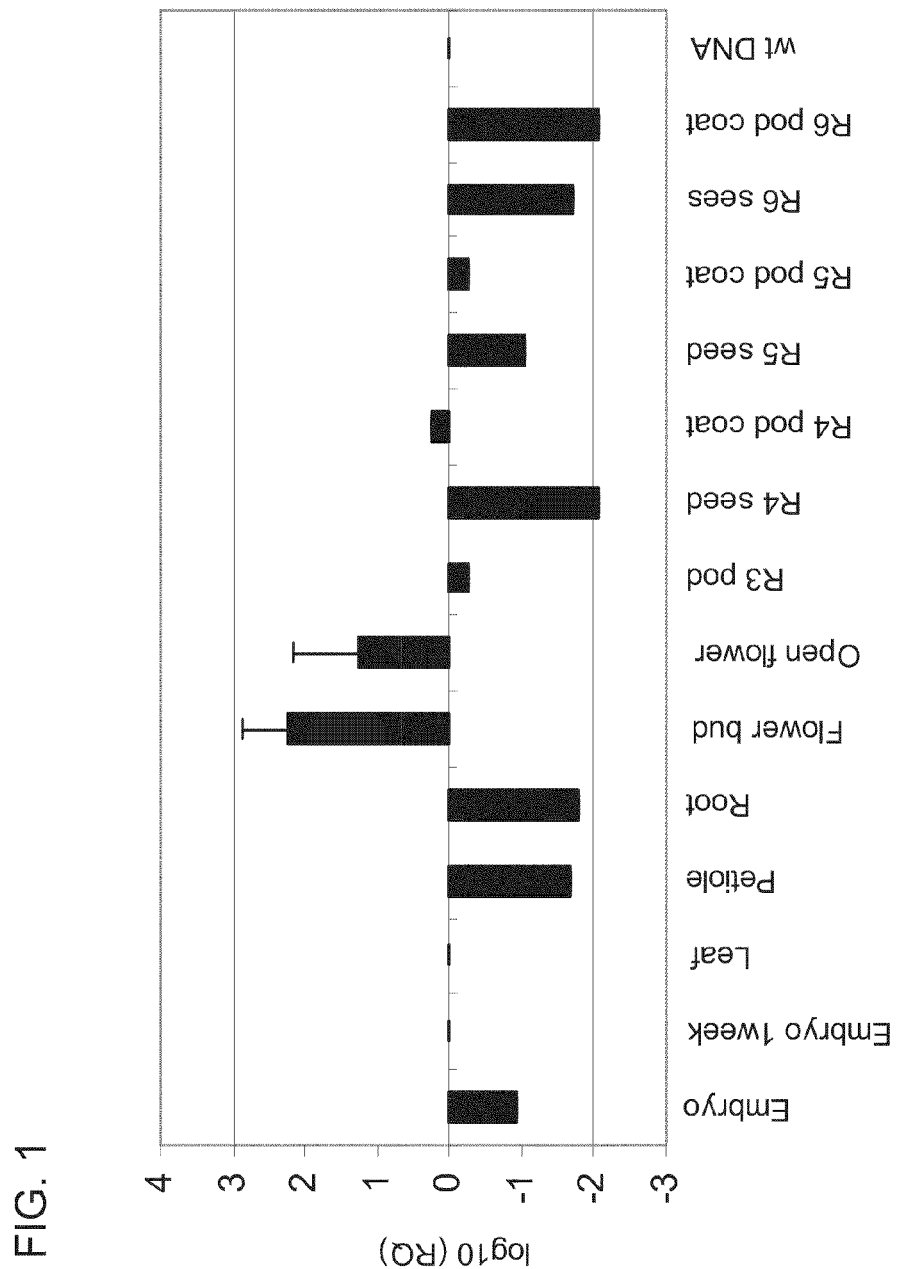

Pellegrineschi et al., "Expression of horseradish peroxidase in transgenic tobacco," Biochem. Soc. Trans. 23(2):247-250 (1995).
A. Wilmink et al., "Activity of constitutive promoters in various species from the Liliaceae," Plant Mol. Biol. 28:949-955 (1995).
Jean-Claude Kader, "Lipid-Transfer Proteins in Plants," Annu. Rev. Plant Physiol. Plant Mol. Biol. 47: 627-654 (1996).
Zhongsen Li, "Iolation and Characterization of *Arabidopsis*," Texas A&M Univ., May 1997.
M. A. J. Toonen et al., "AtLTP1 luciferase expression during carrot somatic embryogenesis," Plant Journal 12(5):1213-1221 (1997).
R. Atanassova et al., "Functional analysis of the promoter region of a maize (*Zea mays* L.) H3 histone gene in transgenic *Arabidopsis* . . .," Plant Mol. Biol. 37:275-285 (1998).
T. Elmayan et al., "*Arabidopsis* Mutants Impaired in Cosuppression," Plant Cell 10:1747-1757 (Oct. 1998).
Rollfinke et al., "Characterization and expression of a heptaubiquitin gene from tomato," Gene 211:267-276 (1998).
A. K. Sohal et al., "The promoter of a *Brassica napus* lipid transfer protein gene is active in a range of tissues . . . transgenic *Arabidopsis*," Plant Mol. Biol. 41:75-87 (1999).
I. Sabala et al., "Tissue-specific expression of Pa18, a putative lipid transfer protein gene, during embryo . . . (*Picea abies*)," Plant Mol. Biol. 42:461-478 (2000).
H. Chang et al., "Overproduction of Cytokinins in Petunia Flowers Transformed with PSAG12-IPT Delays Corolla . . . Sensitivity to Ethylene," Plant Physiol. 132:2174-2183 (8/03).
T. Kakimoto, "Biosynthesis of cytokinins," J. Plant Res. 116:233-239 (2003).
E. Yubero-Serrano et al, "Identification of a strawberry gene encoding a non-specific lipid transnfer protein that responds to ABA, . . .," J. Exp. Bot. 54:1865-1877 (2003).
C. Espinosa-Soto et al., "A Gene Regulatory Network Model for Cell-Fate Determination during *Arabidopsis* Gene Expression Profiles" Plant Cell 16:2923-2939 (Nov. 2004).
S. Mori et al., "Heterologous expression of the flavonoid 3,5,-hydroxylase gene of Vince major alters transgenic *Petunia hybrida*," Plant Cell Reports 22:415-421 (2004).
T. E. Young et al., "Senescence-induced expression of cytokinin reverses pistil abortion during maize flower development," Plant Journal, 38:910-922 (2004).
M. L. Federico et al., "The complex development expression of a novel stress-responsive barley Ltp gene is determined by a . . . sequence," Plant Mol. Biol. 57:35-51 (2005).
Y. Tanaka et al., "Genetic engineering in floriculture," Plant Cell, Tissue and Organ Culture 80:1-24 (2005).
Copending U.S. Appl. No. 12/080,113, filed Mar. 31, 2008.
Copending U.S. Appl. No. 12/152,369, filed May 14, 2008.

\* cited by examiner 1358 bp SC194 promoter

SEQUENCE LISTING

<160> NUMBER OF SEQ ID NOS: 53

<210> SEQ ID NO 1
<211> LENGTH: 1358
<212> TYPE: DNA
<213> ORGANISM: Glycine max

<400> SEQUENCE: 1

```
gggctggtaa cctagttaat aaattaaaag gagaacatta ttaatgtgaa aatcatgcaa      60
acttaaaaaa atcatcaaca acataatttt ataattctaa taaaatattt ttttctttta     120
attctttaat caatgtctaa catttatcta ttatttatca catttgttat ttaatgtttc     180
tatctttaga gctatcaaaa atttaaaatg gtggaacctt actcattggg ttgagttcac     240
ctaacttgtt taataaatag atcaatctaa ttctattcat ctcttagtaa gtattaaaaa     300
tgttggccca actctccata tattggtgag ttataggagt ttactcactt aaaatgataa     360
taaaaatatt tgttttaaaa tcatttttta aacaaaaaaa taatgtttca gattatttat     420
tcttagatca taacttacaa gcaacatttc aatgatcaat tcaattgtca gaatcaaaac     480
caattgaaag agacaaatat tcatgctaat cttcatcaga aactaaacat tgacataaag     540
```

```
caatagtatt ggaactacaa gttataatta tgtactttgt aatagtgtga agaaaatcaa    600
aatacaaata gtaatcatca tgataaatgc tatctcaatt tattcaatta taaaaatata    660
gaaataaaat gtgataaatg gataacatgt gtgctaatcc agtccactac gcccaccaca    720
agttcaaccc aatggactgg atcatcttct ttttttctta ctgatttctc tcttcttcca    780
ttctaatcca tcccaaaagt agatgtttac tatttcccct ttcatagttt cacaagtgtg    840
cgcagaggcc aaactgaaag tggtagtaca tggtgtaata ttaatcacag atgtgctctc    900
atgaagtctg aacttacagc tcaagtaaca accaacaagt aaaaagtaca agagatagca    960
taaaaaatga aggtagaaca aattccaagt tttctacata ttacggtgca taaatcaacc   1020
acgtgaaggc tccatttatt tgccgctata acattggtga ccctcttcca caatagtaa    1080 gtaataaaac caagtacaaa aaaatgttca actaccaagt gatcacaatc ttcatgcatc   1140
tgagtcacac tattgcccct tgctcatgaa gtacacttta ctcaccgcca agttcactc    1200 aacactgtag aacaaaggaa tcatataaat aatgcatatc tctcccttaa gccttcaaca   1260
catacaaaag tgacacacca aatcaaagac acctgagcca ttcaattccc ctcctttatt   1320
gctttcaagt ttcaacacta attttattat ctgaaacc                           1358

<210> SEQ ID NO 2
<211> LENGTH: 1328
<212> TYPE: DNA
<213> ORGANISM: Glycine max

<400> SEQUENCE: 2
ggagaacatt attaatgtga aaatcatgca aacttaaaaa aatcatcaac aacataattt     60
tataattcta ataaaatatt ttttttctttt aattctttaa tcaatgtcta acatttatct    120
attatttatc acatttgtta tttaatgttt ctatctttag agctatcaaa aatttaaaat    180
ggtggaacct tactcattgg gttgagttca cctaacttgt ttaataaata gatcaatcta    240
attctattca tctcttagta agtattaaaa atgttggccc aactctccat atattggtga    300
gttataggag tttactcact taaaatgata ataaaaatat ttgttttaaa atcattttt     360 aaacaaaaaa ataatgtttc agattatttta ttcttagatc ataacttaca agcaacattt    420
caatgatcaa ttcaattgtc agaatcaaaa ccaattgaaa gagacaaata ttcatgctaa    480
tcttcatcag aaactaaaca ttgacataaa gcaatagtat tggaactaca agttataatt    540
atgtactttg taatagtgtg aagaaaatca aaatacaaat agtaatcatc atgataaatg    600
ctatctcaat ttattcaatt ataaaaatat agaaataaaa tgtgataaat ggataacatg    660
tgtgctaatc cagtccacta cgcccaccac aagttcaacc caatggactg gatcatcttc    720 ttttttttctt actgatttct ctcttcttcc attctaatcc atcccaaaag tagatgttta    780
ctatttcccc tttcatagtt tcacaagtgt gcgcagaggc caaactgaaa gtggtagtac    840
atggtgtaat attaatcaca gatgtgctct catgaagtct gaacttacag ctcaagtaac    900
aaccaacaag taaaaagtac agaagatagc ataaaaaatg aaggtagaac aaattccaag    960
ttttctacat attacggtgc ataaatcaac cacgtgaagg ctccatttat ttgccgctat   1020
aacattggtg accctcttcc acaaatagta agtaataaaa ccaagtacaa aaaatgttc     1080 aactaccaag tgatcacaat cttcatgcat ctgagtcaca ctattgccct tgctcatga    1140 agtacacttt actcaccgcc aaagttcact caacactgta gaacaaagga atcatataaa   1200
taatgcatat ctctccctta agccttcaac acatacaaaa gtgacacacc aaatcaaaga   1260
```

```
cacctgagcc attcaattcc cctcctttat tgctttcaag tttcaacact aattttatta    1320
tctgaaac                                                              1328

<210> SEQ ID NO 3
<211> LENGTH: 1134
<212> TYPE: DNA
<213> ORGANISM: Glycine max

<400> SEQUENCE: 3
cattgggttg agttcaccta acttgtttaa taaatagatc aatctaattc tattcatctc      60
ttagtaagta ttaaaaatgt tggcccaact ctccatatat tggtgagtta taggagttta    120
ctcacttaaa atgataataa aaatatttgt tttaaaatca tttttttaaac aaaaaaataa    180 tgtttcagat tatttattct tagatcataa cttacaagca acatttcaat gatcaattca    240
attgtcagaa tcaaaaccaa ttgaaagaga caaatattca tgctaatctt catcagaaac    300
taaacattga cataaagcaa tagtattgga actacaagtt ataattatgt actttgtaat    360
agtgtgaaga aaatcaaaat acaaatagta atcatcatga taaatgctat ctcaatttat    420
tcaattataa aaatatagaa ataaaatgtg taaatggat aacatgtgtg ctaatccagt     480
ccactacgcc caccacaagt tcaacccaat ggactggatc atcttctttt tttcttactg    540
atttctctct tcttccattc taatccatcc caaaagtaga tgtttactat ttcccctttc    600
atagtttcac aagtgtgcgc agaggccaaa ctgaaagtgg tagtacatgg tgtaatatta    660
atcacagatg tgctctcatg aagtctgaac ttacagctca agtaacaacc aacaagtaaa    720
aagtacagaa gatagcataa aaaatgaagg tagaacaaat tccaagtttt ctacatatta    780
cggtgcataa atcaaccacg tgaaggctcc atttatttgc cgctataaca ttggtgaccc    840
tcttccacaa atagtaagta ataaaaccaa gtacaaaaaa atgttcaact accaagtgat    900
cacaatcttc atgcatctga gtcacactat tgcccttttgc tcatgaagta cactttactc    960
accgccaaag ttcactcaac actgtagaac aaaggaatca tataataat gcatatctct    1020 cccttaagcc ttcaacacat acaaaagtga cacaccaaat caaagacacc tgagccattc   1080
aattcccctc ctttattgct ttcaagtttc aacactaatt ttattatctg aaac          1134

<210> SEQ ID NO 4
<211> LENGTH: 932
<212> TYPE: DNA
<213> ORGANISM: Glycine max

<400> SEQUENCE: 4
gatcataact tacaagcaac atttcaatga tcaattcaat tgtcagaatc aaaaccaatt      60
gaaagagaca atattcatg ctaatcttca tcagaaacta acattgaca taaagcaata     120 gtattggaac tacaagttat aattatgtac tttgtaatag tgtgaagaaa atcaaaatac    180
aaatagtaat catcatgata aatgctatct caatttattc aattataaaa atatagaaat    240
aaaatgtgat aaatggataa catgtgtgct aatccagtcc actacgccca ccacaagttc    300
aacccaatgg actggatcat cttctttttt tcttactgat ttctctcttc ttccattcta    360
atccatccca aaagtagatg tttactattt cccctttcat agtttcacaa gtgtgcgcag    420
aggccaaact gaaagtggta gtacatggtg taatattaat cacagatgtg ctctcatgaa    480
gtctgaactt acagctcaag taacaaccaa caagtaaaaa gtacagaaga tagcataaaa    540
aatgaaggta gaacaaattc caagttttct acatattacg gtgcataaat caaccacgtg    600
aaggctccat ttatttgccg ctataacatt ggtgaccctc ttccacaaat agtaagtaat    660
```

```
aaaaccaagt acaaaaaaat gttcaactac caagtgatca caatcttcat gcatctgagt    720
cacactattg cccttttgctc atgaagtaca ctttactcac cgccaaagtt cactcaacac    780
tgtagaacaa aggaatcata taaataatgc atatctctcc cttaagcctt caacacatac    840
aaaagtgaca caccaaatca agacacctg agccattcaa ttcccctcct ttattgcttt    900
caagtttcaa cactaatttt attatctgaa ac                                  932
```

```
<210> SEQ ID NO 5
<211> LENGTH: 685
<212> TYPE: DNA
<213> ORGANISM: Glycine max

<400> SEQUENCE: 5
gataaatgga taacatgtgt gctaatccag tccactacgc ccaccacaag ttcaacccaa     60
tggactggat catcttcttt ttttcttact gatttctctc ttcttccatt ctaatccatc    120
ccaaaagtag atgtttacta tttcccctttt catagtttca caagtgtgcg cagaggccaa   180
actgaaagtg gtagtacatg gtgtaatatt aatcacagat gtgctctcat gaagtctgaa    240
cttacagctc aagtaacaac caacaagtaa aaagtacaga agatagcata aaaaatgaag    300
gtagaacaaa ttccaagttt tctacatatt acggtgcata aatcaaccac gtgaaggctc    360 catttattg ccgctataac attggtgacc ctcttccaca aatagtaagt aataaaacca     420
agtacaaaaa aatgttcaac taccaagtga tcacaatctt catgcatctg agtcacacta    480
ttgccccttg ctcatgaagt acactttact caccgccaaa gttcactcaa cactgtagaa    540
caaaggaatc atataaataa tgcatatctc tcccttaagc cttcaacaca tacaaaagtg    600
acacaccaaa tcaaagacac ctgagccatt caattcccct cctttattgc tttcaagttt    660
caacactaat tttattatct gaaac                                          685
```

```
<210> SEQ ID NO 6
<211> LENGTH: 472
<212> TYPE: DNA
<213> ORGANISM: Glycine max

<400> SEQUENCE: 6
cacagatgtg ctctcatgaa gtctgaactt acagctcaag taacaaccaa caagtaaaaa     60
gtacagaaga tagcataaaa aatgaaggta gaacaaattc caagttttct acatattacg    120
gtgcataaat caaccacgtg aaggctccat ttatttgccg ctataacatt ggtgaccctc    180
ttccacaaat agtaagtaat aaaaccaagt acaaaaaaat gttcaactac caagtgatca    240
caatcttcat gcatctgagt cacactattg ccctttgctc atgaagtaca ctttactcac    300
cgccaaagtt cactcaacac tgtagaacaa aggaatcata taaataatgc atatctctcc    360
cttaagcctt caacacatac aaaagtgaca caccaaatca agacacctg agccattcaa     420 ttcccctcct ttattgcttt caagtttcaa cactaatttt attatctgaa ac            472
```

```
<210> SEQ ID NO 7
<211> LENGTH: 237
<212> TYPE: DNA
<213> ORGANISM: Glycine max

<400> SEQUENCE: 7
gatcacaatc ttcatgcatc tgagtcacac tattgcccctt tgctcatgaa gtacacttta     60
ctcaccgcca aagttcactc aacactgtag aacaaaggaa tcatataaat aatgcatatc    120
```

```
tctcccttaa gccttcaaca catacaaaag tgacacacca aatcaaagac acctgagcca    180
ttcaattccc ctcctttatt gctttcaagt ttcaacacta attttattat ctgaaac      237
```

<210> SEQ ID NO 8
<211> LENGTH: 32
<212> TYPE: DNA
<213> ORGANISM: Artificial
<220> FEATURE:
<223> OTHER INFORMATION: Primer

<400> SEQUENCE: 8

```
gtttcagata ataaaattag tgttgaaact tg                                   32
```

<210> SEQ ID NO 9
<211> LENGTH: 29
<212> TYPE: DNA
<213> ORGANISM: Artificial
<220> FEATURE:
<223> OTHER INFORMATION: Primer

<400> SEQUENCE: 9

```
ggagaacatt attaatgtga aaatcatgc                                       29
```

<210> SEQ ID NO 10
<211> LENGTH: 25
<212> TYPE: DNA
<213> ORGANISM: Artificial
<220> FEATURE:
<223> OTHER INFORMATION: Primer

<400> SEQUENCE: 10

```
cattgggttg agttcaccta acttg                                           25
```

<210> SEQ ID NO 11
<211> LENGTH: 29
<212> TYPE: DNA
<213> ORGANISM: Artificial
<220> FEATURE:
<223> OTHER INFORMATION: Primer

<400> SEQUENCE: 11

```
gatcataact tacaagcaac atttcaatg                                       29
```

<210> SEQ ID NO 12
<211> LENGTH: 28
<212> TYPE: DNA
<213> ORGANISM: Artificial
<220> FEATURE:
<223> OTHER INFORMATION: Primer

<400> SEQUENCE: 12

```
gataaatgga taacatgtgt gctaatcc                                        28
```

<210> SEQ ID NO 13
<211> LENGTH: 25
<212> TYPE: DNA
<213> ORGANISM: Artificial
<220> FEATURE:
<223> OTHER INFORMATION: Primer

<400> SEQUENCE: 13

```
cacagatgtg ctctcatgaa gtctg                                           25
```

<210> SEQ ID NO 14
<211> LENGTH: 26

```
<212> TYPE: DNA
<213> ORGANISM: Artificial
<220> FEATURE:
<223> OTHER INFORMATION: Primer

<400> SEQUENCE: 14
gatcacaatc ttcatgcatc tgagtc                                          26

<210> SEQ ID NO 15
<211> LENGTH: 26
<212> TYPE: DNA
<213> ORGANISM: Artificial
<220> FEATURE:
<223> OTHER INFORMATION: Primer

<400> SEQUENCE: 15
caaggaaaaa cgaaactttg aaagcc                                          26

<210> SEQ ID NO 16
<211> LENGTH: 25
<212> TYPE: DNA
<213> ORGANISM: Artificial
<220> FEATURE:
<223> OTHER INFORMATION: Primer

<400> SEQUENCE: 16
gtaatacgac tcactatagg gcacg                                           25

<210> SEQ ID NO 17
<211> LENGTH: 37
<212> TYPE: DNA
<213> ORGANISM: Artificial
<220> FEATURE:
<223> OTHER INFORMATION: Primer

<400> SEQUENCE: 17
ccatggtttc agataataaa attagtgttg aaacttg                              37

<210> SEQ ID NO 18
<211> LENGTH: 22
<212> TYPE: DNA
<213> ORGANISM: Artificial
<220> FEATURE:
<223> OTHER INFORMATION: Primer

<400> SEQUENCE: 18
ctatagggca cgcgtggtcg ac                                              22

<210> SEQ ID NO 19
<211> LENGTH: 832
<212> TYPE: DNA
<213> ORGANISM: Glycine max

<400> SEQUENCE: 19
acacaccaaa tcaaagacac ctgagccatt caattcccct cctttattgc tttcaagttt      60
caacactaat tttattatct gaaaaaatgg ctttcaaagt ttcgtttttc cttgcacttg     120
ttctagtttc caatatcctc ctccttgata caacagctgc tggacgcagc attggcgaaa     180
actccaactc agaggaaaag aaagagcctg agttcttgtt caagcatgaa ggtgggtgt      240 atattccagg gattggacct gttggatttc cacataaatt tcatctcaca cctcaaaatc     300
cattacctgg tggcaatgga aatggaggag caggaaccgc aacaggatca ggatcaccac     360
caggtagcag ttatgttcct ggtggtgatg acactttgt cccaaaccct ggttatgagg     420
```

```
ttcccattcc cggcagtggt ggaagtgttc cagcaccagc tgcaccatga gttaactcat    480
gcatgattaa tgtgatgcat ggtagttaat aaggtggtta tgcttaagtt tgtcttttc     540 tttctgtttt ctagccataa taataactta tcataaataa gtatgctcca tgtgcacatt    600
ggtgtatatg gtgaacacca tggattgcca agtcattctg tttgttcttg tagtcttgtt    660
ttaagatgaa ttgagtgtga cgtaagctta tttgttttc gaagtaaaaa ctgatgaatg     720
agtcctcaaa ataatttct gttatgattc caatttgata ttctcttttc atgcacagtt     780
ttatgtgttt ggtccttgaa tgataaaaaa aaaaaaaaa aaaaaaaaa aa              832
```

<210> SEQ ID NO 20
<211> LENGTH: 127
<212> TYPE: PRT
<213> ORGANISM: Glycine max

<400> SEQUENCE: 20

```
Met Ala Phe Lys Val Ser Phe Phe Leu Ala Leu Val Leu Val Ser Asn
1               5                   10                  15

Ile Leu Leu Leu Asp Thr Thr Ala Ala Gly Arg Ser Ile Glu Asn
            20                  25                  30

Ser Asn Ser Glu Glu Lys Lys Glu Pro Glu Phe Leu Phe Lys His Glu
        35                  40                  45

Gly Gly Val Tyr Ile Pro Gly Ile Gly Pro Val Gly Phe Pro His Lys
    50                  55                  60

Phe His Leu Thr Pro Gln Asn Pro Leu Pro Gly Asn Gly Asn Gly
65                  70                  75                  80

Gly Ala Gly Thr Ala Thr Gly Ser Gly Ser Pro Pro Gly Ser Ser Tyr
                85                  90                  95

Val Pro Gly Gly Asp Asp Thr Phe Val Pro Asn Pro Gly Tyr Glu Val
            100                 105                 110

Pro Ile Pro Gly Ser Gly Gly Ser Val Pro Ala Pro Ala Ala Pro
        115                 120                 125
```

<210> SEQ ID NO 21
<211> LENGTH: 26
<212> TYPE: DNA
<213> ORGANISM: Artificial
<220> FEATURE:
<223> OTHER INFORMATION: Primer

<400> SEQUENCE: 21

```
gaccaagaca cactcgttca tatatc                                         26
```

<210> SEQ ID NO 22
<211> LENGTH: 25
<212> TYPE: DNA
<213> ORGANISM: Artificial
<220> FEATURE:
<223> OTHER INFORMATION: Primer

<400> SEQUENCE: 22

```
tctgctgctc aatgtttaca aggac                                          25
```

<210> SEQ ID NO 23
<211> LENGTH: 48
<212> TYPE: DNA
<213> ORGANISM: Artificial
<220> FEATURE:
<223> OTHER INFORMATION: Longer strand sequence of the adaptor supplied
      in GenomeWalker(tm) kit

```
<400> SEQUENCE: 23
gtaatacgac tcactatagg gcacgcgtgg tcgacggccc gggctggt        48

<210> SEQ ID NO 24
<211> LENGTH: 17
<212> TYPE: DNA
<213> ORGANISM: Artificial
<220> FEATURE:
<223> OTHER INFORMATION: MPSS tag sequence

<400> SEQUENCE: 24
gatcaccacc aggtagc                                          17

<210> SEQ ID NO 25
<211> LENGTH: 20
<212> TYPE: DNA
<213> ORGANISM: Artificial
<220> FEATURE:
<223> OTHER INFORMATION: Primer

<400> SEQUENCE: 25
aaccgcaaca ggatcaggat                                       20

<210> SEQ ID NO 26
<211> LENGTH: 21
<212> TYPE: DNA
<213> ORGANISM: Artificial
<220> FEATURE:
<223> OTHER INFORMATION: Primer

<400> SEQUENCE: 26
accagggttt gggacaaaag t                                     21

<210> SEQ ID NO 27
<211> LENGTH: 24
<212> TYPE: DNA
<213> ORGANISM: Artificial
<220> FEATURE:
<223> OTHER INFORMATION: Primer

<400> SEQUENCE: 27
catgattggg agaaacctta agct                                  24

<210> SEQ ID NO 28
<211> LENGTH: 20
<212> TYPE: DNA
<213> ORGANISM: Artificial
<220> FEATURE:
<223> OTHER INFORMATION: Primer

<400> SEQUENCE: 28
agattgggcc agaggatcct                                       20

<210> SEQ ID NO 29
<211> LENGTH: 22
<212> TYPE: DNA
<213> ORGANISM: Artificial
<220> FEATURE:
<223> OTHER INFORMATION: Primer

<400> SEQUENCE: 29
ggaagaagag aatcgggtgg tt                                    22

<210> SEQ ID NO 30
<211> LENGTH: 23
```

```
<212> TYPE: DNA
<213> ORGANISM: Artificial
<220> FEATURE:
<223> OTHER INFORMATION: FAM labeled fluorescent DNA oligo probe

<400> SEQUENCE: 30
attgtgttgt gtggcatggt tat                                          23

<210> SEQ ID NO 31
<211> LENGTH: 23
<212> TYPE: DNA
<213> ORGANISM: Artificial
<220> FEATURE:
<223> OTHER INFORMATION: Primer

<400> SEQUENCE: 31
ggcttgttgt gcagtttttg aag                                          23

<210> SEQ ID NO 32
<211> LENGTH: 20
<212> TYPE: DNA
<213> ORGANISM: Artificial
<220> FEATURE:
<223> OTHER INFORMATION: Primer

<400> SEQUENCE: 32
aacggccaca agttcgtgat                                              20

<210> SEQ ID NO 33
<211> LENGTH: 20
<212> TYPE: DNA
<213> ORGANISM: Artificial
<220> FEATURE:
<223> OTHER INFORMATION: FAM labeled fluorescent DNA oligo probe

<400> SEQUENCE: 33
accggcgagg gcatcggcta                                              20

<210> SEQ ID NO 34
<211> LENGTH: 20
<212> TYPE: DNA
<213> ORGANISM: Artificial
<220> FEATURE:
<223> OTHER INFORMATION: Primer

<400> SEQUENCE: 34
cttcaagggc aagcagacca                                              20

<210> SEQ ID NO 35
<211> LENGTH: 24
<212> TYPE: DNA
<213> ORGANISM: Artificial
<220> FEATURE:
<223> OTHER INFORMATION: Primer

<400> SEQUENCE: 35
caaacttgac aaagccacaa ctct                                         24

<210> SEQ ID NO 36
<211> LENGTH: 20
<212> TYPE: DNA
<213> ORGANISM: Artificial
<220> FEATURE:
<223> OTHER INFORMATION: VIC labeled DNA oligo probe

<400> SEQUENCE: 36
```

```
ctctcatctc atataaatac                                              20

<210> SEQ ID NO 37
<211> LENGTH: 21
<212> TYPE: DNA
<213> ORGANISM: Artificial
<220> FEATURE:
<223> OTHER INFORMATION: Primer

<400> SEQUENCE: 37
ggagaaattg gtgtcgtgga a                                            21

<210> SEQ ID NO 38
<211> LENGTH: 21
<212> TYPE: DNA
<213> ORGANISM: Artificial
<220> FEATURE:
<223> OTHER INFORMATION: Recombination site attB1 sequence

<400> SEQUENCE: 38
caagtttgta caaaaaagca g                                            21

<210> SEQ ID NO 39
<211> LENGTH: 21
<212> TYPE: DNA
<213> ORGANISM: Artificial
<220> FEATURE:
<223> OTHER INFORMATION: Recombination site attB2 sequence

<400> SEQUENCE: 39
cagctttctt gtacaaagtg g                                            21

<210> SEQ ID NO 40
<211> LENGTH: 3291
<212> TYPE: DNA
<213> ORGANISM: Artificial
<220> FEATURE:
<223> OTHER INFORMATION: Nucleotide sequence of QC299

<400> SEQUENCE: 40
tcgacccggg atccatggcc cacagcaagc acggcctgaa ggaggagatg accatgaagt    60
accacatgga gggctgcgtg aacggccaca gttcgtgat caccggcgag ggcatcggct    120
accccttcaa gggcaagcag accatcaacc tgtgcgtgat cgagggcggc cccctgccct    180
tcagcgagga catcctgagc gccggcttca gtacggcga ccggatcttc accgagtacc    240
cccaggacat cgtggactac ttcaagaaca gctgccccgc cggctacacc tggggccgga    300
gcttcctgtt cgaggacggc gccgtgtgca tctgtaacgt ggacatcacc gtgagcgtga    360
aggagaactg catctaccac aagagcatct caacggcgt gaacttcccc gccgacggcc    420
ccgtgatgaa gaagatgacc accaactggg aggccagctg cgagaagatc atgcccgtgc    480
ctaagcaggg catcctgaag ggcgacgtga gcatgtacct gctgctgaag gacggcggcc    540
ggtaccggtg ccagttcgac accgtgtaca aggccaagag cgtgcccagc aagatgcccg    600
agtggcactt catccagcac aagctgctgc gggaggaccg gagcgacgcc aagaaccaga    660
agtggcagct gaccgagcac gccatcgcct tccccagcgc cctggcctga gagctcgaat    720
ttccccgatc gttcaaacat ttggcaataa agtttcttaa gattgaatcc tgttgccggt    780
cttgcgatga ttatcatata atttctgttg aattacgtta agcatgtaat aattaacatg    840
taatgcatga cgttatttat gagatggggt tttatgatta gagtcccgca attatacatt    900
taatacgcga tagaaaacaa aatatagcgc gcaaactagg ataaattatc gcgcgcggtg    960
```

```
tcatctatgt tactagatcg ggaattctag tggccggccc agctgatatc catcacactg    1020
gcggccgcac tcgagatatc tagacccagc tttcttgtac aaagttggca ttataagaaa    1080
gcattgctta tcaatttgtt gcaacgaaca ggtcactatc agtcaaaata aaatcattat    1140
ttgccatcca gctgcagctc tggcccgtgt ctcaaaatct ctgatgttac attgcacaag    1200
ataaaaatat atcatcatga acaataaaac tgtctgctta cataaacagt aatacaaggg    1260
gtgttatgag ccatattcaa cgggaaacgt cgaggccgcg attaaattcc aacatggatg    1320
ctgatttata tgggtataaa tgggctcgcg ataatgtcgg gcaatcaggt gcgacaatct    1380
atcgcttgta tgggaagccc gatgcgccag agttgtttct gaaacatggc aaaggtagcg    1440
ttgccaatga tgttacagat gagatggtca gactaaactg gctgacggaa tttatgcctc    1500
ttccgaccat caagcatttt atccgtactc ctgatgatgc atggttactc accactgcga    1560
tccccggaaa aacagcattc caggtattag aagaatatcc tgattcaggt gaaaatattg    1620
ttgatgcgct ggcagtgttc ctgcgccggt tgcattcgat tcctgtttgt aattgtcctt    1680
ttaacagcga tcgcgtattt cgtctcgctc aggcgcaatc acgaatgaat aacggtttgg    1740
ttgatgcgag tgattttgat gacgagcgta atggctggcc tgttgaacaa gtctggaaag    1800
aaatgcataa acttttgcca ttctcaccgg attcagtcgt cactcatggt gatttctcac    1860
ttgataacct tatttttgac gaggggaaat taataggttg tattgatgtt ggacgagtcg    1920
gaatcgcaga ccgataccag gatcttgcca tcctatggaa ctgcctcggt gagttttctc    1980
cttcattaca gaaacggctt tttcaaaaat atggtattga taatcctgat atgaataaat    2040
tgcagtttca tttgatgctc gatgagtttt tctaatcaga attggttaat ggttgtaac    2100 attattcaga ttgggccccg ttccactgag cgtcagaccc cgtagaaaag atcaaaggat    2160
cttcttgaga tcctttttt ctgcgcgtaa tctgctgctt gcaaacaaaa aaaccaccgc    2220
taccagcggt ggtttgtttg ccggatcaag agctaccaac tctttttccg aaggtaactg    2280
gcttcagcag agcgcagata ccaaatactg ttcttctagt gtagccgtag ttaggccacc    2340
acttcaagaa ctctgtagca ccgcctacat acctcgctct gctaatcctg ttaccagtgg    2400
ctgctgccag tggcgataag tcgtgtctta ccgggttgga ctcaagacga tagttaccgg    2460
ataaggcgca gcggtcgggc tgaacggggg gttcgtgcac acagcccagc ttggagcgaa    2520
cgacctacac cgaactgaga tacctacagc gtgagctatg agaaagcgcc acgcttcccg    2580
aagggagaaa ggcggacagg tatccggtaa gcggcagggt cggaacagga gagcgcacga    2640
gggagcttcc agggggaaac gcctggtatc tttatagtcc tgtcgggttt cgccacctct    2700
gacttgagcg tcgatttttg tgatgctcgt caggggggcg gagcctatgg aaaaacgcca    2760
gcaacgcggc ctttttacgg ttcctggcct tttgctggcc ttttgctcac atgttctttc    2820
ctgcgttatc ccctgattct gtggataacc gtattaccgc tagcatggat ctcggggacg    2880
tctaactact aagcgagagt agggaactgc caggcatcaa ataaaacgaa aggctcagtc    2940
ggaagactgg gcctttcgtt ttatctgttg tttgtcggtg aacgctctcc tgagtaggac    3000
aaatccgccg ggagcggatt tgaacgttgt gaagcaacgg cccggagggt ggcgggcagg    3060
acgcccgcca taaactgcca ggcatcaaac taagcagaag gccatcctga cggatggcct    3120
ttttgcgttt ctacaaactc ttcctgttag ttagttactt aagctcgggc cccaaataat    3180
gattttattt tgactgatag tgacctgttc gttgcaacaa attgataagc aatgcttttt    3240
tataatgcca actttgtaca aaaaagcagg ctggcgccgg aaccaattca g             3291
```

<210> SEQ ID NO 41
<211> LENGTH: 4642
<212> TYPE: DNA
<213> ORGANISM: Artificial
<220> FEATURE:
<223> OTHER INFORMATION: Nucleotide sequence of QC300

<400> SEQUENCE: 41

| | | | | | |
|---|---|---|---|---|---|
| catggcccac | agcaagcacg | gcctgaagga | ggagatgacc | atgaagtacc | acatggaggg | 60 |
| ctgcgtgaac | ggccacaagt | tcgtgatcac | cggcgagggc | atcggctacc | ccttcaaggg | 120 |
| caagcagacc | atcaacctgt | gcgtgatcga | gggcggcccc | ctgcccttca | gcgaggacat | 180 |
| cctgagcgcc | ggcttcaagt | acggcgaccg | gatcttcacc | gagtaccccc | aggacatcgt | 240 |
| ggactacttc | aagaacagct | gccccgccgg | ctacacctgg | ggccggagct | tcctgttcga | 300 |
| ggacggcgcc | gtgtgcatct | gtaacgtgga | catcaccgtg | agcgtgaagg | agaactgcat | 360 |
| ctaccacaag | agcatcttca | acggcgtgaa | cttccccgcc | gacggccccg | tgatgaagaa | 420 |
| gatgaccacc | aactgggagg | ccagctgcga | gaagatcatg | cccgtgccta | gcagggcat | 480 |
| cctgaagggc | gacgtgagca | tgtacctgct | gctgaaggac | ggcggccggt | accggtgcca | 540 |
| gttcgacacc | gtgtacaagg | ccaagagcgt | gcccagcaag | atgcccgagt | ggcacttcat | 600 |
| ccagcacaag | ctgctgcggg | aggaccggag | cgacgccaag | aaccagaagt | ggcagctgac | 660 |
| cgagcacgcc | atcgccttcc | ccagcgccct | ggcctgagag | ctcgaatttc | cccgatcgtt | 720 |
| caaacatttg | gcaataaagt | ttcttaagat | tgaatcctgt | tgccggtctt | gcgatgatta | 780 |
| tcatataatt | tctgttgaat | tacgttaagc | atgtaataat | taacatgtaa | tgcatgacgt | 840 |
| tatttatgag | atgggttttt | atgattagag | tcccgcaatt | atacatttaa | tacgcgatag | 900 |
| aaaacaaaat | atagcgcgca | aactaggata | aattatcgcg | cgcggtgtca | tctatgttac | 960 |
| tagatcggga | attctagtgg | ccggcccagc | tgatatccat | cacactggcg | gccgcactcg | 1020 |
| agatatctag | acccagcttt | cttgtacaaa | gttggcatta | taagaaagca | ttgcttatca | 1080 |
| atttgttgca | acgaacaggt | cactatcagt | caaaataaaa | tcattatttg | ccatccagct | 1140 |
| gcagctctgg | cccgtgtctc | aaaatctctg | atgttacatt | gcacaagata | aaaatatatc | 1200 |
| atcatgaaca | ataaaactgt | ctgcttacat | aaacagtaat | acaaggggtg | ttatgagcca | 1260 |
| tattcaacgg | gaaacgtcga | ggccgcgatt | aaattccaac | atggatgctg | atttatatgg | 1320 |
| gtataaatgg | gctcgcgata | atgtcgggca | atcaggtgcg | acaatctatc | gcttgtatgg | 1380 |
| gaagcccgat | gcgccagagt | tgtttctgaa | acatggcaaa | ggtagcgttg | ccaatgatgt | 1440 |
| tacagatgag | atggtcagac | taaactggct | gacggaattt | atgcctcttc | cgaccatcaa | 1500 |
| gcatttatc | cgtactcctg | atgatgcatg | gttactcacc | actgcgatcc | ccggaaaaac | 1560 |
| agcattccag | gtattagaag | aatatcctga | ttcaggtgaa | aatattgttg | atgcgctggc | 1620 |
| agtgttcctg | cgccggttgc | attcgattcc | tgtttgtaat | tgtccttttta | acagcgatcg | 1680 |
| cgtatttcgt | ctcgctcagg | cgcaatcacg | aatgaataac | ggtttggttg | atgcgagtga | 1740 |
| ttttgatgac | gagcgtaatg | gctggcctgt | tgaacaagtc | tggaaagaaa | tgcataaact | 1800 |
| tttgccattc | tcaccggatt | cagtcgtcac | tcatggtgat | ttctcacttg | ataaccttat | 1860 |
| ttttgacgag | gggaaattaa | taggttgtat | tgatgttgga | cgagtcggaa | tcgcagaccg | 1920 |
| ataccaggat | cttgccatcc | tatggaactg | cctcggtgag | ttttctcctt | cattacagaa | 1980 |
| acggcttttt | caaaaatatg | gtattgataa | tcctgatatg | aataaattgc | agtttcatttt | 2040 |
| gatgctcgat | gagttttttct | aatcagaatt | ggttaattgg | ttgtaacatt | attcagattg | 2100 |

-continued

```
ggccccgttc cactgagcgt cagacccgt agaaaagatc aaaggatctt cttgagatcc   2160
ttttttctg cgcgtaatct gctgcttgca acaaaaaaa ccaccgctac cagcggtggt   2220
ttgtttgccg gatcaagagc taccaactct ttttccgaag gtaactggct tcagcagagc   2280
gcagatacca aatactgttc ttctagtgta gccgtagtta ggccaccact tcaagaactc   2340
tgtagcaccg cctacatacc tcgctctgct aatcctgtta ccagtggctg ctgccagtgg   2400
cgataagtcg tgtcttaccg ggttggactc aagacgatag ttaccggata aggcgcagcg   2460
gtcgggctga acggggggtt cgtgcacaca gcccagcttg gagcgaacga cctacaccga   2520
actgagatac ctacagcgtg agctatgaga aagcgccacg cttcccgaag ggagaaaggc   2580
ggacaggtat ccggtaagcg gcagggtcgg aacaggagag cgcacgaggg agcttccagg   2640
gggaaacgcc tggtatcttt atagtcctgt cgggtttcgc cacctctgac ttgagcgtcg   2700
atttttgtga tgctcgtcag gggggcggag cctatggaaa aacgccagca acgcggcctt   2760
tttacggttc ctggcctttt gctggccttt tgctcacatg ttctttcctg cgttatcccc   2820
tgattctgtg gataaccgta ttaccgctag catggatctc ggggacgtct aactactaag   2880
cgagagtagg gaactgccag gcatcaaata aaacgaaagg ctcagtcgga agactgggcc   2940
tttcgtttta tctgttgttt gtcggtgaac gctctcctga gtaggacaaa tccgccggga   3000
gcggatttga acgttgtgaa gcaacggccc ggagggtggc gggcaggacg cccgccataa   3060
actgccaggc atcaaactaa gcagaaggcc atcctgacgg atggcctttt tgcgtttcta   3120
caaactcttc ctgttagtta gttacttaag ctcgggcccc aaataatgat tttattttga   3180
ctgatagtga cctgttcgtt gcaacaaatt gataagcaat gcttttttat aatgccaact   3240
ttgtacaaaa aagcaggctg cgcgcggaac caattcagtc gacccgggct ggtaacctag   3300
ttaataaatt aaaaggagaa cattattaat gtgaaaatca tgcaaactta aaaaaatcat   3360
caacaacata atttaataat tctaataaaa tatttttttc ttttaattct taatcaatg    3420
tctaacattt atctattatt tatcacattt gttatttaat gtttctatct ttagagctat   3480
caaaaattta aaatggtgga accttactca ttgggttgag ttcacctaac ttgtttaata   3540
aatagatcaa tctaattcta ttcatctctt agtaagtatt aaaaatgttg gcccaactct   3600
ccatatattg gtgagttata ggagtttact cacttaaaat gataataaaa atatttgttt   3660
taaaatcatt ttttaaacaa aaaaataatg tttcagatta tttattctta gatcataact   3720
tacaagcaac atttcaatga tcaattcaat tgtcagaatc aaaaccaatt gaaagagaca   3780
aatattcatg ctaatcttca tcagaaacta acattgaca taaagcaata gtattggaac   3840
tacaagttat aattatgtac tttgtaatag tgtgaagaaa atcaaaatac aaatagtaat   3900
catcatgata aatgctatct caatttattc aattataaaa atatagaaat aaaatgtgat   3960
aaatggataa catgtgtgct aatccagtcc actacgccca ccacaagttc aacccaatgg   4020
actggatcat cttctttttt tcttactgat ttctctcttc ttccattcta atccatccca   4080
aaagtagatg tttactattt cccctttcat agtttcacaa gtgtgcgcag aggccaaact   4140
gaaagtggta gtacatggtg taatattaat cacagatgtg ctctcatgaa gtctgaactt   4200
acagctcaag taacaaccaa caagtaaaaa gtacagaaga tagcataaaa aatgaaggta   4260
gaacaaattc caagttttct acatattacg gtgcataaat caaccacgtg aaggctccat   4320
ttatttgccg ctataacatt ggtgaccctc ttccacaaat agtaagtaat aaaaccaagt   4380
acaaaaaaat gttcaactac caagtgatca caatcttcat gcatctgagt cacactattg   4440
```

```
ccctttgctc atgaagtaca ctttactcac cgccaaagtt cactcaacac tgtagaacaa    4500
aggaatcata taaataatgc atatctctcc cttaagcctt caacacatac aaaagtgaca    4560
caccaaatca aagacacctg agccattcaa ttcccctcct ttattgcttt caagtttcaa    4620
cactaatttt attatctgaa ac                                             4642
```

<210> SEQ ID NO 42
<211> LENGTH: 8187
<212> TYPE: DNA
<213> ORGANISM: Artificial
<220> FEATURE:
<223> OTHER INFORMATION: Nucleotide sequence of PHP25224

<400> SEQUENCE: 42

```
cgcgcgtttc ggtgatgacg gtgaaaacct ctgacacatg cagctcccgg agacggtcac      60
agcttgtctg taagcggatg ccgggagcag acaagcccgt cagggcgcgt cagcgggtgt     120
tggcgggtgt cggggctggc ttaactatgc ggcatcagag cagattgtac tgagagtgca     180
ccatatggac atattgtcgt tagaacgcgg ctacaattaa tacataacct tatgtatcat     240
acacatacga tttaggtgac actatagaac ggcgcgccgg taccgggccc cccctcgagt     300
gcggccgcaa gcttgtcgac ggagatcacc actttgtaca agaaagctga acgagaaacg     360
taaaatgata taaatatcaa tatattaaat tagattttgc ataaaaaaca gactacataa     420
tactgtaaaa cacaacatat ccagtcacta tggtcgacct gcagactggc tgtgtataag     480
ggagcctgac atttatattc cccagaacat caggttaatg gcgttttttga tgtcattttc     540 gcggtggctg agatcagcca cttcttcccc gataacggag accggcacac tggccatatc     600
ggtggtcatc atgcgccagc tttcatcccc gatatgcacc accgggtaaa gttcacggga     660
gactttatct gacagcagac gtgcactggc caggggggatc accatccgtc gcccgggcgt     720
gtcaataata tcactctgta catccacaaa cagacgataa cggctctctc ttttataggt     780
gtaaacctta aactgcattt caccagtccc tgttctcgtc agcaaaagag ccgttcattt     840
caataaaccg ggcgacctca gccatccctt cctgattttc cgctttccag cgttcggcac     900
gcagacgacg gcttcattc tgcatggttg tgcttaccag accggagata ttgacatcat     960
atatgccttg agcaactgat agctgtcgct gtcaactgtc actgtaatac gctgcttcat    1020
agcacacctc tttttgacat acttcgggta tacatatcag tatatattct tataccgcaa    1080
aaatcagcgc gcaaatacgc atactgttat ctggctttta gtaagccgga tccacgcgtt    1140
tacgccccgc cctgccactc atcgcagtac tgttgtaatt cattaagcat tctgccgaca    1200
tggaagccat cacagacggc atgatgaacc tgaatcgcca gcggcatcag caccttgtcg    1260
ccttgcgtat aatatttgcc catggtgaaa acgggggcga agaagttgtc catattggcc    1320
acgtttaaat caaactggt gaaactcacc cagggattgg ctgagacgaa aaacatattc    1380
tcaataaacc ctttagggaa ataggccagg ttttcaccgt aacacgccac atcttgcgaa    1440
tatatgtgta gaaactgccg gaaatcgtcg tggtattcac tccagagcga tgaaaacgtt    1500
tcagtttgct catggaaaac ggtgtaacaa gggtgaacac tatcccatat caccagctca    1560
ccgtctttca ttgccatacg gaattccgga tgagcattca tcaggcgggc aagaatgtga    1620
ataaaggccg gataaaactt gtgcttattt ttctttacgg tctttaaaaa ggccgtaata    1680
tccagctgaa cggtctggtt ataggtacat gagcaactg actgaaatgc ctcaaaatgt    1740
tctttacgat gccattggga tatatcaacg gtggtatatc cagtgatttt tttctccatt    1800
ttagcttcct tagctcctga aaatctcgcc ggatcctaac tcaaaatcca cacttatac    1860
```

```
gagccggaag cataaagtgt aaagcctggg gtgcctaatg cggccgccat agtgactgga    1920
tatgttgtgt tttacagtat tatgtagtct gttttttatg caaaatctaa tttaatatat    1980
tgatatttat atcattttac gtttctcgtt cagcttttt  gtacaaactt gtgattcttc    2040
cttaccaatc atactaatta ttttgggtta aatattaatc attattttta agatattaat    2100
taagaaatta aaagattttt taaaaaaatg tataaaatta tattattcat gattttcat     2160 acatttgatt ttgataataa atatatttt  tttaatttct taaaaaatgt tgcaagacac    2220
ttattagaca tagtcttgtt ctgtttacaa aagcattcat catttaatac attaaaaaat    2280
atttaatact aacagtagaa tcttcttgtg agtggtgtgg gagtaggcaa cctggcattg    2340
aaacgagaga aagagagtca gaaccagaag acaaataaaa agtatgcaac aaacaaatca    2400
aaatcaaagg gcaaaggctg gggttggctc aattggttgc tacattcaat tttcaactca    2460
gtcaacggtt gagattcact ctgacttccc caatctaagc cgcggatgca acggttgaa     2520 tctaacccac aatccaatct cgttacttag gggcttttcc gtcattaact cacccctgcc    2580
acccggtttc cctataaatt ggaactcaat gctcccctct aaactcgtat cgcttcagag    2640
ttgagaccaa gacacactcg ttcatatatc tctctgctct tctcttctct tctacctctc    2700
aaggtacttt tcttctccct ctaccaaatc ctagattccg tggttcaatt tcggatcttg    2760
cacttctggt ttgctttgcc ttgctttttc ctcaactggg tccatctagg atccatgtga    2820
aactctactc tttctttaat atctgcggaa tacgcgtttg actttcagat ctagtcgaaa    2880
tcatttcata attgccttc  tttcttttag cttatgagaa ataaaatcac ttttttttta    2940
tttcaaaata aaccttgggc cttgtgctga ctgagatggg gtttggtgat tacagaatt     3000 tagcgaattt tgtaattgta cttgtttgtc tgtagttttg ttttgttttc ttgtttctca    3060
tacattcctt aggcttcaat tttattcgag tataggtcac aataggaatt caaactttga    3120 gcagggaat  taatcccttc cttcaaatcc agtttgtttg tatatatgtt taaaaaatga    3180
aacttttgct ttaaattcta ttataacttt ttttatggct gaaattttg  catgtgtctt    3240 tgctctctgt tgtaaattta ctgtttaggt actaactcta ggcttgttgt gcagttttg     3300 aagtataacc atgccacaca acacaatggc ggccaccgct tccagaacca cccgattctc    3360
ttcttcctct tcacacccca ccttccccaa acgcattact agatccaccc tccctctctc    3420
tcatcaaacc ctcaccaaac ccaaccacgc tctcaaaatc aaatgttcca tctccaaacc    3480
ccccacggcg gcgcccttca ccaaggaagc gccgaccacg gagcccttcg tgtcacggtt    3540
cgcctccggc gaacctcgca agggcgcgga catccttgtg gaggcgctgg agaggcaggg    3600
cgtgacgacg gtgttcgcgt accccggcgg tgcgtcgatg gagatccacc aggcgctcac    3660
gcgctccgcc gccatccgca acgtgctccc gcgccacgag cagggcggcg tcttcgccgc    3720
cgaaggctac gcgcgttcct ccggcctccc cggcgtctgc attgccacct ccggccccgg    3780
cgccaccaac ctcgtgagcg gcctcgccga cgctttaatg gacagcgtcc cagtcgtcgc    3840
catcaccggc caggtcgccc gccggatgat cggcaccgac gccttccaag aaacccccgat   3900 cgtggaggtg agcagatcca tcacgaagca caactacctc atcctcgacg tcgacgacat    3960 ccccccgcgtc gtcgccgagg cttcttcgt  cgccacctcc ggccgccccg tccggtcct    4020 catcgacatt cccaaagacg ttcagcagca actcgccgtg cctaattggg acgagcccgt    4080
taacctcccc ggttacctcg ccaggctgcc caggccccc  gccgaggccc aattggaaca    4140
cattgtcaga ctcatcatgg aggcccaaaa gcccgttctc tacgtcggcg gtggcagttt    4200
```

```
gaattccagt gctgaattga ggcgctttgt tgaactcact ggtattcccg ttgctagcac    4260
tttaatgggt cttggaactt ttcctattgg tgatgaatat tcccttcaga tgctgggtat    4320
gcatggtact gtttatgcta actatgctgt tgacaatagt gatttgttgc ttgcctttgg    4380
ggtaaggttt tgatgaccgtg ttactgggaa gcttggaggct tttgctagta gggctaagat   4440
tgttcacatt gatattgatt ctgccgagat tgggaagaac aagcaggcgc acgtgtcggt    4500
ttgcgcggat ttgaagttgg ccttgaaggg aattaatatg attttggagg agaaaggagt    4560
ggagggtaag tttgatcttg gaggttggag agaagagatt aatgtgcaga acacaagtt    4620 tccattgggt tacaagacat tccaggacgc gatttctccg cagcatgcta tcgaggttct    4680
tgatgagttg actaatggag atgctattgt tagtactggg gttgggcagc atcaaatgtg    4740
ggctgcgcag ttttacaagt acaagagacc gaggcagtgg ttgacctcag ggggtcttgg    4800
agccatgggt tttggattgc ctgcggctat tggtgctgct gttgctaacc ctggggctgt    4860
tgtggttgac attgatgggg atggtagttt catcatgaat gttcaggagt tggccactat    4920
aagagtggag aatctcccag ttaagatatt gttgttgaac aatcagcatt tgggtatggt    4980
ggttcagttg gaggataggt tctacaagtc caatagagct cacacctatc ttggagatcc    5040
gtctagcgag agcgagatat tcccaaacat gctcaagttt gctgatgctt gtgggatacc    5100
ggcagcgcga gtgacgaaga aggaagagct tagagcggca attcagagaa tgttggacac    5160
ccctggcccc taccttcttg atgtcattgt gccccatcag gagcatgtgt tgccgatgat    5220
tcccagtaat ggatccttca aggatgtgat aactgagggt gatggtagaa cgaggtactg    5280
attgcctaga ccaaatgttc cttgatgctt gttttgtaca atatatataa gataatgctg    5340
tcctagttgc aggatttggc ctgtggtgag catcatagtc tgtagtagtt ttggtagcaa    5400
gacattttat tttccttta tttaacttac tacatgcagt agcatctatc tatctctgta    5460
gtctgatatc tcctgttgtc tgtattgtgc cgttggattt tttgctgtag tgagactgaa    5520
aatgatgtgc tagtaataat atttctgtta gaaatctaag tagagaatct gttgaagaag    5580
tcaaaagcta atggaatcag gttacatatt caatgttttt cttttttag cggttggtag    5640 acgtgtagat tcaacttctc ttggagctca cctaggcaat cagtaaaatg catattcctt    5700
ttttaacttg ccatttattt acttttagtg gaaattgtga ccaatttgtt catgtagaac    5760
ggatttggac cattgcgtcc acaaaacgtc tcttttgctc gatcttcaca aagcgatacc    5820
gaaatccaga gatagttttc aaaagtcaga atggcaaag ttataaatag taaaacagaa    5880
tagatgctgt aatcgacttc aataacaagt ggcatcacgt ttctagttct agacccgggt    5940
accggcgcgc ccgatcatcc ggatatagtt cctcctttca gcaaaaaacc cctcaagacc    6000
cgtttagagg ccccaagggg ttatgctagt tattgctcag cggtggcagc agccaactca    6060
gcttcctttc gggctttgtt agcagccgga tcgatccaag ctgtacctca ctattccttt    6120
gccctcggac gagtgctggg gcgtcggttt ccactatcgg cgagtacttc tacacagcca    6180
tcggtccaga cggccgcgct tctgcgggcg atttgtgtac gcccgacagt cccggctccg    6240
gatcggacga ttgcgtcgca tcgaccctgc gcccaagctg catcatcgaa attgccgtca    6300
accaagctct gatagagttg gtcaagacca atgcggagca tatacgcccg agccgcggc    6360 gatcctgcaa gctccggatg cctccgctcg aagtagcgcg tctgctgctc catacaagcc    6420
aaccacggcc tccagaagaa gatgttggcg acctcgtatt gggaatcccc gaacatcgcc    6480
tcgctccagt caatgaccgc tgttatgcgg ccattgtccg tcaggacatt gttgagccg    6540 aaatccgcgt gcacgaggtg ccggacttcg gggcagtcct cggcccaaag catcagctca    6600
```

| | |
|---|---|
| tcgagagcct gcgcgacgga cgcactgacg gtgtcgtcca tcacagtttg ccagtgatac | 6660 |
| acatggggat cagcaatcgc gcatatgaaa tcacgccatg tagtgtattg accgattcct | 6720 |
| tgcggtccga atgggccgaa cccgctcgtc tggctaagat cggccgcagc gatcgcatcc | 6780 |
| atagcctccg cgaccggctg cagaacagcg ggcagttcgg tttcaggcag gtcttgcaac | 6840 |
| gtgacaccct gtgcacggcg ggagatgcaa taggtcaggc tctcgctgaa ttccccaatg | 6900 |
| tcaagcactt ccggaatcgg gagcgcggcc gatgcaaagt gccgataaac ataacgatct | 6960 |
| tgtagaaaac catcggcgca gctatttacc cgcaggacat atccacgccc tcctacatcg | 7020 |
| aagctgaaag cacgagattc ttcgccctcc gagagctgca tcaggtcgga gacgctgtcg | 7080 |
| aacttttcga tcagaaactt ctcgacagac gtcgcggtga gttcaggctt ttccatgggt | 7140 |
| atatctcctt cttaaagtta aacaaaatta tttctagagg gaaaccgttg tggtctccct | 7200 |
| atagtgagtc gtattaattt cgcgggatcg agatctgatc aacctgcatt aatgaatcgg | 7260 |
| ccaacgcgcg gggagaggcg gtttgcgtat tgggcgctct ccgcttcct cgctcactga | 7320 |
| ctcgctgcgc tcggtcgttc ggctgcggcg agcggtatca gctcactcaa aggcggtaat | 7380 |
| acggttatcc acagaatcag gggataacgc aggaaagaac atgtgagcaa aaggccagca | 7440 |
| aaaggccagg aaccgtaaaa aggccgcgtt gctggcgttt ttccataggc tccgcccccc | 7500 |
| tgacgagcat cacaaaaatc gacgctcaag tcagaggtgg cgaaacccga caggactata | 7560 |
| aagataccag gcgtttcccc ctggaagctc cctcgtgcgc tctcctgttc cgaccctgcc | 7620 |
| gcttaccgga tacctgtccg cctttctccc ttcgggaagc gtggcgcttt ctcaatgctc | 7680 |
| acgctgtagg tatctcagtt cggtgtaggt cgttcgctcc aagctgggct gtgtgcacga | 7740 |
| acccccccgtt cagcccgacc gctgcgcctt atccggtaac tatcgtcttg agtccaaccc | 7800 |
| ggtaagacac gacttatcgc cactggcagc agccactggt aacaggatta gcagagcgag | 7860 |
| gtatgtaggc ggtgctacag agttcttgaa gtggtggcct aactacggct acactagaag | 7920 |
| gacagtattt ggtatctgcg ctctgctgaa gccagttacc ttcggaaaaa gagttggtag | 7980 |
| ctcttgatcc ggcaaacaaa ccaccgctgg tagcggtggt ttttttgttt gcaagcagca | 8040 |
| gattacgcgc agaaaaaaag gatctcaaga agatcctttg atcttttcta cggggtctga | 8100 |
| cgctcagtgg aacgaaaact cacgttaagg gattttggtc atgacattaa cctataaaaa | 8160 |
| taggcgtatc acgaggccct ttcgtct | 8187 |

<210> SEQ ID NO 43
<211> LENGTH: 8945
<212> TYPE: DNA
<213> ORGANISM: Artificial
<220> FEATURE:
<223> OTHER INFORMATION: Nucleotide sequence of QC302

<400> SEQUENCE: 43

| | |
|---|---|
| tttgtacaaa cttgtgattc ttccttacca atcatactaa ttattttggg ttaaatatta | 60 |
| atcattattt ttaagatatt aattaagaaa ttaaagatt ttttaaaaaa atgtataaaa | 120 |
| ttatattatt catgattttt catacatttg attttgataa taatatatt tttttaatt | 180 |
| tcttaaaaaa tgttgcaaga cacttattag acatagtctt gttctgttta caaaagcatt | 240 |
| catcatttaa tacattaaaa aatatttaat actaacagta gaatcttctt gtgagtggtg | 300 |
| tgggagtagg caacctggca ttgaaacgag agaaagagag tcagaaccag aagcaaata | 360 |
| aaaagtatgc aacaaacaaa tcaaaatcaa agggcaaagg ctggggttgg ctcaattggt | 420 |

```
tgctacattc aattttcaac tcagtcaacg gttgagattc actctgactt ccccaatcta    480
agccgcggat gcaaacggtt gaatctaacc cacaatccaa tctcgttact tagggctttt    540
tccgtcatta actcacccct gccacccggt ttccctataa attggaactc aatgctcccc    600
tctaaactcg tatcgcttca gagttgagac caagacacac tcgttcatat atctctctgc    660
tcttctcttc tcttctacct ctcaaggtac ttttcttctc cctctaccaa atcctagatt    720
ccgtggttca atttcggatc ttgcacttct ggtttgcttt gccttgcttt ttcctcaact    780
gggtccatct aggatccatg tgaaactcta ctctttcttt aatatctgcg gaatacgcgt    840
ttgactttca gatctagtcg aaatcattta ataattgcct ttcttctttt agcttatga    900
gaaataaaat cacttttttt ttatttcaaa ataaaccttg gccttgtgc tgactgagat     960
ggggtttggt gattacagaa ttttagcgaa ttttgtaatt gtacttgttt gtctgtagtt   1020
ttgttttgtt ttcttgtttc tcatacattc cttaggcttc aattttattc gagtataggt   1080
cacaatagga attcaaactt tgagcagggg aattaatccc ttccttcaaa tccagtttgt   1140
ttgtatatat gtttaaaaaa tgaaactttt gcttaaattt ctattataac ttttttttatg  1200
gctgaaattt ttgcatgtgt ctttgctctc tgttgtaaat ttactgttta ggtactaact   1260
ctaggcttgt tgtgcagttt ttgaagtata accatgccac acaacacaat ggcggccacc   1320
gcttccagaa ccacccgatt ctcttcttcc tcttcacacc ccaccttccc caaacgcatt   1380
actagatcca ccctccctct ctctcatcaa accctcacca aacccaacca cgctctcaaa   1440
atcaaatgtt ccatctccaa accccccacg gcggcgccct tcaccaagga agcgccgacc   1500
acggagccct tcgtgtcacg gttcgcctcc ggcgaacctc gcaagggcgc ggacatcctt   1560
gtggaggcgc tggagaggca gggcgtgacg acggtgttcg cgtaccccgg cggtgcgtcg   1620
atggagatcc accaggcgct cacgcgctcc gccgccatcc gcaacgtgct cccgcgccac   1680
gagcagggcg gcgtcttcgc cgccgaaggc tacgcgcgtt cctccggcct ccccggcgtc   1740
tgcattgcca cctccggccc cggcgccacc aacctcgtga gcggcctcgc cgacgcttta   1800
atggacagcg tcccagtcgt cgccatcacc ggccaggtcg cccgccggat gatcggcacc   1860
gacgccttcc aagaaacccc gatcgtggag gtgagcagat ccatcacgaa gcacaactac   1920
ctcatcctcg acgtcgacga catcccccgc gtcgtcgccg aggctttctt cgtcgccacc   1980
tccgccgcc ccgtccggt cctcatcgac attcccaaag acgttcagca gcaactcgcc    2040
gtgcctaatt gggacgagcc cgttaacctc cccggttacc tcgccaggct gcccaggccc   2100
cccgccgagg cccaattgga acacattgtc agactcatca tggaggccca aaagcccgtt   2160
ctctacgtcg gcggtggcag tttgaattcc agtgctgaat tgaggcgctt tgttgaactc   2220
actggtattc ccgttgctag cactttaatg ggtcttggaa cttttcctat tggtgatgaa   2280
tattcccttc agatgctggg tatgcatggt actgtttatg ctaactatgc tgttgacaat   2340
agtgatttgt tgcttgcctt tgggtaagg tttgatgacc gtgttactgg gaagcttgag    2400
gcttttgcta gtagggctaa gattgttcac attgatattg attctgccga gattgggaag   2460
aacaagcagg cgcacgtgtc ggtttgcgcg gatttgaagt tggccttgaa gggaattaat   2520
atgattttgg aggagaaagg agtggagggt aagtttgatc ttggaggttg gagagaaaag   2580
attaatgtgc agaaacacaa gtttccattg ggttacaaga cattccagga cgcgatttct   2640
ccgcagcatg ctatcgaggt tcttgatgag ttgactaatg gagatgctat tgttagtact   2700
ggggttgggc agcatcaaat gtgggctgcg cagttttaca agtacaagag accgaggcag   2760
tggttgacct caggggggtct tggagccatg ggttttggat tgcctgcggc tattggtgct   2820
```

```
gctgttgcta accctggggc tgttgtggtt gacattgatg gggatggtag tttcatcatg    2880
aatgttcagg agttggccac tataagagtg gagaatctcc cagttaagat attgttgttg    2940
aacaatcagc atttgggtat ggtggttcag ttggaggata ggttctacaa gtccaataga    3000
gctcacacct atcttggaga tccgtctagc gagagcgaga tattcccaaa catgctcaag    3060
tttgctgatg cttgtgggat accggcagcg cgagtgacga agaaggaaga cttagagcg    3120 gcaattcaga gaatgttgga caccectggc cctaccttc ttgatgtcat tgtgccccat    3180
caggagcatg tgttgccgat gattcccagt aatggatcct tcaaggatgt gataactgag    3240
ggtgatggta gaacgaggta ctgattgcct agaccaaatg ttccttgatg cttgttttgt    3300
acaatatata aagataatg ctgtcctagt tgcaggattt ggcctgtggt gagcatcata    3360
gtctgtagta gttttggtag caagacattt tattttcctt ttatttaact tactacatgc    3420
agtagcatct atctatctct gtagtctgat atctcctgtt gtctgtattg tgccgttgga    3480 tttttttgctg tagtgagact gaaaatgatg tgctagtaat aatatttctg ttagaaatct    3540
aagtagagaa tctgttgaag aagtcaaaag ctaatggaat caggttacat attcaatgtt    3600 tttcttttt tagcggttgg tagacgtgta gattcaactt ctcttggagc tcacctaggc    3660
aatcagtaaa atgcatattc ctttttaac ttgccattta tttactttta gtggaaattg    3720
tgaccaattt gttcatgtag aacggattg gaccatgcg tccacaaaac gtctcttttg    3780
ctcgatcttc acaaagcgat accgaaatcc agagatagtt ttcaaaagtc agaaatggca    3840
aagttataaa tagtaaaaca gaatagatgc tgtaatcgac ttcaataaca agtggcatca    3900
cgtttctagt tctagacccg ggtaccggcg cgcccgatca tccggatata gttcctcctt    3960
tcagcaaaaa acccctcaag acccgtttag aggccccaag gggttatgct agttattgct    4020
cagcggtggc agcagccaac tcagcttcct ttcgggcttt gttagcagcc ggatcgatcc    4080
aagctgtacc tcactattcc tttgccctcg gacgagtgct ggggcgtcgg tttccactat    4140
cggcgagtac ttctacacag ccatcggtcc agacggccgc gcttctgcgg gcgatttgtg    4200
tacgcccgac agtcccggct ccggatcgga cgattgcgtc gcatcgaccc tgcgcccaag    4260
ctgcatcatc gaaattgccg tcaaccaagc tctgatagag ttggtcaaga ccaatgcgga    4320
gcatatacgc ccggagccgc ggcgatcctg caagctccgg atgcctccgc tcgaagtagc    4380
gcgtctgctg ctccatacaa gccaaccacg gcctccagaa gaagatgttg gcgacctcgt    4440
attgggaatc cccgaacatc gcctcgctcc agtcaatgac cgctgttatg cggccattgt    4500
ccgtcaggac attgttggag ccgaaatccg cgtgcacgag gtgccggact cgggggcagt    4560
cctcggccca aagcatcagc tcatcgagag cctgcgcgac ggacgcactg acggtgtcgt    4620
ccatcacagt ttgccagtga tacacatggg gatcagcaat cgcgcatatg aaatcacgcc    4680
atgtagtgta ttgaccgatt ccttgcggtc cgaatgggcc gaacccgctc gtctggctaa    4740
gatcggccgc agcgatcgca tccatagcct ccgcgaccgg ctgcagaaca gcgggcagtt    4800
cggtttcagg caggtcttgc aacgtgacac cctgtgcacg gcgggagatg caataggtca    4860
ggctctcgct gaattcccca atgtcaagca cttccggaat cgggagcgcg gccgatgcaa    4920
agtgccgata aacataacga tctttgtaga aaccatcggc gcagctattt acccgcagga    4980
catatccacg ccctcctaca tcgaagctga agcacgaga ttcttcgccc tccgagagct    5040
gcatcaggtc ggagacgctg tcgaacttttt cgatcagaaa cttctcgaca gacgtcgcgg    5100
tgagttcagg ctttccatg ggtatatctc cttcttaaag ttaaacaaaa ttatttctag    5160
```

```
agggaaaccg ttgtggtctc cctatagtga gtcgtattaa tttcgcggga tcgagatctg    5220
atcaacctgc attaatgaat cggccaacgc gcggggagag gcggtttgcg tattgggcgc    5280
tcttccgctt cctcgctcac tgactcgctg cgctcggtcg ttcggctgcg gcgagcggta    5340
tcagctcact caaaggcggt aatacggtta tccacagaat caggggataa cgcaggaaag    5400
aacatgtgag caaaaggcca gcaaaaggcc aggaaccgta aaaaggccgc gttgctggcg    5460 ttttccata ggctccgccc ccctgacgag catcacaaaa atcgacgctc aagtcagagg    5520
tggcgaaacc cgacaggact ataaagatac caggcgtttc ccctggaag ctccctcgtg    5580 cgctctcctg ttccgaccct gccgcttacc ggatacctgt ccgcctttct cccttcggga    5640
agcgtggcgc tttctcaatg ctcacgctgt aggtatctca gttcggtgta ggtcgttcgc    5700
tccaagctgg gctgtgtgca cgaacccccc gttcagcccg accgctgcgc cttatccggt    5760
aactatcgtc ttgagtccaa cccggtaaga cacgacttat cgccactggc agcagccact    5820
ggtaacagga ttagcagagc gaggtatgta ggcggtgcta cagagttctt gaagtggtgg    5880
cctaactacg gctacactag aaggacagta tttggtatct gcgctctgct gaagccagtt    5940
accttcggaa aaagagttgg tagctcttga tccggcaaac aaaccaccgc tggtagcggt    6000
ggtttttttg tttgcaagca gcagattacg cgcagaaaaa aaggatctca agaagatcct    6060
ttgatctttt ctacggggtc tgacgctcag tggaacgaaa actcacgtta agggattttg    6120
gtcatgacat taacctataa aaataggcgt atcacgaggc cctttcgtct cgcgcgtttc    6180
ggtgatgacg gtgaaaacct ctgacacatg cagctcccgg agacggtcac agcttgtctg    6240
taagcggatg ccgggagcag acaagcccgt cagggcgcgt cagcgggtgt tggcgggtgt    6300
cggggctggc ttaactatgc ggcatcagag cagattgtac tgagagtgca ccatatggac    6360
atattgtcgt tagaacgcgg ctacaattaa tacataaccct tatgtatcat acacatacga    6420
tttaggtgac actatagaac ggcgcgccgg taccgggccc ccctcgagt gcggccgcaa    6480 gcttgtcgac ggagatcacc actttgtaca agaaagctgg gtctagatat ctcgagtgcg    6540
gccgccagtg tgatggatat cagctgggcc ggccactaga attcccgatc tagtaacata    6600
gatgacaccg cgcgcgataa tttatcctag tttgcgcgct atattttgtt ttctatcgcg    6660
tattaaatgt ataattgcgg gactctaatc ataaaaaccc atctcataaa taacgtcatg    6720
cattacatgt taattattac atgcttaacg taattcaaca gaaattatat gataatcatc    6780
gcaagaccgg caacaggatt caatcttaag aaactttatt gccaaatgtt tgaacgatcg    6840
gggaaattcg agctctcagg ccagggcgct ggggaaggcg atggcgtgct cggtcagctg    6900
ccacttctgg ttcttggcgt cgctccggtc ctcccgcagc agcttgtgct ggatgaagtg    6960
ccactcgggc atcttgctgg gcacgctctt ggccttgtac acggtgtcga actggcaccg    7020
gtaccggccg ccgtccttca gcagcaggta catgctcacg tcgcccttca ggatgccctg    7080
cttaggcacg gcatgatct ctcgcagct ggcctcccag ttggtggtca tcttcttcat    7140
cacggggccg tcgcgggga agttcacgcc gttgaagatg ctcttgtggt agatgcagtt    7200
ctccttcacg ctcacggtga tgtccacgtt acagatgcac acggcgccgt cctcgaacag    7260
gaagctccgg ccccaggtgt agccggcggg gcagctgttc ttgaagtagt ccacgatgtc    7320
ctgggggtac tcggtgaaga tccggtcgcc gtacttgaag ccggcgctca ggatgtcctc    7380
gctgaagggc agggggccgc cctcgatcac gcacaggttg atggtctgct tgcccttgaa    7440
ggggtagccg atgccctcgc cggtgatcac gaacttgtgg ccgttcacgc agccctccat    7500
gtggtacttc atggtcatct cctccttcag gccgtgcttg ctgtgggcca tggtttcaga    7560
```

```
taataaaatt agtgttgaaa cttgaaagca ataaaggagg ggaattgaat ggctcaggtg    7620
tctttgattt ggtgtgtcac ttttgtatgt gttgaaggct taagggagag atatgcatta    7680
tttatatgat tcctttgttc tacagtgttg agtgaacttt ggcggtgagt aaagtgtact    7740
tcatgagcaa agggcaatag tgtgactcag atgcatgaag attgtgatca cttggtagtt    7800
gaacattttt ttgtacttgg ttttattact tactatttgt ggaagagggt caccaatgtt    7860
atagcggcaa ataatggag ccttcacgtg gttgatttat gcaccgtaat atgtagaaaa     7920
cttggaattt gttctacctt catttttat gctatcttct gtactttta cttgttggtt      7980 gttacttgag ctgtaagttc agacttcatg agagcacatc tgtgattaat attacaccat    8040
gtactaccac tttcagtttg gcctctgcgc acacttgtga actatgaaa ggggaaatag     8100 taaacatcta cttttgggat ggattagaat ggaagaagag agaaatcagt aagaaaaaaa    8160
gaagatgatc cagtccattg ggttgaactt gtggtgggcg tagtggactg gattagcaca    8220
catgttatcc atttatcaca ttttatttct atatttttat aattgaataa attgagatag    8280
catttatcat gatgattact atttgtattt tgattttctt cacactatta caaagtacat    8340
aattataact tgtagttcca atactattgc tttatgtcaa tgtttagttt ctgatgaaga    8400
ttagcatgaa tatttgtctc tttcaattgg ttttgattct gacaattgaa ttgatcattg    8460
aaatgttgct tgtaagttat gatctaagaa taaataatct gaaacattat tttttgttt    8520 aaaaaatgat tttaaaacaa atatttttat tatcatttta agtgagtaaa ctcctataac    8580
tcaccaatat atggagagtt gggccaacat ttttaatact tactaagaga tgaatagaat    8640
tagattgatc tatttattaa acaagttagg tgaactcaac ccaatgagta aggttccacc    8700
attttaaatt tttgatagct ctaaagatag aaacattaaa taacaaatgt gataaataat    8760
agataaatgt tagacattga ttaaagaatt aaaagaaaaa aatattttat tagaattata    8820
aaattatgtt gttgatgatt ttttaagtt tgcatgattt tcacattaat aatgttctcc     8880 ttttaatta ttaactaggt taccagcccg ggtcgactga attggttccg gcgccagcct     8940
gcttt                                                                8945

<210> SEQ ID NO 44
<211> LENGTH: 2817
<212> TYPE: DNA
<213> ORGANISM: Artificial
<220> FEATURE:
<223> OTHER INFORMATION: Nucleotide sequence of pCR8/GW/TOPO

<400> SEQUENCE: 44
ctttcctgcg ttatcccctg attctgtgga taaccgtatt accgcctttg agtgagctga     60
taccgctcgc cgcagccgaa cgaccgagcg cagcgagtca gtgagcgagg aagcggaaga    120
gcgcccaata cgcaaaccgc ctctccccgc gcgttggccg attcattaat gcagctggca    180
cgacaggttt cccgactgga aagcgggcag tgagcgcaac gcaattaata cgcgtaccgc    240
tagccaggaa gagtttgtag aaacgcaaaa aggccatccg tcaggatggc cttctgctta    300
gtttgatgcc tggcagttta tggcgggcgt cctgcccgcc accctccggg ccgttgcttc    360
acaacgttca aatccgctcc cggcggattt gtcctactca ggagagcgtt caccgacaaa    420
caacagataa aacgaaaggc ccagtcttcc gactgagcct ttcgttttat ttgatgcctg    480
gcagttccct actctcgcgt taacgctagc atggatgttt tcccagtcac gacgttgtaa    540
aacgacggcc agtcttaagc tcgggcccca ataatgatt ttatttgac tgatagtgac      600
```

```
ctgttcgttg caacaaattg atgagcaatg cttttttata atgccaactt tgtacaaaaa    660
agcaggctcc gaattcgccc ttaagggcga attcgaccca gctttcttgt acaaagttgg    720
cattataaaa aataattgct catcaatttg ttgcaacgaa caggtcacta tcagtcaaaa    780
taaaatcatt atttgccatc cagctgatat cccctatagt gagtcgtatt acatggtcat    840
agctgttccc tggcagctct ggcccgtgtc tcaaaatctc tgatgttaca ttgcacaaga    900
taaaaatata tcatcatgcc tcctctagac cagccaggac agaaatgcct cgacttcgct    960
gctgcccaag gttgccgggt gacgcacacc gtggaaacgg atgaaggcac gaacccagtg   1020
gacataagcc tgttcggttc gtaagctgta atgcaagtag cgtatgcgct cacgcaactg   1080
gtccagaacc ttgaccgaac gcagcggtgg taacggcgca gtggcggttt tcatggcttg   1140
ttatgactgt ttttttgggg tacagtctat gcctcgggca tccaagcagc aagcgcgtta   1200
cgccgtgggt cgatgtttga tgttatggag cagcaacgat gttacgcagc agggcagtcg   1260
ccctaaaaca aagttaaaca tcatgaggga agcggtgatc gccgaagtat cgactcaact   1320
atcagaggta gttggcgtca tcgagcgcca tctcgaaccg acgttgctgg ccgtacattt   1380
gtacggctcc gcagtggatg gcggcctgaa gccacacagt gatattgatt tgctggttac   1440
ggtgaccgta aggcttgatg aaacaacgcg gcgagctttg atcaacgacc ttttggaaac   1500
ttcggcttcc cctggagaga gcgagattct ccgcgctgta aagtcacca ttgttgtgca   1560 cgacgacatc attccgtggc gttatccagc taagcgcgaa ctgcaatttg gagaatggca   1620
gcgcaatgac attcttgcag gtatcttcga gccagccacg atcgacattg atctggctat   1680
cttgctgaca aaagcaagag aacatagcgt tgccttggta ggtccagcgg cggaggaact   1740
ctttgatccg gttcctgaac aggatctatt tgaggcgcta atgaaacct taacgctatg   1800 gaactcgccg cccgactggg ctggcgatga gcgaaatgta gtgcttacgt tgtcccgcat   1860
ttggtacagc gcagtaaccg gcaaaatcgc gccgaaggat gtcgctgccg actgggcaat   1920
ggagcgcctg ccgcccagt atcagcccgt catacttgaa gctagacagg cttatcttgg   1980
acaagaagaa gatcgcttgg cctcgcgcgc agatcagttg gaagaatttg tccactacgt   2040
gaaaggcgag atcaccaagg tagtcggcaa ataaccctcg agccacccat gaccaaaatc   2100
ccttaacgtg agttacgcgt cgttccactg agcgtcagac cccgtagaaa agatcaaagg   2160
atcttcttga tccttttttt ttctgcgcgt aatctgctgc ttgcaaacaa aaaaaccacc   2220
gctaccagcg gtggtttgtt tgccggatca agagctacca actctttttc cgaaggtaac   2280
tggcttcagc agagcgcaga taccaaatac tgtccttcta gtgtagccgt agttaggcca   2340
ccacttcaag aactctgtag caccgcctac atacctcgct ctgctaatcc tgttaccagt   2400
ggctgctgcc agtggcgata gtcgtgtct taccgggttg gactcaagac gatagttacc   2460
ggataaggcg cagcggtcgg gctgaacggg gggttcgtgc acacagccca gcttggagcg   2520
aacgacctac accgaactga gatacctaca gcgtgagcat tgagaaagcg ccacgcttcc   2580
cgaagggaga aaggcggaca ggtatccggt aagcggcagg gtcggaacag gagagcgcac   2640
gagggagctt ccaggggaa acgcctggta tctttatagt cctgtcgggt ttcgccacct   2700
ctgacttgag cgtcgatttt tgtgatgctc gtcagggggg cggagcctat ggaaaaacgc   2760
cagcaacgcg gccttttac ggttcctggc cttttgctgg ccttttgctc acatgtt      2817
```

<210> SEQ ID NO 45
<211> LENGTH: 4145
<212> TYPE: DNA
<213> ORGANISM: Artificial
<220> FEATURE:
<223> OTHER INFORMATION: Nucleotide sequence of QC300-1

<400> SEQUENCE: 45

```
aagggcgaat tcgacccagc tttcttgtac aaagttggca ttataaaaaa taattgctca     60
tcaatttgtt gcaacgaaca ggtcactatc agtcaaaata aaatcattat ttgccatcca    120
gctgatatcc cctatagtga gtcgtattac atggtcatag ctgtttcctg gcagctctgg    180
cccgtgtctc aaaatctctg atgttacatt gcacaagata aaaatatatc atcatgcctc    240
ctctagacca gccaggacag aaatgcctcg acttcgctgc tgcccaaggt tgccgggtga    300
cgcacaccgt ggaaacggat gaaggcacga acccagtgga cataagcctg ttcggttcgt    360
aagctgtaat gcaagtagcg tatgcgctca cgcaactggt ccagaacctt gaccgaacgc    420
agcggtggta acgcgcagt ggcggttttc atggcttgtt atgactgttt ttttgggta     480 cagtctatgc ctcgggcatc caagcagcaa gcgcgttacg ccgtgggtcg atgtttgatg    540
ttatggagca gcaacgatgt tacgcagcag ggcagtcgcc ctaaaacaaa gttaaacatc    600
atgagggaag cggtgatcgc cgaagtatcg actcaactat cagaggtagt tggcgtcatc    660
gagcgccatc tcgaaccgac gttgctggcc gtacatttgt acggctccgc agtggatggc    720
ggcctgaagc cacacagtga tattgatttg ctggttacgg tgaccgtaag gcttgatgaa    780
acaacgcggc gagctttgat caacgacctt ttggaaactt cggcttcccc tggagagagc    840
gagattctcc gcgctgtaga agtcaccatt gttgtgcacg acgacatcat tccgtggcgt    900
tatccagcta agcgcgaact gcaatttgga gaatggcagc gcaatgacat tcttgcaggt    960
atcttcgagc cagccacgat cgacattgat ctggctatct tgctgacaaa agcaagagaa   1020
catagcgttg ccttggtagg tccagcggcg gaggaactct tgatccggt tcctgaacag    1080 gatctatttg aggcgctaaa tgaaaccta acgctatgga actcgccgcc cgactgggct    1140
ggcgatgagc gaaatgtagt gcttacgttg tcccgcattt ggtacagcgc agtaaccggc    1200
aaaatcgcgc cgaaggatgt cgctgccgac tgggcaatgg agcgcctgcc ggcccagtat   1260
cagcccgtca tacttgaagc tagacaggct tatcttggac aagaagaaga tcgcttggcc   1320
tcgcgcgcag atcagttgga agaatttgtc cactacgtga aaggcgagat caccaaggta   1380
gtcggcaaat aaccctcgag ccacccatga ccaaaatccc ttaacgtgag ttacgcgtcg   1440
ttccactgag cgtcagaccc cgtagaaaag atcaaaggat cttcttgaga tccttttttt   1500
ctgcgcgtaa tctgctgctt gcaaacaaaa aaaccaccgc taccagcggt ggtttgtttg   1560
ccggatcaag agctaccaac tcttttccg aaggtaactg gcttcagcag agcgcagata   1620
ccaaatactg tccttctagt gtagccgtag ttaggccacc acttcaagaa ctctgtagca   1680
ccgcctacat acctcgctct gctaatcctg ttaccagtgg ctgctgccag tggcgataag   1740
tcgtgtctta ccgggttgga ctcaagacga tagttaccgg ataaggcgca gcggtcgggc   1800
tgaacggggg gttcgtgcac acagcccagc ttggagcgaa cgacctacac cgaactgaga   1860
tacctacagc gtgagcattg agaaagcgcc acgcttcccg aagggagaaa ggcggacagg   1920
tatccggtaa gcggcagggt cggaacagga gagcgcacga gggagcttcc agggggaaac   1980
gcctggtatc tttatagtcc tgtcgggttt cgccacctct gacttgagcg tcgatttttg   2040
tgatgctcgt cagggggggcg gagcctatgg aaaaacgcca gcaacgcggc cttttacgg    2100 ttcctggcct tttgctggcc ttttgctcac atgttcttc ctgcgttatc ccctgattct   2160
gtggataacc gtattaccgc ctttgagtga gctgataccg ctcgccgcag ccgaacgacc   2220
```

```
gagcgcagcg agtcagtgag cgaggaagcg gaagagcgcc caatacgcaa accgcctctc      2280
cccgcgcgtt ggccgattca ttaatgcagc tggcacgaca ggtttcccga ctggaaagcg      2340
ggcagtgagc gcaacgcaat taatacgcgt accgctagcc aggaagagtt tgtagaaacg      2400
caaaaaggcc atccgtcagg atggccttct gcttagtttg atgcctggca gtttatggcg      2460
ggcgtcctgc ccgccaccct ccgggccgtt gcttcacaac gttcaaatcc gctcccggcg      2520
gatttgtcct actcaggaga gcgttcaccg acaaacaaca gataaaacga aaggcccagt      2580
cttccgactg agcctttcgt tttatttgat gcctggcagt tccctactct cgcgttaacg      2640
ctagcatgga tgttttccca gtcacgacgt tgtaaaacga cggccagtct taagctcggg      2700
ccccaaataa tgattttatt ttgactgata gtgacctgtt cgttgcaaca aattgatgag      2760
caatgctttt ttataatgcc aactttgtac aaaaaagcag gctccgaatt cgcccttgga      2820
gaacattatt aatgtgaaaa tcatgcaaac ttaaaaaaat catcaacaac ataatttttat     2880 aattctaata aaatattttt ttcttttaat tctttaatca atgtctaaca tttatctatt      2940
atttatcaca tttgttattt aatgtttcta tctttagagc tatcaaaaat ttaaaatggt      3000
ggaaccttac tcattgggtt gagttcacct aacttgttta ataaatagat caatctaatt      3060
ctattcatct cttagtaagt attaaaaatg ttggcccaac tctccatata ttggtgagtt      3120
ataggagttt actcacttaa aatgataata aaaatatttg ttttaaaatc attttttaaa      3180
caaaaaaata atgtttcaga ttatttattc ttagatcata acttacaagc aacatttcaa      3240
tgatcaattc aattgtcaga atcaaaacca attgaaagag acaaatattc atgctaatct      3300
tcatcagaaa ctaaacattg acataaagca atagtattgg aactacaagt tataattatg      3360
tactttgtaa tagtgtgaag aaaatcaaaa tacaaatagt aatcatcatg ataaatgcta      3420
tctcaattta ttcaattata aaaatataga aataaaatgt gataaatgga taacatgtgt      3480
gctaatccag tccactacgc ccaccacaag ttcaacccaa tggactggat catcttcttt      3540 tttttcttact gatttctctc ttcttccatt ctaatccatc ccaaaagtag atgtttacta     3600 ttttccccttt catagttttca caagtgtgcg cagaggccaa actgaaagtg gtagtacatg     3660
gtgtaatatt aatcacagat gtgctctcat gaagtctgaa cttacagctc aagtaacaac      3720
caacaagtaa aaagtacaga agatagcata aaaaatgaag gtagaacaaa ttccaagttt      3780
tctacatatt acggtgcata aatcaaccac gtgaaggctc catttatttg ccgctataac      3840
attggtgacc ctcttccaca aatagtaagt aataaaacca agtacaaaaa aatgttcaac      3900
taccaagtga tcacaatctt catgcatctg agtcacacta ttgccctttg ctcatgaagt      3960
acactttact caccgccaaa gttcactcaa cactgtagaa caaaggaatc atataaataa      4020
tgcatatctc tcccttaagc cttcaacaca tacaaaagtg acacaccaaa tcaaagacac      4080
ctgagccatt caattcccct cctttattgc tttcaagttt caacactaat tttattatct      4140
gaaac                                                                 4145
```

<210> SEQ ID NO 46
<211> LENGTH: 5286
<212> TYPE: DNA
<213> ORGANISM: Artificial
<220> FEATURE:
<223> OTHER INFORMATION: Nucleotide sequence of QC330

<400> SEQUENCE: 46

```
atcaacaagt ttgtacaaaa aagctgaacg agaaacgtaa aatgatataa atatcaatat        60
attaaattag attttgcata aaaaacagac tacataatac tgtaaaacac aacatatcca       120
```

```
gtcatattgg cggccgcatt aggcacccca ggctttacac tttatgcttc cggctcgtat    180
aatgtgtgga ttttgagtta ggatccgtcg agattttcag gagctaagga agctaaaatg    240
gagaaaaaaa tcactggata taccaccgtt gatatatccc aatggcatcg taaagaacat    300
tttgaggcat ttcagtcagt tgctcaatgt acctataacc agaccgttca gctggatatt    360
acggcctttt taaagaccgt aaagaaaaat aagcacaagt tttatccggc ctttattcac    420
attcttgccc gcctgatgaa tgctcatccg gaattccgta tggcaatgaa agacggtgag    480
ctggtgatat gggatagtgt tcacccttgt tacaccgttt tccatgagca aactgaaacg    540
ttttcatcgc tctggagtga ataccacgac gatttccggc agtttctaca catatattcg    600
caagatgtgg cgtgttacgg tgaaaacctg gcctatttcc ctaaagggtt tattgagaat    660 atgttttttcg tctcagccaa tccctgggtg agtttcacca gttttgattt aaacgtggcc    720
aatatggaca acttcttcgc ccccgttttc accatgggca aatattatac gcaaggcgac    780
aaggtgctga tgccgctggc gattcaggtt catcatgccg tttgtgatgg cttccatgtc    840
ggcagaatgc ttaatgaatt acaacagtac tgcgatgagt ggcagggcgg ggcgtaaaga    900
tctggatccg gcttactaaa agccagataa cagtatgcgt atttgcgcgc tgattttttgc    960 ggtataagaa tatatactga tatgtatacc cgaagtatgt caaaaagagg tatgctatga   1020
agcagcgtat tacagtgaca gttgacagcg acagctatca gttgctcaag gcatatatga   1080
tgtcaatatc tccggtctgg taagcacaac catgcagaat gaagcccgtc gtctgcgtgc   1140
cgaacgctgg aaagcggaaa tcaggaagg atggctgag gtcgcccggt ttattgaaat   1200
gaacggctct tttgctgacg agaacagggg ctggtgaaat gcagtttaag gtttacacct   1260
ataaaagaga gagccgttat cgtctgtttg tggatgtaca gagtgatatt attgacacgc   1320
ccgggcgacg gatggtgatc cccctggcca gtgcacgtct gctgtcagat aaagtctccc   1380
gtgaacttta cccggtggtg catatcgggg atgaaagctg gcgcatgatg accaccgata   1440
tggccagtgt gccggtctcc gttatcgggg aagaagtggc tgatctcagc caccgcgaaa   1500 atgcatcaa aaacgccatt aacctgatgt tctggggaat ataaatgtca ggctccctta   1560
tacacagcca gtctgcaggt cgaccatagt gactggatat gttgtgtttt acagtattat   1620
gtagtctgtt ttttatgcaa aatctaattt aatatattga tatttatatc attttacgtt   1680
tctcgttcag ctttccttgta caaagtggtt gatgggatcc atgcccaca gcaagcacgg   1740 cctgaaggag gagatgacca tgaagtacca catggagggc tgcgtgaacg gccacaagtt   1800
cgtgatcacc ggcgagggca tcggctaccc cttcaagggc aagcagacca tcaacctgtg   1860
cgtgatcgag ggcggccccc tgcccttcag cgaggacatc ctgagcgccg gcttcaagta   1920
cggcgaccgg atcttcaccg agtacccca ggacatcgtg gactacttca gaacagctg   1980 ccccgccggc tacacctggg gccggagctt cctgttcgag gacggcgccg tgtgcatctg   2040
taacgtggac atcaccgtga gcgtgaagga gaactgcatc taccacaaga gcatcttcaa   2100
cggcgtgaac ttccccgccg acggccccgt gatgaagaag atgaccacca actgggaggc   2160
cagctgcgag aagatcatgc ccgtgcctaa gcagggcatc ctgaagggcg acgtgagcat   2220
gtacctgctg ctgaaggacg gcggccgta ccggtgccag ttcgacaccg tgtacaaggc   2280
caagagcgtg cccagcaaga tgcccgagtg gcacttcatc cagcacaagc tgctgcggga   2340
ggaccggagc gacgccaaga accagaagtg cagctgacc gagcacgcca tcgccttccc   2400
cagcgccctg gcctgagagc tcgaatttcc ccgatcgttc aaacatttgg caataaagtt   2460
```

```
tcttaagatt gaatcctgtt gccggtcttg cgatgattat catataattt ctgttgaatt      2520
acgttaagca tgtaataatt aacatgtaat gcatgacgtt atttatgaga tgggttttta      2580
tgattagagt cccgcaatta tacatttaat acgcgataga aaacaaaata tagcgcgcaa      2640
actaggataa attatcgcgc gcggtgtcat ctatgttact agatcgggaa ttctagtggc      2700
cggcccagct gatatccatc acactggcgg ccgctcgagt tctatagtgt cacctaaatc      2760
gtatgtgtat gatacataag gttatgtatt aattgtagcc gcgttctaac gacaatatgt      2820
ccatatggtg cactctcagt acaatctgct ctgatgccgc atagttaagc cagccccgac      2880
acccgccaac cccgctgac gcgcctgac gggcttgtct gctcccggca tccgcttaca       2940
gacaagctgt gaccgtctcc gggagctgca tgtgtcagag gttttcaccg tcatcaccga      3000
aacgcgcgag acgaaagggc ctcgtgatac gcctattttt ataggttaat gtcatgacca      3060 aaatcccctta acgtgagttt tcgttccact gagcgtcaga ccccgtagaa aagatcaaag      3120
gatcttcttg agatcctttt tttctgcgcg taatctgctg cttgcaaaca aaaaaaccac      3180
cgctaccagc ggtggtttgt ttgccggatc aagagctacc aactcttttt ccgaaggtaa      3240
ctggcttcag cagagcgcag ataccaaata ctgtccttct agtgtagccg tagttaggcc      3300
accacttcaa gaactctgta gcaccgccta catacctcgc tctgctaatc ctgttaccag      3360
tggctgctgc cagtggcgat aagtcgtgtc ttaccgggtt ggactcaaga cgatagttac      3420
cggataaggc gcagcggtcg ggctgaacgg ggggttcgtg cacacagccc agcttggagc      3480
gaacgaccta caccgaactg agatacctac agcgtgagca ttgagaaagc gccacgcttc      3540
ccgaagggag aaaggcggac aggtatccgg taagcggcag ggtcggaaca ggagagcgca      3600
cgagggagct ccagggggga aacgcctggt atctttatag tcctgtcggg tttcgccacc      3660
tctgacttga gcgtcgattt tgtgatgct cgtcaggggg gcggagccta tggaaaaacg       3720
ccagcaacgc ggcctttta cggttcctgg ccttttgctg gccttttgct cacatgttct       3780
ttcctgcgtt atcccctgat tctgtggata accgtattac cgcctttgag tgagctgata      3840
ccgctcgccg cagccgaacg accgagcgca gcgagtcagt gagcgaggaa gcggaagagc      3900
gcccaatacg caaaccgcct ctccccgcgc gttggccgat tcattaatgc aggttgatca      3960
gatctcgatc ccgcgaaatt aatacgactc actataggga gaccacaacg gtttccctct      4020
agaaataatt ttgtttaact ttaagaagga gatatacca tggaaaagcc tgaactcacc       4080
gcgacgtctg tcgagaagtt tctgatcgaa aagttcgaca gcgtctccga cctgatgcag      4140
ctctcggagg gcgaagaatc tcgtgctttc agcttcgatg taggagggcg tggatatgtc      4200
ctgcgggtaa atagctgcgc cgatggtttc tacaaagatc gttatgttta tcggcacttt      4260
gcatcggccg cgctcccgat tccggaagtg cttgacattg gggaattcag cgagagcctg      4320
acctattgca tctcccgccg tgcacagggt gtcacgttgc aagacctgcc tgaaaccgaa      4380
ctgcccgctg ttctgcagcc ggtcgcggag gctatggatg cgatcgctgc ggccgatctt      4440
agccagacga gcgggttcgg cccattcgga ccgcaaggaa tcggtcaata cactacatgg      4500
cgtgatttca tatgcgcgat tgctgatccc catgtgtatc actggcaaac tgtgatggac      4560
gacaccgtca gtgcgtccgt cgcgcaggct ctcgatgagc tgatgctttg gccgaggac      4620 tgccccgaag tccggcacct cgtgcacgcg gatttcggct ccaacaatgt cctgacggac      4680
aatggccgca taacagcggt cattgactgg agcgaggcga tgttcgggga ttcccaatac      4740
gaggtcgcca acatcttctt ctggaggccg tggttggctt gtatggagca gcagacgcgc      4800
tacttcgagc ggaggcatcc ggagcttgca ggatcgccgc ggctccgggc gtatatgctc      4860
```

| | |
|---|---:|
| cgcattggtc ttgaccaact ctatcagagc ttggttgacg gcaatttcga tgatgcagct | 4920 |
| tgggcgcagg gtcgatgcga cgcaatcgtc cgatccggag ccgggactgt cgggcgtaca | 4980 |
| caaatcgccc gcagaagcgc ggccgtctgg accgatggct gtgtagaagt actcgccgat | 5040 |
| agtggaaacc gacgcccccag cactcgtccg agggcaaagg aatagtgagg tacagcttgg | 5100 |
| atcgatccgg ctgctaacaa agcccgaaag gaagctgagt tggctgctgc caccgctgag | 5160 |
| caataactag cataacccct tggggcctct aaacgggtct tgaggggttt tttgctgaaa | 5220 |
| ggaggaacta tatccggatg atcgtcgagg cctcacgtgt taacaagctt gcatgcctgc | 5280 |
| aggttt | 5286 |

<210> SEQ ID NO 47
<211> LENGTH: 4986
<212> TYPE: DNA
<213> ORGANISM: Artificial
<220> FEATURE:
<223> OTHER INFORMATION: Nucleotide sequence of QC300-1Y

<400> SEQUENCE: 47

| | |
|---|---:|
| cttgtacaaa gtggttgatg ggatccatgg cccacagcaa gcacggcctg aaggaggaga | 60 |
| tgaccatgaa gtaccacatg gagggctgcg tgaacggcca caagttcgtg atcaccggcg | 120 |
| agggcatcgg ctacccttc aagggcaagc agaccatcaa cctgtgcgtg atcgagggcg | 180 |
| gcccctgcc cttcagcgag gacatcctga gcgccggctt caagtacggc gaccggatct | 240 |
| tcaccgagta cccccaggac atcgtggact acttcaagaa cagctgcccc gccggctaca | 300 |
| cctggggccg gagcttcctg ttcgaggacg gcgccgtgtg catctgtaac gtggacatca | 360 |
| ccgtgagcgt gaaggagaac tgcatctacc acaagagcat cttcaacggc gtgaacttcc | 420 |
| ccgccgacgg cccccgtgatg aagaagatga ccaccaactg ggaggccagc tgcgagaaga | 480 |
| tcatgcccgt gcctaagcag ggcatcctga agggcgacgt gagcatgtac ctgctgctga | 540 |
| aggacggcgg ccggtaccgg tgccagttcg acaccgtgta caaggccaag agcgtgccca | 600 |
| gcaagatgcc cgagtggcac ttcatccagc acaagctgct gcgggaggac cggagcgacg | 660 |
| ccaagaacca gaagtggcag ctgaccgagc acgccatcgc cttccccagc gccctggcct | 720 |
| gagagctcga atttccccga tcgttcaaac atttggcaat aaagtttctt aagattgaat | 780 |
| cctgttgccg gtcttgcgat gattatcata taatttctgt tgaattacgt taagcatgta | 840 |
| ataattaaca tgtaatgcat gacgttattt atgagatggg ttttatgat tagagtcccg | 900 |
| caattataca tttaatacgc gatagaaaac aaaatatagc gcgcaaacta ggataaatta | 960 |
| tcgcgcgcgg tgtcatctat gttactagat cgggaattct agtggccggc cagctgata | 1020 |
| tccatcacac tggcggccgc tcgagttcta tagtgtcacc taaatcgtat gtgtatgata | 1080 |
| cataaggtta tgtattaatt gtagccgcgt tctaacgaca atatgtccat atggtgcact | 1140 |
| ctcagtacaa tctgctctga tgccgcatag ttaagccagc cccgacaccc gccaacaccc | 1200 |
| gctgacgcgc cctgacgggc ttgtctgctc ccggcatccg cttacagaca agctgtgacc | 1260 |
| gtctccggga gctgcatgtg tcagaggttt tcaccgtcat caccgaaacg cgcgagacga | 1320 |
| aagggcctcg tgatacgcct atttttatag gttaatgtca tgaccaaaat cccttaacgt | 1380 |
| gagttttcgt tccactgagc gtcagacccc gtagaaaaga tcaaaggatc ttcttgagat | 1440 |
| cctttttttc tgcgcgtaat ctgctgcttg caaacaaaaa aaccaccgct accagcggtg | 1500 |
| gtttgtttgc cggatcaaga gctaccaact ctttttccga aggtaactgg cttcagcaga | 1560 |

-continued

```
gcgcagatac caaatactgt ccttctagtg tagccgtagt taggccacca cttcaagaac      1620
tctgtagcac cgcctacata cctcgctctg ctaatcctgt taccagtggc tgctgccagt      1680
ggcgataagt cgtgtcttac cgggttggac tcaagacgat agttaccgga taaggcgcag      1740
cggtcgggct gaacgggggg ttcgtgcaca cagcccagct tggagcgaac gacctacacc      1800
gaactgagat acctacagcg tgagcattga aaagcgcca cgcttccga agggagaaag      1860 gcggacaggt atccggtaag cggcagggtc ggaacaggag agcgcacgag ggagcttcca      1920
gggggaaacg cctggtatct ttatagtcct gtcgggtttc gccacctctg acttgagcgt      1980 cgattttgt gatgctcgtc aggggggcgg agcctatgga aaaacgccag caacgcggcc      2040 ttttttacggt tcctggcctt ttgctggcct tttgctcaca tgttctttcc tgcgttatcc      2100
cctgattctg tggataaccg tattaccgcc tttgagtgag ctgataccgc tcgccgcagc      2160
cgaacgaccg agcgcagcga gtcagtgagc gaggaagcgg aagagcgccc aatacgcaaa      2220
ccgcctctcc ccgcgcgttg ccgattcat taatgcaggt tgatcagatc tcgatcccgc      2280
gaaattaata cgactcacta tagggagacc acaacggttt ccctctagaa ataattttgt      2340
ttaactttaa gaaggagata tacccatgga aaagcctgaa ctcaccgcga cgtctgtcga      2400
gaagtttctg atcgaaaagt tcgacagcgt ctccgacctg atgcagctct cggagggcga      2460
agaatctcgt gctttcagct tcgatgtagg agggcgtgga tatgtcctgc gggtaaatag      2520
ctgcgccgat ggtttctaca agatcgtta tgtttatcgg cactttgcat cggccgcgct      2580
cccgattccg gaagtgcttg acattgggga attcagcgag agcctgacct attgcatctc      2640
ccgccgtgca cagggtgtca cgttgcaaga cctgcctgaa accgaactgc cgctgttct      2700 gcagccggtc gcggaggcta tggatgcgat cgctgcggcc gatcttagcc agacgagcgg      2760
gttcggccca ttcggaccgc aaggaatcgg tcaatacact acatggcgtg atttcatatg      2820
cgcgattgct gatccccatg tgtatcactg gcaaactgtg atggacgaca ccgtcagtgc      2880
gtccgtcgcg caggctctcg atgagctgat gctttgggcc gaggactgcc ccgaagtccg      2940
gcacctcgtg cacgcggatt cggctccaa caatgtcctg acggacaatg gccgcataac      3000
agcggtcatt gactggagcg aggcgatgtt cggggattcc caatacgagg tcgccaacat      3060
cttcttctgg aggccgtggt tggcttgtat ggagcagcag acgcgctact cgagcggag      3120 gcatccggag cttgcaggat cgccgcggct ccgggcgtat atgctccgca ttggtcttga      3180
ccaactctat cagagcttgg ttgacggcaa tttcgatgat gcagcttggg cgcagggtcg      3240
atgcgacgca atcgtccgat ccggagccgg gactgtcggg cgtacacaaa tcgcccgcag      3300
aagcgcggcc gtctggaccg atggctgtgt agaagtactc gccgatagtg aaaccgacg      3360 ccccagcact cgtccgaggg caaggaata gtgaggtaca gcttggatcg atccggctgc      3420
taacaaagcc cgaaaggaag ctgagttggc tgctgccacc gctgagcaat aactagcata      3480 acccccttggg gcctctaaac gggtcttgag ggggttttttg ctgaaaggag gaactatatc      3540
cggatgatcg tcgaggcctc acgtgttaac aagcttgcat gcctgcaggt ttatcaacaa      3600
gtttgtacaa aaaagcaggc tccgaattcg cccttggaga acattattaa tgtgaaaatc      3660
atgcaaactt aaaaaaatca tcaacaacat aattttataa ttctaataaa atatttttt      3720 cttttaattc tttaatcaat gtctaacatt tatctattat ttatcacatt tgttatttaa      3780
tgtttctatc tttagagcta tcaaaaattt aaaatggtgg aaccttactc attgggttga      3840
gttcacctaa cttgtttaat aaatagatca atctaattct attcatctct tagtaagtat      3900
taaaaatgtt ggcccaactc tccatatatt ggtgagttat aggagtttac tcacttaaaa      3960
```

-continued

```
tgataataaa aatatttgtt ttaaaatcat tttttaaaca aaaaaataat gtttcagatt     4020
atttattctt agatcataac ttacaagcaa catttcaatg atcaattcaa ttgtcagaat     4080
caaaaccaat tgaaagagac aaatattcat gctaatcttc atcagaaact aaacattgac     4140
ataaagcaat agtattggaa ctacaagtta taattatgta ctttgtaata gtgtgaagaa     4200
aatcaaaata caaatagtaa tcatcatgat aaatgctatc tcaatttatt caattataaa     4260
aatatagaaa taaaatgtga taaatggata acatgtgtgc taatccagtc cactacgccc     4320
accacaagtt caacccaatg gactggatca tcttctttt ttcttactga tttctctctt      4380
cttccattct aatccatccc aaaagtagat gtttactatt tcccctttca tagtttcaca     4440
agtgtgcgca gaggccaaac tgaaagtggt agtacatggt gtaatattaa tcacagatgt     4500
gctctcatga agtctgaact tacagctcaa gtaacaacca acaagtaaaa agtacagaag     4560
atagcataaa aaatgaaggt agaacaaatt ccaagttttc tacatattac ggtgcataaa     4620
tcaaccacgt gaaggctcca tttatttgcc gctataacat tggtgaccct cttccacaaa     4680
tagtaagtaa taaaaccaag tacaaaaaaa tgttcaacta ccaagtgatc acaatcttca     4740
tgcatctgag tcacactatt gcccttttgct catgaagtac actttactca ccgccaaagt    4800
tcactcaaca ctgtagaaca aaggaatcat ataaataatg catatctctc ccttaagcct     4860
tcaacacata caaaagtgac acaccaaatc aaagacacct gagccattca attcccctcc    4920
tttattgctt tcaagtttca acactaattt tattatctga acaagggcg aattcgaccc     4980 agcttt                                                                4986

<210> SEQ ID NO 48
<211> LENGTH: 4792
<212> TYPE: DNA
<213> ORGANISM: Artificial
<220> FEATURE:
<223> OTHER INFORMATION: Nucleotide sequence of QC300-2Y

<400> SEQUENCE: 48
cttgtacaaa gtggttgatg ggatccatgg cccacagcaa gcacggcctg aaggaggaga       60
tgaccatgaa gtaccacatg gagggctgcg tgaacggcca caagttcgtg atcaccggcg      120
agggcatcgg ctaccccttc aagggcaagc agaccatcaa cctgtgcgtg atcgagggcg      180
gccccctgcc cttcagcgag gacatcctga gcgccggctt caagtacggc gaccggatct      240
tcaccgagta cccccaggac atcgtggact acttcaagaa cagctgcccc gccggctaca      300
cctggggccg gagcttcctg ttcgaggacg gcgccgtgtg catctgtaac gtggacatca      360
ccgtgagcgt gaaggagaac tgcatctacc acaagagcat cttcaacggc gtgaacttcc      420
ccgccgacgg ccccgtgatg aagaagatga ccaccaactg ggaggccagc tgcgagaaga      480
tcatgcccgt gcctaagcag ggcatcctga agggcgacgt gagcatgtac ctgctgctga      540
aggacggcgg ccggtaccgg tgccagttcg acaccgtgta caaggccaag agcgtgccca      600
gcaagatgcc cgagtggcac ttcatccagc acaagctgct gcgggaggac cggagcgacg      660
ccaagaacca gaagtggcag ctgaccgagc acgccatcgc cttccccagc gccctggcct      720
gagagctcga atttccccga tcgttcaaac atttggcaat aaagtttctt aagattgaat      780
cctgttgccg gtcttgcgat gattatcata aatttctgt tgaattacgt taagcatgta      840
ataattaaca tgtaatgcat gacgttattt atgagatggg ttttatgat tagagtcccg      900 caattataca tttaatacgc gatagaaaac aaaatatagc gcgcaaacta ggataaatta      960
```

```
tcgcgcgcgg tgtcatctat gttactagat cgggaattct agtggccggc ccagctgata   1020
tccatcacac tggcggccgc tcgagttcta tagtgtcacc taaatcgtat gtgtatgata   1080
cataaggtta tgtattaatt gtagccgcgt tctaacgaca atatgtccat atggtgcact   1140
ctcagtacaa tctgctctga tgccgcatag ttaagccagc cccgacaccc gccaacaccc   1200
gctgacgcgc cctgacgggc ttgtctgctc ccggcatccg cttacagaca agctgtgacc   1260
gtctccggga gctgcatgtg tcagaggttt tcaccgtcat caccgaaacg cgcgagacga   1320
aagggcctcg tgatacgcct attttatag gttaatgtca tgaccaaaat cccttaacgt    1380
gagttttcgt tccactgagc gtcagacccc gtagaaaaga tcaaaggatc ttcttgagat   1440 ccttttttc tgcgcgtaat ctgctgcttg caaacaaaaa aaccaccgct accagcggtg     1500
gtttgtttgc cggatcaaga gctaccaact cttttccga aggtaactgg cttcagcaga    1560
gcgcagatac caaatactgt ccttctagtg tagccgtagt taggccacca cttcaagaac   1620
tctgtagcac cgcctacata cctcgctctg ctaatcctgt taccagtggc tgctgccagt   1680
ggcgataagt cgtgtcttac cgggttggac tcaagacgat agttaccgga taaggcgcag   1740
cggtcgggct gaacggggg ttcgtgcaca cagcccagct tggagcgaac gacctacacc    1800
gaactgagat acctacagcg tgagcattga aaagcgccac gcttcccga agggagaaag    1860 gcggacaggt atccggtaag cggcagggtc ggaacaggag agcgcacgag ggagcttcca   1920
gggggaaacg cctggtatct ttatagtcct gtcgggtttc gccacctctg acttgagcgt   1980
cgatttttgt gatgctcgtc agggggcgg agcctatgga aaaacgccag caacgcggcc    2040 ttttttacggt tcctggcctt ttgctggcct tttgctcaca tgttctttcc tgcgttatcc   2100
cctgattctg tggataaccg tattaccgcc tttgagtgag ctgataccgc tcgccgcagc   2160
cgaacgaccg agcgcagcga gtcagtgagc gaggaagcgg aagagcgccc aatacgcaaa   2220
ccgcctctcc ccgcgcgttg gccgattcat taatgcaggt tgatcagatc tcgatcccgc   2280
gaaattaata cgactcacta tagggagacc acaacggttt ccctctagaa ataattttgt   2340
ttaactttaa gaaggagata tacccatgga aaagcctgaa ctcaccgcga cgtctgtcga   2400
gaagtttctg atcgaaaagt tcgacagcgt ctccgacctg atgcagctct cggagggcga   2460
agaatctcgt gctttcagct tcgatgtagg agggcgtgga tatgtcctgc gggtaaatag   2520
ctgcgccgat ggtttctaca agatcgtta tgtttatcgg cactttgcat cggccgcgct    2580
cccgattccg gaagtgcttg acattgggga attcagcgag agcctgacct attgcatctc   2640
ccgccgtgca cagggtgtca cgttgcaaga cctgcctgaa accgaactgc ccgctgttct   2700
gcagccggtc gcggaggcta tggatgcgat cgctgcggcc gatcttagcc agacgagcgg   2760
gttcggccca ttcggaccgc aaggaatcgg tcaatacact acatggcgtg atttcatatg   2820
cgcgattgct gatccccatg tgtatcactg gcaaactgtg atggacgaca ccgtcagtgc   2880
gtccgtcgcg caggctctcg atgagctgat gctttgggcc gaggactgcc ccgaagtccg   2940
gcacctcgtg cacgcggatt tcggctccaa caatgtcctg acggacaatg gccgcataac   3000
agcggtcatt gactggagcg aggcgatgtt cggggattcc caatacgagg tcgccaacat   3060
cttcttctgg aggccgtggt tggcttgtat ggagcagcag acgcgctact cgagcggag    3120 gcatccggag cttgcaggat cgccgcggct ccgggcgtat atgctccgca ttggtcttga   3180
ccaactctat cagagcttgg ttgacggcaa tttcgatgat gcagcttggg cgcagggtcg   3240
atgcgacgca atcgtccgat ccggagccgg gactgtcggg cgtacacaaa tcgcccgcag   3300
aagcgcggcc gtctggaccg atggctgtgt agaagtactc gccgatagtg gaaaccgacg   3360
```

| | |
|---|---|
| ccccagcact cgtccgaggg caaaggaata gtgaggtaca gcttggatcg atccggctgc | 3420 |
| taacaaagcc cgaaaggaag ctgagttggc tgctgccacc gctgagcaat aactagcata | 3480 |
| accccttggg gcctctaaac gggtcttgag gggttttttg ctgaaaggag gaactatatc | 3540 |
| cggatgatcg tcgaggcctc acgtgttaac aagcttgcat gcctgcaggt ttatcaacaa | 3600 |
| gtttgtacaa aaaagcaggc tccgaattcg cccttcattg ggttgagttc acctaacttg | 3660 |
| tttaataaat agatcaatct aattctattc atctcttagt aagtattaaa atgttggcc | 3720 |
| caactctcca tatattggtg agttatagga gtttactcac ttaaaatgat aataaaaata | 3780 |
| tttgttttaa aatcattttt taaacaaaaa aataatgttt cagattattt attcttagat | 3840 |
| cataacttac aagcaacatt tcaatgatca attcaattgt cagaatcaaa accaattgaa | 3900 |
| agagacaaat attcatgcta atcttcatca gaaactaaac attgacataa agcaatagta | 3960 |
| ttggaactac aagttataat tatgtacttt gtaatagtgt gaagaaaatc aaaatacaaa | 4020 |
| tagtaatcat catgataaat gctatctcaa tttattcaat tataaaaata tagaaataaa | 4080 |
| atgtgataaa tggataacat gtgtgctaat ccagtccact acgcccacca caagttcaac | 4140 |
| ccaatggact ggatcatctt cttttttttct tactgatttc tctcttcttc cattctaatc | 4200 |
| catcccaaaa gtagatgttt actatttccc ctttcatagt ttcacaagtg tgcgcagagg | 4260 |
| ccaaactgaa agtggtagta catggtgtaa tattaatcac agatgtgctc tcatgaagtc | 4320 |
| tgaacttaca gctcaagtaa caaccaacaa gtaaaaagta cagaagatag cataaaaaat | 4380 |
| gaaggtagaa caaattccaa gttttctaca tattacggtg cataaatcaa ccacgtgaag | 4440 |
| gctccattta tttgccgcta taacattggt gaccctcttc cacaaatagt aagtaataaa | 4500 |
| accaagtaca aaaaaatgtt caactaccaa gtgatcacaa tcttcatgca tctgagtcac | 4560 |
| actattgccc tttgctcatg aagtacactt tactcaccgc caaagttcac tcaacactgt | 4620 |
| agaacaaagg aatcatataa ataatgcata tctctccctt aagccttcaa cacatacaaa | 4680 |
| agtgacacac caaatcaaag acacctgagc cattcaattc ccctccttta ttgctttcaa | 4740 |
| gtttcaacac taattttatt atctgaaaca agggcgaatt cgacccagct tt | 4792 |

<210> SEQ ID NO 49
<211> LENGTH: 4590
<212> TYPE: DNA
<213> ORGANISM: Artificial
<220> FEATURE:
<223> OTHER INFORMATION: Nucleotide sequence of QC300-3Y

<400> SEQUENCE: 49

| | |
|---|---|
| cttgtacaaa gtggttgatg ggatccatgg cccacagcaa gcacggcctg aaggaggaga | 60 |
| tgaccatgaa gtaccacatg gagggctgcg tgaacggcca cagttcgtg atcaccggcg | 120 |
| agggcatcgg ctacccttc aagggcaagc agaccatcaa cctgtgcgtg atcgagggcg | 180 |
| gcccctgcc cttcagcgag gacatcctga gcgccggctt caagtacggc gaccggatct | 240 |
| tcaccgagta cccccaggac atcgtggact acttcaagaa cagctgcccc gccggctaca | 300 |
| cctggggccg gagcttcctg ttcgaggacg gcgccgtgtg catctgtaac gtggacatca | 360 |
| ccgtgagcgt gaaggagaac tgcatctacc acaagagcat cttcaacggc gtgaacttcc | 420 |
| ccgccgacgg ccccgtgatg aagaagatga ccaccaactg ggaggccagc tgcgagaaga | 480 |
| tcatgcccgt gcctaagcag ggcatcctga agggcgacgt gagcatgtac ctgctgctga | 540 |
| aggacggcgg ccggtaccgg tgccagttcg acaccgtgta caaggccaag agcgtgccca | 600 |

```
gcaagatgcc cgagtggcac ttcatccagc acaagctgct gcgggaggac cggagcgacg    660
ccaagaacca gaagtggcag ctgaccgagc acgccatcgc cttccccagc gccctggcct    720
gagagctcga atttccccga tcgttcaaac atttggcaat aaagtttctt aagattgaat    780
cctgttgccg gtcttgcgat gattatcata taatttctgt tgaattacgt taagcatgta    840
ataattaaca tgtaatgcat gacgttattt atgagatggg ttttatgat tagagtcccg    900 caattataca tttaatacgc gatagaaaac aaaatatagc gcgcaaacta ggataaatta    960
tcgcgcgcgg tgtcatctat gttactagat cgggaattct agtggccggc ccagctgata   1020
tccatcacac tggcggccgc tcgagttcta tagtgtcacc taaatcgtat gtgtatgata   1080
cataaggtta tgtattaatt gtagccgcgt tctaacgaca atatgtccat atggtgcact   1140
ctcagtacaa tctgctctga tgccgcatag ttaagccagc cccgacaccc gccaacaccc   1200
gctgacgcgc cctgacgggc ttgtctgctc ccggcatccg cttacagaca agctgtgacc   1260
gtctccggga gctgcatgtg tcagaggttt tcaccgtcat caccgaaacg cgcgagacga   1320
aagggcctcg tgatacgcct atttttatag gttaatgtca tgaccaaaat cccttaacgt   1380
gagttttcgt tccactgagc gtcagacccc gtagaaaaga tcaaaggatc ttcttgagat   1440
cctttttttc tgcgcgtaat ctgctgcttg caaacaaaaa aaccaccgct accagcggtg   1500
gtttgtttgc cggatcaaga gctaccaact ctttttccga aggtaactgg cttcagcaga   1560
gcgcagatac caaatactgt ccttctagtg tagccgtagt taggccacca cttcaagaac   1620
tctgtagcac cgcctacata cctcgctctg ctaatcctgt taccagtggc tgctgccagt   1680
ggcgataagt cgtgtcttac cgggttggac tcaagacgat agttaccgga taaggcgcag   1740
cggtcgggct gaacgggggg ttcgtgcaca gcccagct tggagcgaac gacctacacc    1800
gaactgagat acctacagcg tgagcattga aaagcgcca cgcttcccga agggagaaag    1860
gcggacaggt atccggtaag cggcagggtc ggaacaggag agcgcacgag ggagcttcca    1920
gggggaaacg cctggtatct ttatagtcct gtcgggtttc gccacctctg acttgagcgt    1980
cgatttttgt gatgctcgtc aggggggcgg agcctatgga aaaacgccag caacgcggcc    2040 ttttacggt tcctggcctt tgctggcct tttgctcaca tgttctttcc tgcgttatcc    2100
cctgattctg tggataaccg tattaccgcc tttgagtgag ctgataccgc tcgccgcagc    2160
cgaacgaccg agcgcagcga gtcagtgagc gaggaagcgg aagagcgccc aatacgcaaa    2220
ccgcctctcc ccgcgcgttg gccgattcat taatgcaggt tgatcagatc tcgatcccgc    2280
gaaattaata cgactcacta tagggagacc acaacggttt ccctctagaa ataattttgt    2340
ttaactttaa gaaggagata tacccatgga aaagcctgaa ctcaccgcga cgtctgtcga    2400
gaagtttctg atcgaaaagt tcgacagcgt ctccgacctg atgcagctct cggagggcga    2460
agaatctcgt gctttcagct tcgatgtagg agggcgtgga tatgtcctgc gggtaaatag    2520
ctgcgccgat ggtttctaca agatcgtta tgtttatcgg cactttgcat cggccgcgct    2580
cccgattccg gaagtgcttg acattgggga attcagcgag agcctgacct attgcatctc    2640
ccgccgtgca cagggtgtca cgttgcaaga cctgcctgaa accgaactgc ccgctgttct    2700
gcagccggtc gcggaggcta tggatgcgat cgctgcggcc gatcttagcc agacgagcgg    2760
gttcggccca ttcggaccgc aaggaatcgg tcaatacact acatggcgtg atttcatatg    2820
cgcgattgct gatccccatg tgtatcactg gcaaactgtg atggacgaca ccgtcagtgc    2880
gtccgtcgcg caggctctcg atgagctgat gctttgggcc gaggactgcc ccgaagtccg    2940
gcacctcgtg cacgcggatt tcggctccaa caatgtcctg acggacaatg gccgcataac    3000
```

| | |
|---|---|
| agcggtcatt gactggagcg aggcgatgtt cggggattcc caatacgagg tcgccaacat | 3060 |
| cttcttctgg aggccgtggt tggcttgtat ggagcagcag acgcgctact tcgagcggag | 3120 |
| gcatccggag cttgcaggat cgccgcggct ccgggcgtat atgctccgca ttggtcttga | 3180 |
| ccaactctat cagagcttgg ttgacggcaa tttcgatgat gcagcttggg cgcagggtcg | 3240 |
| atgcgacgca atcgtccgat ccggagccgg gactgtcggg cgtacacaaa tcgcccgcag | 3300 |
| aagcgcggcc gtctggaccg atggctgtgt agaagtactc gccgatagtg gaaaccgacg | 3360 |
| ccccagcact cgtccgaggg caaaggaata gtgaggtaca gcttggatcg atccggctgc | 3420 |
| taacaaagcc cgaaaggaag ctgagttggc tgctgccacc gctgagcaat aactagcata | 3480 |
| acccccttggg gcctctaaac gggtcttgag gggttttttg ctgaaaggag aactatatc | 3540 |
| cggatgatcg tcgaggcctc acgtgttaac aagcttgcat gcctgcaggt ttatcaacaa | 3600 |
| gtttgtacaa aaaagcaggc tccgaattcg cccttgatca taacttacaa gcaacatttc | 3660 |
| aatgatcaat tcaattgtca gaatcaaaac caattgaaag agacaaatat tcatgctaat | 3720 |
| cttcatcaga aactaaacat tgacataaag caatagtatt ggaactacaa gttataatta | 3780 |
| tgtactttgt aatagtgtga agaaaatcaa aatacaaata gtaatcatca tgataaatgc | 3840 |
| tatctcaatt tattcaatta taaaaatata gaaataaaat gtgataaatg gataacatgt | 3900 |
| gtgctaatcc agtccactac gcccaccaca agttcaaccc aatggactgg atcatcttct | 3960 |
| ttttttctta ctgatttctc tcttcttcca ttctaatcca tcccaaaagt agatgtttac | 4020 |
| tatttcccct ttcatagttt cacaagtgtg cgcagaggcc aaactgaaag tggtagtaca | 4080 |
| tggtgtaata ttaatcacag atgtgctctc atgaagtctg aacttacagc tcaagtaaca | 4140 |
| accaacaagt aaaagtaca gaagatagca taaaaatga aggtagaaca aattccaagt | 4200 |
| tttctacata ttacggtgca taaatcaacc acgtgaaggc tccatttatt tgccgctata | 4260 |
| acattggtga ccctcttcca caaatagtaa gtaataaaac caagtacaaa aaatgttca | 4320 |
| actaccaagt gatcacaatc ttcatgcatc tgagtcacac tattgcccctt tgctcatgaa | 4380 |
| gtacacttta ctcaccgcca aagttcactc aacactgtag aacaaaggaa tcatataaat | 4440 |
| aatgcatatc tctcccttaa gccttcaaca catacaaaag tgacacacca aatcaaagac | 4500 |
| acctgagcca ttcaattccc ctcctttatt gctttcaagt ttcaacacta atttttattat | 4560 |
| ctgaaacaag ggcgaattcg acccagcttt | 4590 |

<210> SEQ ID NO 50
<211> LENGTH: 4343
<212> TYPE: DNA
<213> ORGANISM: Artificial
<220> FEATURE:
<223> OTHER INFORMATION: Nucleotide sequence of QC300-4Y

<400> SEQUENCE: 50

| | |
|---|---|
| cttgtacaaa gtggttgatg ggatccatgg cccacagcaa gcacggcctg aaggaggaga | 60 |
| tgaccatgaa gtaccacatg gagggctgcg tgaacggcca caagttcgtg atcaccggcg | 120 |
| agggcatcgg ctaccccttc aagggcaagc agaccatcaa cctgtgcgtg atcgagggcg | 180 |
| gccccctgcc cttcagcgag gacatcctga gcgccggctt caagtacggc gaccggatct | 240 |
| tcaccgagta ccccccaggac atcgtggact acttcaagaa cagctgcccc gccggctaca | 300 |
| cctggggccg gagcttcctg ttcgaggacg gcgccgtgtg catctgtaac gtggacatca | 360 |
| ccgtgagcgt gaaggagaac tgcatctacc acaagagcat cttcaacggc gtgaacttcc | 420 |

```
ccgccgacgg ccccgtgatg aagaagatga ccaccaactg ggaggccagc tgcgagaaga    480
tcatgcccgt gcctaagcag ggcatcctga agggcgacgt gagcatgtac ctgctgctga    540
aggacggcgg ccggtaccgg tgccagttcg acaccgtgta caaggccaag agcgtgccca    600
gcaagatgcc cgagtggcac ttcatccagc acaagctgct gcgggaggac cggagcgacg    660
ccaagaacca gaagtggcag ctgaccgagc acgccatcgc cttccccagc gccctggcct    720
gagagctcga atttccccga tcgttcaaac atttggcaat aaagtttctt aagattgaat    780
cctgttgccg gtcttgcgat gattatcata taatttctgt tgaattacgt taagcatgta    840
ataattaaca tgtaatgcat gacgttattt atgagatggg ttttatgat tagagtcccg     900 caattataca tttaatacgc gatagaaaac aaaatatagc gcgcaaacta ggataaatta    960
tcgcgcgcgg tgtcatctat gttactagat cgggaattct agtggccggc ccagctgata   1020
tccatcacac tggcggccgc tcgagttcta tagtgtcacc taaatcgtat gtgtatgata   1080
cataaggtta tgtattaatt gtagccgcgt tctaacgaca atatgtccat atggtgcact   1140
ctcagtacaa tctgctctga tgccgcatag ttaagccagc cccgacaccc gccaacaccc   1200
gctgacgcgc cctgacgggc ttgtctgctc ccggcatccg cttacagaca agctgtgacc   1260
gtctccggga gctgcatgtg tcagaggttt tcaccgtcat caccgaaacg cgcgagacga   1320
aagggcctcg tgatacgcct atttttatag gttaatgtca tgaccaaaat cccttaacgt   1380
gagttttcgt tccactgagc gtcagacccc gtagaaaaga tcaaaggatc ttcttgagat   1440
cctttttttc tgcgcgtaat ctgctgcttg caaacaaaaa aaccaccgct accagcggtg   1500
gtttgtttgc cggatcaaga gctaccaact cttttccga aggtaactgg cttcagcaga    1560
gcgcagatac caaatactgt ccttctagtg tagccgtagt taggccacca cttcaagaac   1620
tctgtagcac cgcctacata cctcgctctg ctaatcctgt taccagtggc tgctgccagt   1680
ggcgataagt cgtgtcttac cgggttggac tcaagacgat agttaccgga taaggcgcag   1740
cggtcgggct gaacggggg ttcgtgcaca cagcccagct tggagcgaac gacctacacc    1800
gaactgagat acctacagcg tgagcattga aaagcgcca cgcttcccga agggagaaag    1860
gcggacaggt atccggtaag cggcagggtc ggaacaggag agcgcacgag ggagcttcca   1920
gggggaaacg cctggtatct ttatagtcct gtcgggtttc gccacctctg acttgagcgt   1980
cgatttttgt gatgctcgtc aggggggcgg agcctatgga aaaacgccag caacgcggcc   2040 ttttacggt tcctggcctt tgctggcct tttgctcaca tgttctttcc tgcgttatcc      2100
cctgattctg tggataaccg tattaccgcc tttgagtgag ctgataccgc tcgccgcagc   2160
cgaacgaccg agcgcagcga gtcagtgagc gaggaagcgg aagagcgccc aatacgcaaa   2220
ccgcctctcc ccgcgcgttg gccgattcat taatgcaggt tgatcagatc tcgatcccgc   2280
gaaattaata cgactcacta tagggagacc acaacggttt ccctctagaa ataattttgt   2340
ttaactttaa gaaggagata tacccatgga aaagcctgaa ctcaccgcga cgtctgtcga   2400
gaagtttctg atcgaaaagt tcgacagcgt ctccgacctg atgcagctct cggagggcga   2460
agaatctcgt gctttcagct tcgatgtagg agggcgtgga tatgtcctgc gggtaaatag   2520
ctgcgccgat ggtttctaca agatcgtta tgtttatcgg cactttgcat cggccgcgct    2580
cccgattccg gaagtgcttg acattgggga attcagcgag agcctgacct attgcatctc   2640
ccgccgtgca cagggtgtca cgttgcaaga cctgcctgaa accgaactgc ccgctgttct   2700
gcagccggtc gcggaggcta tggatgcgat cgctgcggcc gatcttagcc agacgagcgg   2760
gttcggccca ttcggaccgc aaggaatcgg tcaatacact acatggcgtg atttcatatg   2820
```

```
cgcgattgct gatccccatg tgtatcactg gcaaactgtg atggacgaca ccgtcagtgc    2880
gtccgtcgcg caggctctcg atgagctgat gctttgggcc gaggactgcc ccgaagtccg    2940
gcacctcgtg cacgcggatt tcggctccaa caatgtcctg acggacaatg gccgcataac    3000
agcggtcatt gactggagcg aggcgatgtt cggggattcc caatacgagg tcgccaacat    3060
cttcttctgg aggccgtggt tggcttgtat ggagcagcag acgcgctact tcgagcggag    3120
gcatccggag cttgcaggat cgccgcggct ccgggcgtat atgctccgca ttggtcttga    3180
ccaactctat cagagcttgg ttgacggcaa tttcgatgat gcagcttggg cgcagggtcg    3240
atgcgacgca atcgtccgat ccggagccgg gactgtcggg cgtacacaaa tcgcccgcag    3300
aagcgcggcc gtctggaccg atggctgtgt agaagtactc gccgatagtg aaaccgacg    3360 ccccagcact cgtccgaggg caaaggaata gtgaggtaca gcttggatcg atccggctgc    3420
taacaaagcc cgaaaggaag ctgagttggc tgctgccacc gctgagcaat aactagcata    3480
accccttggg gcctctaaac gggtcttgag gggttttttg ctgaaaggag gaactatatc    3540
cggatgatcg tcgaggcctc acgtgttaac aagcttgcat gcctgcaggt ttatcaacaa    3600
gtttgtacaa aaaagcaggc tccgaattcg cccttgataa atggataaca tgtgtgctaa    3660
tccagtccac tacgcccacc acaagttcaa cccaatggac tggatcatct tctttttttc    3720
ttactgattt ctctcttctt ccattctaat ccatcccaaa agtagatgtt tactatttcc    3780
cctttcatag tttcacaagt gtgcgcagag gccaaactga agtggtagt acatggtgta    3840 atattaatca cagatgtgct ctcatgaagt ctgaacttac agctcaagta acaaccaaca    3900
agtaaaaagt acagaagata gcataaaaaa tgaaggtaga acaaattcca agttttctac    3960
atattacggt gcataaatca accacgtgaa ggctccattt atttgccgct ataacattgg    4020
tgaccctctt ccacaaatag taagtaataa aaccaagtac aaaaaaatgt tcaactacca    4080
agtgatcaca atcttcatgc atctgagtca cactattgcc ctttgctcat gaagtacact    4140
ttactcaccg ccaaagttca ctcaacactg tagaacaaag gaatcatata aataatgcat    4200
atctctccct taagccttca acacataca aagtgcacaca ccaaatcaaa gacacctgag    4260
ccattcaatt cccctccttt attgctttca agtttcaaca ctaattttat tatctgaaac    4320
aagggcgaat tcgacccagc ttt                                           4343
```

<210> SEQ ID NO 51
<211> LENGTH: 4130
<212> TYPE: DNA
<213> ORGANISM: Artificial
<220> FEATURE:
<223> OTHER INFORMATION: Nucleotide sequence of QC300-5Y

<400> SEQUENCE: 51

```
cttgtacaaa gtggttgatg ggatccatgg cccacagcaa gcacggcctg aaggaggaga     60
tgaccatgaa gtaccacatg gagggctgcg tgaacggcca caagttcgtg atcaccggcg    120
agggcatcgg ctaccccttc aagggcaagc agaccatcaa cctgtgcgtg atcgagggcg    180 gcccctgcc cttcagcgag gacatcctga gcgccggctt caagtacggc gaccggatct    240
tcaccgagta cccccaggac atcgtggact acttcaagaa cagctgcccc gccggctaca    300
cctggggccg gagcttcctg ttcgaggacg gcgccgtgtg catctgtaac gtggacatca    360
ccgtgagcgt gaaggagaac tgcatctacc acaagagcat cttcaacggc gtgaacttcc    420
ccgccgacgg cccccgtgatg aagaagatga ccaccaactg ggaggccagc tgcgagaaga    480
```

```
tcatgcccgt gcctaagcag ggcatcctga agggcgacgt gagcatgtac ctgctgctga      540
aggacggcgg ccggtaccgg tgccagttcg acaccgtgta caaggccaag agcgtgccca      600
gcaagatgcc cgagtggcac ttcatccagc acaagctgct gcgggaggac cggagcgacg      660
ccaagaacca gaagtggcag ctgaccgagc acgccatcgc cttccccagc gccctggcct      720
gagagctcga atttccccga tcgttcaaac atttggcaat aaagtttctt aagattgaat      780
cctgttgccg gtcttgcgat gattatcata taatttctgt tgaattacgt taagcatgta      840
ataattaaca tgtaatgcat gacgttattt atgagatggg ttttttatgat tagagtcccg      900 caattataca tttaatacgc gatagaaaac aaaatatagc gcgcaaacta ggataaatta      960
tcgcgcgcgg tgtcatctat gttactagat cgggaattct agtggccggc ccagctgata     1020
tccatcacac tggcggccgc tcgagttcta tagtgtcacc taaatcgtat gtgtatgata     1080
cataaggtta tgtattaatt gtagccgcgt tctaacgaca atatgtccat atggtgcact     1140
ctcagtacaa tctgctctga tgccgcatag ttaagccagc cccgacaccc gccaacaccc     1200
gctgacgcgc cctgacgggc ttgtctgctc ccggcatccg cttacagaca agctgtgacc     1260
gtctccggga gctgcatgtg tcagaggttt tcaccgtcat caccgaaacg cgcgagacga     1320
aagggcctcg tgatacgcct atttttatag gttaatgtca tgaccaaaat cccttaacgt     1380
gagttttcgt tccactgagc gtcagacccc gtagaaaaga tcaaaggatc ttcttgagat     1440
cctttttttc tgcgcgtaat ctgctgcttg caaacaaaaa aaccaccgct accagcggtg     1500
gtttgtttgc cggatcaaga gctaccaact ctttttccga aggtaactgg cttcagcaga     1560
gcgcagatac caaatactgt ccttctagtg tagccgtagt taggccacca cttcaagaac     1620
tctgtagcac cgcctacata cctcgctctg ctaatcctgt taccagtggc tgctgccagt     1680
ggcgataagt cgtgtcttac cgggttggac tcaagacgat agttaccgga taaggcgcag     1740
cggtcgggct gaacggggg ttcgtgcaca cagcccagct tggagcgaac gacctacacc     1800
gaactgagat acctacagcg tgagcattga gaaagcgcca cgcttcccga agggagaaag     1860
gcggacaggt atccggtaag cggcagggtc ggaacaggag agcgcacgag ggagcttcca     1920
gggggaaacg cctggtatct ttatagtcct gtcgggtttc gccacctctg acttgagcgt     1980
cgatttttgt gatgctcgtc aggggggcgg agcctatgga aaaacgccag caacgcggcc     2040
tttttacggt tcctggcctt ttgctggcct tttgctcaca tgttctttcc tgcgttatcc     2100
cctgattctg tggataaccg tattaccgcc tttgagtgag ctgataccgc tcgccgcagc     2160
cgaacgaccg agcgcagcga gtcagtgagc gaggaagcgg aagagcgccc aatacgcaaa     2220
ccgcctctcc ccgcgcgttg gccgattcat taatgcaggt tgatcagatc tcgatcccgc     2280
gaaattaata cgactcacta tagggagacc acaacggttt ccctctagaa ataattttgt     2340
ttaactttaa gaaggagata tacccatgga aaagcctgaa ctcaccgcga cgtctgtcga     2400
gaagtttctg atcgaaaagt tcgacagcgt ctccgacctg atgcagctct cggagggcga     2460
agaatctcgt gctttcagct tcgatgtagg agggcgtgga tatgtcctgc gggtaaatag     2520
ctgcgccgat ggtttctaca agatcgtta tgtttatcgg cactttgcat cggccgcgct     2580
cccgattccg gaagtgcttg acattgggga attcagcgag agcctgacct attgcatctc     2640
ccgccgtgca cagggtgtca cgttgcaaga cctgcctgaa accgaactgc cgctgttcct     2700
gcagccggtc gcggaggcta tggatgcgat cgctgcggcc gatcttagcc agacgagcgg     2760
gttcggccca ttcggaccgc aaggaatcgg tcaatacact acatggcgtg atttcatatg     2820
cgcgattgct gatccccatg tgtatcactg gcaaactgtg atggacgaca ccgtcagtgc     2880
```

| | |
|---|---|
| gtccgtcgcg caggctctcg atgagctgat gctttgggcc gaggactgcc ccgaagtccg | 2940 |
| gcacctcgtg cacgcggatt tcggctccaa caatgtcctg acggacaatg gccgcataac | 3000 |
| agcggtcatt gactggagcg aggcgatgtt cggggattcc caatacgagg tcgccaacat | 3060 |
| cttcttctgg aggccgtggt tggcttgtat ggagcagcag acgcgctact tcgagcggag | 3120 |
| gcatccggag cttgcaggat cgccgcggct ccgggcgtat atgctccgca ttggtcttga | 3180 |
| ccaactctat cagagcttgg ttgacggcaa tttcgatgat gcagcttggg cgcagggtcg | 3240 |
| atgcgacgca atcgtccgat ccggagccgg gactgtcggg cgtacacaaa tcgcccgcag | 3300 |
| aagcgcggcc gtctggaccg atggctgtgt agaagtactc gccgatagtg gaaaccgacg | 3360 |
| ccccagcact cgtccgaggg caaaggaata gtgaggtaca gcttggatcg atccggctgc | 3420 |
| taacaaagcc cgaaaggaag ctgagttggc tgctgccacc gctgagcaat aactagcata | 3480 |
| accccttggg gcctctaaac gggtcttgag gggttttttg ctgaaaggag gaactatatc | 3540 |
| cggatgatcg tcgaggcctc acgtgttaac aagcttgcat gcctgcaggt ttatcaacaa | 3600 |
| gtttgtacaa aaaagcaggc tccgaattcg cccttcacag atgtgctctc atgaagtctg | 3660 |
| aacttacagc tcaagtaaca accaacaagt aaaaagtaca aagatagca taaaaaatga | 3720 |
| aggtagaaca aattccaagt tttctacata ttacggtgca taaatcaacc acgtgaaggc | 3780 |
| tccatttatt tgccgctata acattggtga ccctcttcca caaatagtaa gtaataaaac | 3840 |
| caagtacaaa aaaatgttca actaccaagt gatcacaatc ttcatgcatc tgagtcacac | 3900 |
| tattgcccctt tgctcatgaa gtacacttta ctcaccgcca aagttcactc aacactgtag | 3960 |
| aacaaaggaa tcatataaat aatgcatatc tctcccttaa gccttcaaca catacaaaag | 4020 |
| tgacacacca aatcaaagac acctgagcca ttcaattccc ctcctttatt gctttcaagt | 4080 |
| ttcaacacta attttattat ctgaaacaag ggcgaattcg acccagcttt | 4130 |

<210> SEQ ID NO 52
<211> LENGTH: 3895
<212> TYPE: DNA
<213> ORGANISM: Artificial
<220> FEATURE:
<223> OTHER INFORMATION: Nucleotide sequence of QC300-6Y

<400> SEQUENCE: 52

| | |
|---|---|
| cttgtacaaa gtggttgatg ggatccatgg cccacagcaa gcacggcctg aaggaggaga | 60 |
| tgaccatgaa gtaccacatg gagggctgcg tgaacggcca caagttcgtg atcaccggcg | 120 |
| agggcatcgg ctacccccttc aagggcaagc agaccatcaa cctgtgcgtg atcgagggcg | 180 |
| gcccccctgcc cttcagcgag gacatcctga gcgccggctt caagtacggc gaccggatct | 240 |
| tcaccgagta ccccccaggac atcgtggact acttcaagaa cagctgcccc gccggctaca | 300 |
| cctggggccg gagcttcctg ttcgaggacg gcgccgtgtg catctgtaac gtggacatca | 360 |
| ccgtgagcgt gaaggagaac tgcatctacc acaagcat cttcaacggc gtgaacttcc | 420 |
| ccgccgacgg cccccgtgatg aagaagatga ccaccaactg ggaggccagc tgcgagaaga | 480 |
| tcatgccccgt gcctaagcag ggcatcctga agggcgacgt gagcatgtac ctgctgctga | 540 |
| aggacggcgc ccggtaccgg tgccagttcg acaccgtgta caaggccaag agcgtgccca | 600 |
| gcaagatgcc cgagtggcac ttcatccagc acaagctgct gcgggaggac cggagcgacg | 660 |
| ccaagaacca gaagtggcag ctgaccgagc acgccatcgc cttccccagc gccctggcct | 720 |
| gagagctcga atttccccga tcgttcaaac atttggcaat aaagtttctt aagattgaat | 780 |

```
cctgttgccg gtcttgcgat gattatcata taatttctgt tgaattacgt taagcatgta    840
ataattaaca tgtaatgcat gacgttattt atgagatggg ttttatgat tagagtcccg      900 caattataca tttaatacgc gatagaaaac aaaatatagc gcgcaaacta ggataaatta    960
tcgcgcgcgg tgtcatctat gttactagat cgggaattct agtggccggc ccagctgata   1020
tccatcacac tggcggccgc tcgagttcta tagtgtcacc taaatcgtat gtgtatgata   1080
cataaggtta tgtattaatt gtagccgcgt tctaacgaca atatgtccat atggtgcact   1140
ctcagtacaa tctgctctga tgccgcatag ttaagccagc cccgacaccc gccaacaccc   1200
gctgacgcgc cctgacgggc ttgtctgctc ccggcatccg cttacagaca gctgtgacc    1260 gtctccggga gctgcatgtg tcagaggttt tcaccgtcat caccgaaacg cgcgagacga   1320
aagggcctcg tgatacgcct attttatag gttaatgtca tgaccaaaat cccttaacgt    1380
gagttttcgt tccactgagc gtcagacccc gtagaaaaga tcaaaggatc ttcttgagat   1440
cctttttttc tgcgcgtaat ctgctgcttg caaacaaaaa aaccaccgct accagcggtg   1500
gtttgtttgc cggatcaaga gctaccaact cttttccga aggtaactgg cttcagcaga    1560
gcgcagatac caaatactgt ccttctagtg tagccgtagt taggccacca cttcaagaac   1620
tctgtagcac cgcctacata cctcgctctg ctaatcctgt taccagtggc tgctgccagt   1680
ggcgataagt cgtgtcttac cgggttggac tcaagacgat agttaccgga taaggcgcag   1740
cggtcgggct gaacgggggg ttcgtgcaca gcccagct tggagcgaac gacctacacc     1800
gaactgagat acctacagcg tgagcattga aaagcgcca cgcttcccga agggagaaag    1860
gcggacaggt atccggtaag cggcagggtc ggaacaggag agcgcacgag ggagcttcca   1920
gggggaaacg cctggtatct ttatagtcct gtcgggttc gccacctctg acttgagcgt    1980
cgatttttgt gatgctcgtc aggggggcgg agcctatgga aaaacgccag caacgcggcc   2040 ttttacggt tcctggcctt ttgctggcct tttgctcaca tgttctttcc tgcgttatcc     2100
cctgattctg tggataaccg tattaccgcc tttgagtgag ctgataccgc tcgccgcagc   2160
cgaacgaccg agcgcagcga gtcagtgagc gaggaagcgg aagagcgccc aatacgcaaa   2220
ccgcctctcc ccgcgcgttg gccgattcat taatgcaggt tgatcagatc tcgatcccgc   2280
gaaattaata cgactcacta tagggagacc acaacggttt ccctctagaa ataattttgt   2340
ttaactttaa gaaggagata tacccatgga aaagcctgaa ctcaccgcga cgtctgtcga   2400
gaagtttctg atcgaaaagt tcgacagcgt ctccgacctg atgcagctct cggagggcga   2460
agaatctcgt gctttcagct tcgatgtagg agggcgtgga tatgtcctgc gggtaaatag   2520
ctgcgccgat ggtttctaca agatcgtta tgtttatcgg cactttgcat cggccgcgct    2580
cccgattccg gaagtgcttg acattgggga attcagcgag agcctgacct attgcatctc   2640
ccgccgtgca cagggtgtca cgttgcaaga cctgcctgaa accgaactgc ccgctgttct   2700
gcagccggtc gcggaggcta tggatgcgat cgctgcggcc gatcttagcc agacgagcgg   2760
gttcggccca ttcggaccgc aaggaatcgg tcaatacact acatggcgtg atttcatatg   2820
cgcgattgct gatccccatg tgtatcactg gcaaactgtg atggacgaca ccgtcagtgc   2880
gtccgtcgcg caggctctcg atgagctgat gctttgggcc gaggactgcc ccgaagtccg   2940
gcacctcgtg cacgcggatt tcggctccaa caatgtcctg acggacaatg ccgcataac    3000 agcggtcatt gactgagcg aggcgatgtt cggggattcc caatacgagg tcgccaacat   3060
cttcttctgg aggccgtggt tggcttgtat ggagcagcag acgcgctact tcgagcggag   3120
gcatccggag cttgcaggat cgccgcggct ccgggcgtat atgctccgca ttggtcttga   3180
```

```
ccaactctat cagagcttgg ttgacggcaa tttcgatgat gcagcttggg cgcagggtcg      3240
atgcgacgca atcgtccgat ccggagccgg gactgtcggg cgtacacaaa tcgcccgca      3300 aagcgcggcc gtctggaccg atggctgtgt agaagtactc gccgatagtg gaaaccgacg      3360
ccccagcact cgtccgaggg caaaggaata gtgaggtaca gcttggatcg atccggctgc      3420
taacaaagcc cgaaaggaag ctgagttggc tgctgccacc gctgagcaat aactagcata      3480
accccttggg gcctctaaac gggtcttgag gggttttttg ctgaaaggag gaactatatc      3540
cggatgatcg tcgaggcctc acgtgttaac aagcttgcat gcctgcaggt ttatcaacaa      3600
gtttgtacaa aaaagcaggc tccgaattcg cccttgatca caatcttcat gcatctgagt      3660
cacactattg ccctttgctc atgaagtaca ctttactcac cgccaaagtt cactcaacac      3720
tgtagaacaa aggaatcata taaataatgc atatctctcc cttaagcctt caacacatac      3780
aaaagtgaca caccaaatca aagacacctg agccattcaa ttcccctcct ttattgcttt      3840
caagtttcaa cactaatttt attatctgaa acaagggcga attcgaccca gcttt          3895
```

<210> SEQ ID NO 53  
<211> LENGTH: 4157  
<212> TYPE: DNA  
<213> ORGANISM: Artificial  
<220> FEATURE:  
<223> OTHER INFORMATION: Nucleotide sequence of pZSL90

<400> SEQUENCE: 53

```
gatccatggc ccacagcaag cacggcctga aggaggagat gaccatgaag taccacatgg        60
agggctgcgt gaacggccac aagttcgtga tcaccggcga gggcatcggc tacccttca        120 agggcaagca gaccatcaac ctgtgcgtga tcgagggcgg ccccctgccc ttcagcgagg       180
acatcctgag cgccggcttc aagtacggcg accggatctt caccgagtac ccccaggaca       240
tcgtggacta cttcaagaac agctgccccg ccggctacac ctggggccgg agcttcctgt       300
tcgaggacgg cgccgtgtgc atctgtaacg tggacatcac cgtgagcgtg aaggagaact       360
gcatctacca caagagcatc ttcaacggcg tgaacttccc cgccgacggc cccgtgatga       420
agaagatgac caccaactgg gaggccagct gcgagaagat catgcccgtg cctaagcagg       480
gcatcctgaa gggcgacgtg agcatgtacc tgctgctgaa ggacggcggc cggtaccggt       540
gccagttcga caccgtgtac aaggccaaga gcgtgcccag caagatgccc gagtggcact       600
tcatccagca aagctgctg cgggaggacc ggagcgacgc caagaaccag aagtggcagc        660
tgaccgagca cgccatcgcc ttccccagcg ccctggcctg agagctcgaa tttccccgat       720
cgttcaaaca tttggcaata aagtttctta agattgaatc ctgttgccgg tcttgcgatg       780
attatcatat aatttctgtt gaattacgtt aagcatgtaa taattaacat gtaatgcatg       840
acgttattta tgagatgggt ttttatgatt agagtcccgc aattatacat ttaatacgcg       900
atagaaaaca aaatatagcg cgcaaactag gataaattat cgcgcgcggt gtcatctatg       960
ttactagatc gggaattcta gtggccggcc cagctgatat ccatcacact ggcggccgct      1020
cgagttctat agtgtcacct aaatcgtatg tgtatgatac ataaggttat gtattaattg      1080
tagccgcgtt ctaacgacaa tatgtccata tggtgcactc tcagtacaat ctgctctgat      1140
gccgcatagt taagccagcc ccgacacccg ccaacacccg ctgacgcgcc ctgacgggct      1200
tgtctgctcc cggcatccgc ttacagacaa gctgtgaccg tctccgggag ctgcatgtgt      1260
cagaggtttt caccgtcatc accgaaacgc gcgagacgaa agggcctcgt gatacgccta      1320
```

```
ttttatagg ttaatgtcat gaccaaaatc ccttaacgtg agttttcgtt ccactgagcg    1380
tcagaccccg tagaaaagat caaaggatct tcttgagatc cttttttct gcgcgtaatc    1440 tgctgcttgc aaacaaaaaa accaccgcta ccagcggtgg tttgtttgcc ggatcaagag    1500
ctaccaactc tttttccgaa ggtaactggc ttcagcagag cgcagatacc aaatactgtc    1560
cttctagtgt agccgtagtt aggccaccac ttcaagaact ctgtagcacc gcctacatac    1620
ctcgctctgc taatcctgtt accagtggct gctgccagtg gcgataagtc gtgtcttacc    1680
gggttggact caagacgata gttaccggat aaggcgcagc ggtcgggctg aacggggggt    1740
tcgtgcacac agcccagctt ggagcgaacg acctacaccg aactgagata cctacagcgt    1800
gagcattgag aaagcgccac gcttcccgaa gggagaaagg cggacaggta tccggtaagc    1860
ggcagggtcg gaacaggaga gcgcacgagg gagcttccag ggggaaacgc ctggtatctt    1920
tatagtcctg tcgggtttcg ccacctctga cttgagcgtc gatttttgtg atgctcgtca    1980 gggggcgga gcctatggaa aaacgccagc aacgcggcct ttttacggtt cctggccttt    2040
tgctggcctt ttgctcacat gttctttcct gcgttatccc ctgattctgt ggataaccgt    2100
attaccgcct ttgagtgagc tgataccgct cgccgcagcc gaacgaccga gcgcagcgag    2160
tcagtgagcg aggaagcgga agagcgccca atacgcaaac cgcctctccc cgcgcgttgg    2220
ccgattcatt aatgcaggtt gatcagatct cgatcccgcg aaattaatac gactcactat    2280
agggagacca caacgtttc cctctagaaa taattttgtt taactttaag aaggagatat    2340
acccatggaa aagcctgaac tcaccgcgac gtctgtcgag aagtttctga tcgaaaagtt    2400
cgacagcgtc tccgacctga tgcagctctc ggagggcgaa gaatctcgtg ctttcagctt    2460
cgatgtagga gggcgtggat atgtcctgcg ggtaaatagc tgcgccgatg gtttctacaa    2520
agatcgttat gtttatcggc actttgcatc ggccgcgctc ccgattccgg aagtgcttga    2580
cattggggaa ttcagcgaga gcctgaccta ttgcatctcc cgccgtgcac agggtgtcac    2640
gttgcaagac ctgcctgaaa ccgaactgcc cgctgttctg cagccggtcg cggaggctat    2700
ggatgcgatc gctgcggccg atcttagcca cgagcgggg ttcggcccat tcggaccgca    2760
aggaatcggt caatacacta catggcgtga tttcatatgc gcgattgctg atccccatgt    2820
gtatcactgg caaactgtga tggacgacac cgtcagtgcg tccgtcgcgc aggctctcga    2880
tgagctgatg ctttgggccg aggactgccc cgaagtccgg cacctcgtgc acgcggattt    2940
cggctccaac aatgtcctga cggacaatgg ccgcataaca gcggtcattg actggagcga    3000
ggcgatgttc ggggattccc aatacgaggt cgccaacatc ttcttctgga ggccgtggtt    3060
ggcttgtatg gagcagcaga cgcgctactt cgagcggagg catccggagc ttgcaggatc    3120
gccgcggctc cgggcgtata tgctccgcat tggtcttgac caactctatc agagcttggt    3180
tgacggcaat ttcgatgatg cagcttgggc gcagggtcga tgcgacgcaa tcgtccgatc    3240
cggagccggg actgtcgggc gtacacaaat cgcccgcaga agcgcggccg tctggaccga    3300
tggctgtgta agtactcg ccgatagtgg aaaccgacgc cccagcactc gtccgagggc    3360
aaaggaatag tgaggtacag cttggatcga tccggctgct aacaaagccc gaaaggaagc    3420
tgagttggct gctgccaccg ctgagcaata actagcataa ccccttgggg cctctaaacg    3480
ggtcttgagg ggttttttgc tgaaaggagg aactatatcc ggatgatcgt cgaggcctca    3540
cgtgttaaca agcttgcatg cctgcaggtt taaacagtcg actctagaga tccgtcaaca    3600
tggtggagca cgacactctc gtctactcca agaatatcaa agatacagtc tcagaagacc    3660
aaagggctat tgagactttt caacaagggg taatatcggg aaacctcctc ggattccatt    3720
```

```
gcccagctat ctgtcacttc atcaaaagga cagtagaaaa ggaaggtggc acctacaaat    3780
gccatcattg cgataaagga aaggctatcg ttcaagatgc ctctgccgac agtggtccca    3840
aagatggacc cccacccacg aggagcatcg tggaaaaaga agacgttcca accacgtctt    3900
caaagcaagt ggattgatgt gatgatccta tgcgtatggt atgacgtgtg ttcaagatga    3960
tgacttcaaa cctacctatg acgtatggta tgacgtgtgt cgactgatga cttagatcca    4020
ctcgagcggc tataaatacg tacctacgca ccctgcgcta ccatccctag agctgcagct    4080
tatttttaca acaattacca acaacaacaa acaacaaaca acattacaat tactatttac    4140
aattacagtc gacccgg                                                   4157
```

SOYBEAN PROMOTERS SC194 AND FLOWER-PREFERRED EXPRESSION THEREOF IN TRANSGENIC PLANTS

CROSS-REFERENCE TO RELATED APPLICATION

This application claims the benefit of U.S. Provisional Application Ser. No. 60/930,877, filed May 17, 2007, which is incorporated by reference herein in its entirety.

FIELD OF THE INVENTION

The present invention relates to the field of plant molecular biology, more particularly to regulation of gene expression in plants.

BACKGROUND OF THE INVENTION

Recent advances in plant genetic engineering have opened new doors to engineer plants to have improved characteristics or traits, such as plant disease resistance, insect resistance, herbicidal resistance, yield improvement, improvement of the nutritional quality of the edible portions of the plant, and enhanced stability or shelf-life of the ultimate consumer product obtained from the plants. Thus, a desired gene (or genes) with the molecular function to impart different or improved characteristics or qualities can be incorporated properly into the plant's genome. The newly integrated gene (or genes) coding sequence can then be expressed in the plant cell to exhibit the desired new trait or characteristic. It is important that appropriate regulatory signals be present in proper configurations in order to obtain the expression of the newly inserted gene coding sequence in the plant cell. These regulatory signals typically include a promoter region, a 5' non-translated leader sequence and a 3' transcription termination/polyadenylation sequence.

A promoter is a non-coding genomic DNA sequence, usually upstream (5') to the relevant coding sequence, to which RNA polymerase binds before initiating transcription. This binding aligns the RNA polymerase so that transcription will initiate at a specific transcription initiation site. The nucleotide sequence of the promoter determines the nature of the RNA polymerase binding and other related protein factors that attach to the RNA polymerase and/or promoter, and the rate of RNA synthesis.

It has been shown that certain promoters are able to direct RNA synthesis at a higher rate than others. These are called "strong promoters". Certain other promoters have been shown to direct RNA synthesis at higher levels only in particular types of cells or tissues and are often referred to as "tissue specific promoters", or "tissue-preferred promoters", if the promoters direct RNA synthesis preferentially in certain tissues (RNA synthesis may occur in other tissues at reduced levels). Since patterns of expression of a chimeric gene (or genes) introduced into a plant are controlled using promoters, there is an ongoing interest in the isolation of novel promoters that are capable of controlling the expression of a chimeric gene (or genes) at certain levels in specific tissue types or at specific plant developmental stages. Among the most commonly used promoters are the nopaline synthase (NOS) promoter (Ebert et al., Proc. Natl. Acad. Sci. USA 84:5745-5749 (1987)); the octapine synthase (OCS) promoter; cauliomovirus promoters such as the cauliflower mosaic virus (CaMV) 19S promoter (Lawton et al., Plant Mol. Biol. 9:315-324 (1987)), the CaMV 35S promoter (Odell et al., Nature 313:810-812 (1985)), and the figwort mosaic virus 35S promoter (Sanger et al., Plant Mol. Biol. 14, 433-43 (1990)); the light inducible promoter from the small subunit of rubisco (Pellegrineschi et al., Biochem. Soc. Trans. 23(2):247-250 (1995)); the Adh promoter (Walker et al., Proc. Natl. Acad. Sci. USA 84:6624-66280 (1987)); the sucrose synthase promoter (Yang et al., Proc. Natl. Acad. Sci. USA 87:4144-4148 (1990)); the R gene complex promoter (Chandler et al., Plant Cell 1:1175-1183 (1989)); the chlorophyll a/b binding protein gene promoter; and the like.

An angiosperm flower is a complex structure generally consisting of a pedicel, sepals, petals, stamens, and a pistil. A stamen comprises a filament and an anther in which the male gametophyte pollens reside. A pistil comprises a stigma, style and ovary. An ovary contains one or more ovules in which the female gametophyte embryo sac, egg cell, central cell, and other specialized cells reside. Flower promoters in general include promoters that direct gene expression in any of the above tissues or cell types.

Although advances in technology provide greater success in transforming plants with chimeric genes, there is still a need for preferred expression of such genes in desired plants. Often times it is desired to selectively express target genes in a specific tissue because of toxicity or efficacy concerns. For example, flower tissue is a type of tissue where preferred expression is desirable and there remains a need for promoters that preferably initiate transcription in flower tissue. Promoters that initiate transcription preferably in flower tissue control genes involved in flower development and flower abortion.

SUMMARY OF THE INVENTION

Compositions and methods for regulating gene expression in a plant are provided. One aspect is for an isolated polynucleotide comprising: a) a nucleotide sequence comprising the sequence set forth in SEQ ID NO:1 or a full-length complement thereof; or b) a nucleotide sequence comprising a sequence having at least 90% sequence identity, based on the BLASTN method of alignment, when compared to the sequence set forth in SEQ ID NO:1; wherein said nucleotide sequence is a promoter. Another aspect is for an isolated polynucleotide comprising (a) a nucleotide sequence comprising a fragment of SEQ ID NO:1, SEQ ID NO:2, SEQ ID NO:3, SEQ ID NO:4, SEQ ID NO:5, SEQ ID NO:6, or SEQ ID NO:7, or a full-length complement thereof; or (b) a nucleotide sequence comprising a sequence having at least 90% sequence identity, based on the BLASTN method of alignment, when compared to the nucleotide sequence of (a); wherein said nucleotide sequence is a promoter.

Other embodiments include recombinant DNA constructs comprising a polynucleotide sequence of the present invention operably linked to a heterologous sequence. Additional, some embodiments provide for transgenic plant cells, transient and stable, transgenic plant seeds, as well as transgenic plants comprising the provided recombinant DNA constructs.

There are provided some embodiments that include methods of expressing a coding sequence or a functional RNA in a flowering plant comprising: introducing a recombinant DNA construct described above into the plant, wherein the heterologous sequence comprises a coding sequence; growing the plant; and selecting a plant displaying expression of the coding sequence or the functional RNA of the recombinant DNA construct.

Furthermore, some embodiments of the present invention include methods of transgenically altering a marketable flower trait of a flowering plant, comprising: introducing a recombinant DNA construct described above into the flowering plant; growing a fertile, mature flowering plant resulting from the introducing step; and selecting a flowering plant expressing the heterologous nucleotide sequence in flower tissue based on the altered marketable flower trait.

Another aspect is for an isolated polynucleotide comprising: (a) a nucleotide sequence encoding a polypeptide, wherein the polypeptide has at least 90% sequence identity, based on the Clustal method of alignment, when compared to the sequence set forth in SEQ ID NO:20, or (b) a full-length complement of the nucleotide sequence of (a).

A further aspect is for an isolated polypeptide, wherein the isolated polypeptide has at least 90% sequence identity, based on the Clustal method of alignment, when compared to the sequence set forth in SEQ ID NO:20.

BRIEF DESCRIPTION OF THE DRAWINGS AND SEQUENCES

The invention can be more fully understood from the following detailed description, the accompanying drawings and Sequence Listing which form a part of this application. The Sequence Listing contains the one letter code for nucleotide sequence characters and the three letter codes for amino acids as defined in conformity with the IUPAC-IUBMB standards described in Nucleic Acids Research 13:3021-3030 (1985) and in the Biochemical Journal 219 (No. 2): 345-373 (1984), which are herein incorporated by reference in their entirety. The symbols and format used for nucleotide and amino acid sequence data comply with the rules set forth in 37 C.F.R. §1.822.

SEQ ID NO:1 is a DNA sequence comprising a 1358 nucleotide soybean SC194 promoter (or full-length SC194 promoter).

SEQ ID NO:2 is a 1328 basepair truncated form of the SC194 promoter shown in SEQ ID NO:1 (bp 30-1357 of SEQ ID NO:1).

SEQ ID NO:3 is a 1134 basepair truncated form of the SC194 promoter shown in SEQ ID NO:1 (bp 224-1357 of SEQ ID NO:1).

SEQ ID NO:4 is a 932 basepair truncated form of the SC194 promoter shown in SEQ ID NO:1 (bp 426-1357 of SEQ ID NO:1).

SEQ ID NO:5 is a 685 basepair truncated form of the SC194 promoter shown in SEQ ID NO:1 (bp 673-1357 of SEQ ID NO:1).

SEQ ID NO:6 is a 472 basepair truncated form of the SC194 promoter shown in SEQ ID NO:1 (bp 886-1357 of SEQ ID NO:1).

SEQ ID NO:7 is a 237 basepair truncated form of the SC194 promoter shown in SEQ ID NO:1 (bp 1121-1357 of SEQ ID NO:1).

SEQ ID NO:8 is an oligonucleotide primer used in the PCR amplifications of the truncated SC194 promoter in SEQ ID NO:2 when paired with SEQ ID NO:9, and the truncated SC194 promoters in SEQ ID NOs: 3, 4, 5, 6 or 7 when paired with SEQ ID NOs: 10, 11, 12, 13, or 14, respectively.

SEQ ID NO:9 is an oligonucleotide primer used in the PCR amplification of the truncated SC194 promoter in SEQ ID NO:2 when paired with SEQ ID NO:8.

SEQ ID NO:10 is an oligonucleotide primer used in the PCR amplification of the truncated SC194 promoter in SEQ ID NO:3 when paired with SEQ ID NO:8.

SEQ ID NO:11 is an oligonucleotide primer used in the PCR amplification of the truncated SC194 promoter in SEQ ID NO:4 when paired with SEQ ID NO:8.

SEQ ID NO:12 is an oligonucleotide primer used in the PCR amplification of the truncated SC194 promoter in SEQ ID NO:5 when paired with SEQ ID NO:8.

SEQ ID NO:13 is an oligonucleotide primer used in the PCR amplification of the truncated SC194 promoter in SEQ ID NO:6 when paired with SEQ ID NO:8.

SEQ ID NO:14 is an oligonucleotide primer used in the PCR amplification of the truncated SC194 promoter in SEQ ID NO:7 when paired with SEQ ID NO:8.

SEQ ID NO:15 is an oligonucleotide primer specific to the soybean PSO375649 gene used in the first nested PCR amplification of the SC194 promoter when paired with SEQ ID NO:16.

SEQ ID NO:16 is an oligonucleotide primer used in the first nested PCR amplification of the SC194 promoter when paired with SEQ ID NO:15.

SEQ ID NO:17 is an oligonucleotide primer specific to the soybean PSO375649 gene used in the second nested PCR amplification of the SC194 promoter when paired with SEQ ID NO:18. An NcoI restriction site CCATGG is added for subsequent cloning.

SEQ ID NO:18 is an oligonucleotide primer used in the second nested PCR amplification of the SC194 promoter when paired with SEQ ID NO:17.

SEQ ID NO:19 is the nucleotide sequence of a novel soybean cDNA PSO375649 encoding an unknown polypeptide. Nucleotides 1 to 86 are the 5' untranslated sequence, nucleotides 87 to 89 are the translation initiation codon, nucleotides 87 to 467 are polypeptide coding region, nucleotides 468 to 470 are the termination codon, nucleotides 468 to 804 are the 3' untranslated sequence, nucleotides 805 to 832 are part of the poly (A) tail.

SEQ ID NO:20 is the 127 amino acid long putative PSO375649 translation product SC194 protein sequence.

SEQ ID NO:21 is an oligonucleotide primer used in the diagnostic PCR to check for soybean genomic DNA presence in total RNA or cDNA when paired with SEQ ID NO:22.

SEQ ID NO:22 is an oligonucleotide primer used in the diagnostic PCR to check for soybean genomic DNA presence in total RNA or cDNA when paired with SEQ ID NO:21.

SEQ ID NO:23 is the longer strand sequence of the adaptor supplied in ClonTech™ GenomeWalker™ kit.

SEQ ID NO:24 is an MPSS tag sequence that is specific to the unique gene PSO375649.

SEQ ID NO:25 is a sense primer used in quantitative RT-PCR analysis of PSO375649 gene expression profile.

SEQ ID NO:26 is an antisense primer used in quantitative RT-PCR analysis of PSO375649 gene expression profile.

SEQ ID NO:27 is a sense primer used as an endogenous control gene-specific primer in the quantitative RT-PCR analysis of PSO375649 gene expression profile.

SEQ ID NO:28 is an antisense primer used as an endogenous control gene-specific primer in the quantitative RT-PCR analysis of PSO375649 gene expression profile.

SEQ ID NO:29 is a sense primer used in quantitative PCR analysis of SAMS:ALS transgene copy numbers.

SEQ ID NO:30 is a FAM labeled fluorescent DNA oligo probe used in quantitative PCR analysis of SAMS:ALS transgene copy numbers.

SEQ ID NO:31 is an antisense primer used in quantitative PCR analysis of SAMS:ALS transgene copy numbers.

SEQ ID NO:32 is a sense primer used in quantitative PCR analysis of GM-SC194:YFP transgene copy numbers.

SEQ ID NO:33 is a FAM labeled fluorescent DNA oligo probe used in quantitative PCR analysis of GM-SC194:YFP transgene.copy numbers.

SEQ ID NO:34 is an antisense primer used in quantitative PCR analysis of GM-SC194:YFP transgene copy numbers.

SEQ ID NO:35 is a sense primer used as an endogenous control gene primer in quantitative PCR analysis of transgene copy numbers.

SEQ ID NO:36 is a VIC labeled DNA oligo probe used as an endogenous control gene probe in quantitative PCR analysis of transgene copy numbers.

SEQ ID NO:37 is an antisense primer used as an endogenous control gene primer in quantitative PCR analysis of transgene copy numbers.

SEQ ID NO:38 is the recombination site attB1 sequence in the Gateway cloning system (Invitrogen).

SEQ ID NO:39 is the recombination site attB2 sequence in the Gateway cloning system (Invitrogen).

SEQ ID NO:40 is the 3291 bp sequence of QC299.
SEQ ID NO:41 is the 4642 bp sequence of QC300.
SEQ ID NO:42 is the 8187 bp sequence of PHP25224.
SEQ ID NO:43 is the 8945 bp sequence of QC302.
SEQ ID NO:44 is the 2817 bp sequence of pCR8/GW/TOPO.
SEQ ID NO:45 is the 4145 bp sequence of QC300-1.
SEQ ID NO:46 is the 5286 bp sequence of QC330.
SEQ ID NO:47 is the 4986 bp sequence of QC300-1Y.
SEQ ID NO:48 is the 4792 bp sequence of QC300-2Y.
SEQ ID NO:49 is the 4590 bp sequence of QC300-3Y.
SEQ ID NO:50 is the 4343 bp sequence of QC300-4Y.
SEQ ID NO:51 is the 4130 bp sequence of QC300-5Y.
SEQ ID NO:52 is the 3895 bp sequence of QC300-6Y.
SEQ ID NO:53 is the 4157 bp sequence of pZSL90.

Table 1 displays the relative abundance (parts per million, PPM) of the PSO375649 gene determined by Lynx MPSS gene expression profiling.

Table 2 displays the relative transgene copy numbers and YFP expression of SC194:YFP transgenic soybean plants.

FIG. 1 displays the logarithm of relative quantifications of the PSO375649 gene expression in 14 different soybean tissues by quantitative RT-PCR. The gene expression profile indicates that the PSO375649 gene is highly expressed in flower buds and open flowers.

Figure 2:
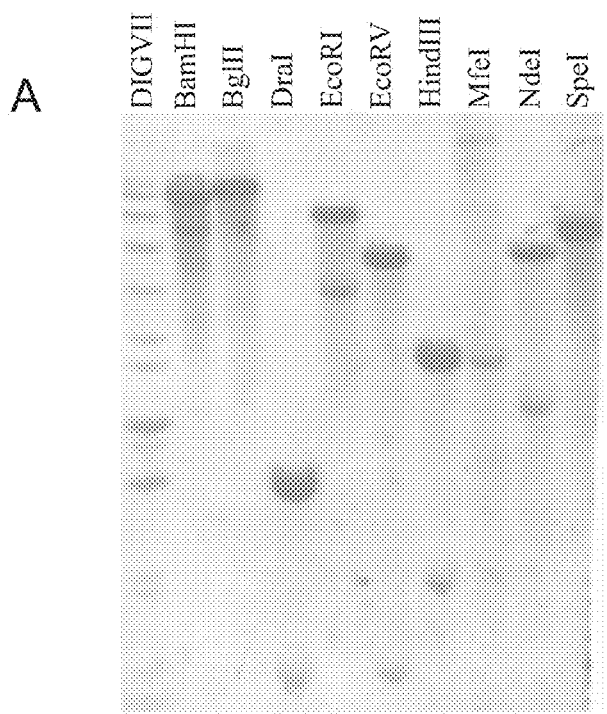
Figure 2:
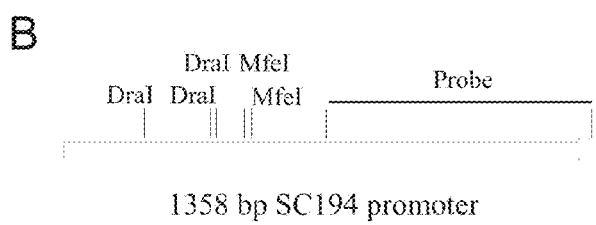

FIG. 2 displays the SC194 promoter copy number analysis by Southern hybridization. Also displayed is a schematic of the SC194 promoter showing relative linear positions of a number of restriction sites.

Figure 3:
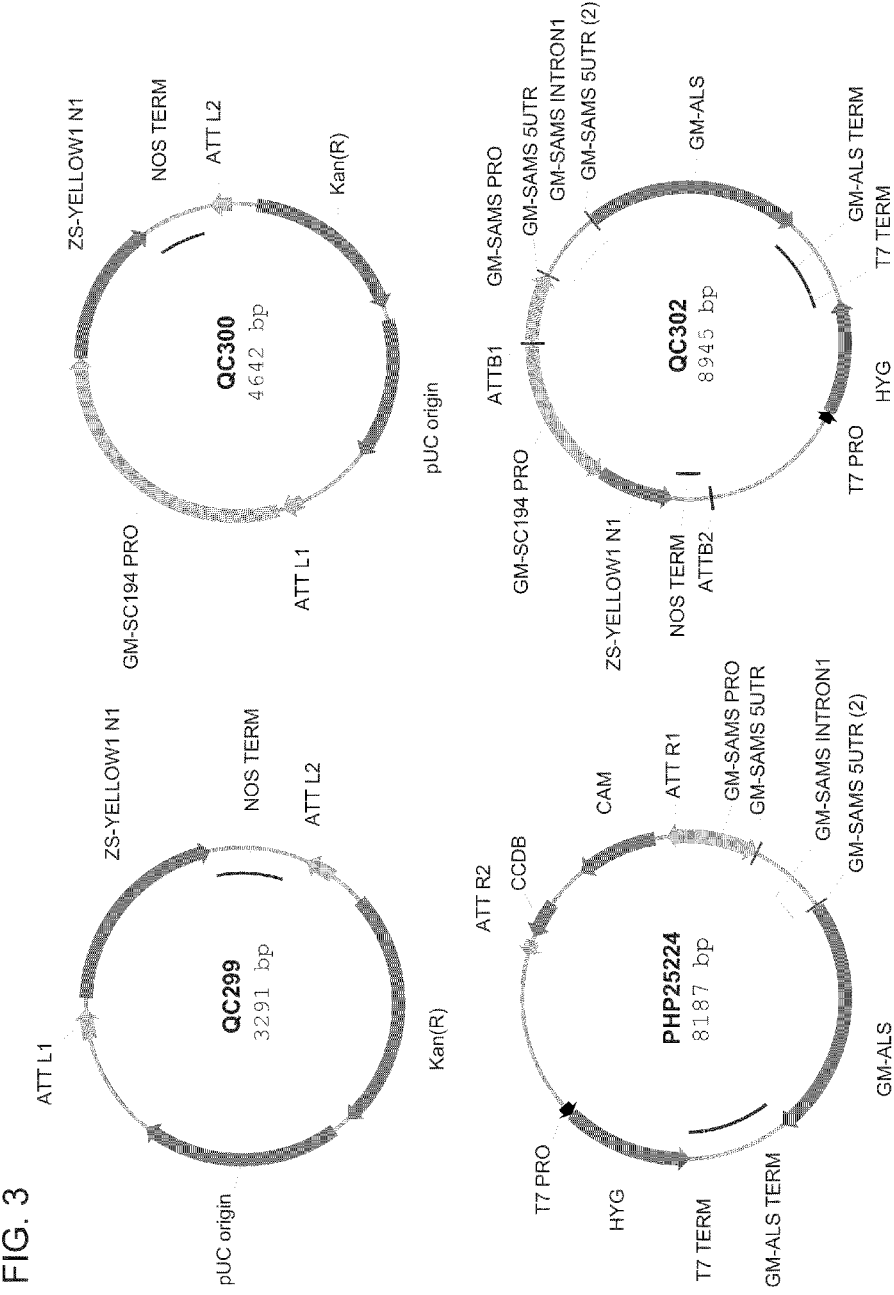

FIG. 3 is a schematic representation of the map of plasmids QC299, QC300, PHP25224, and QC302.

Figure 4:
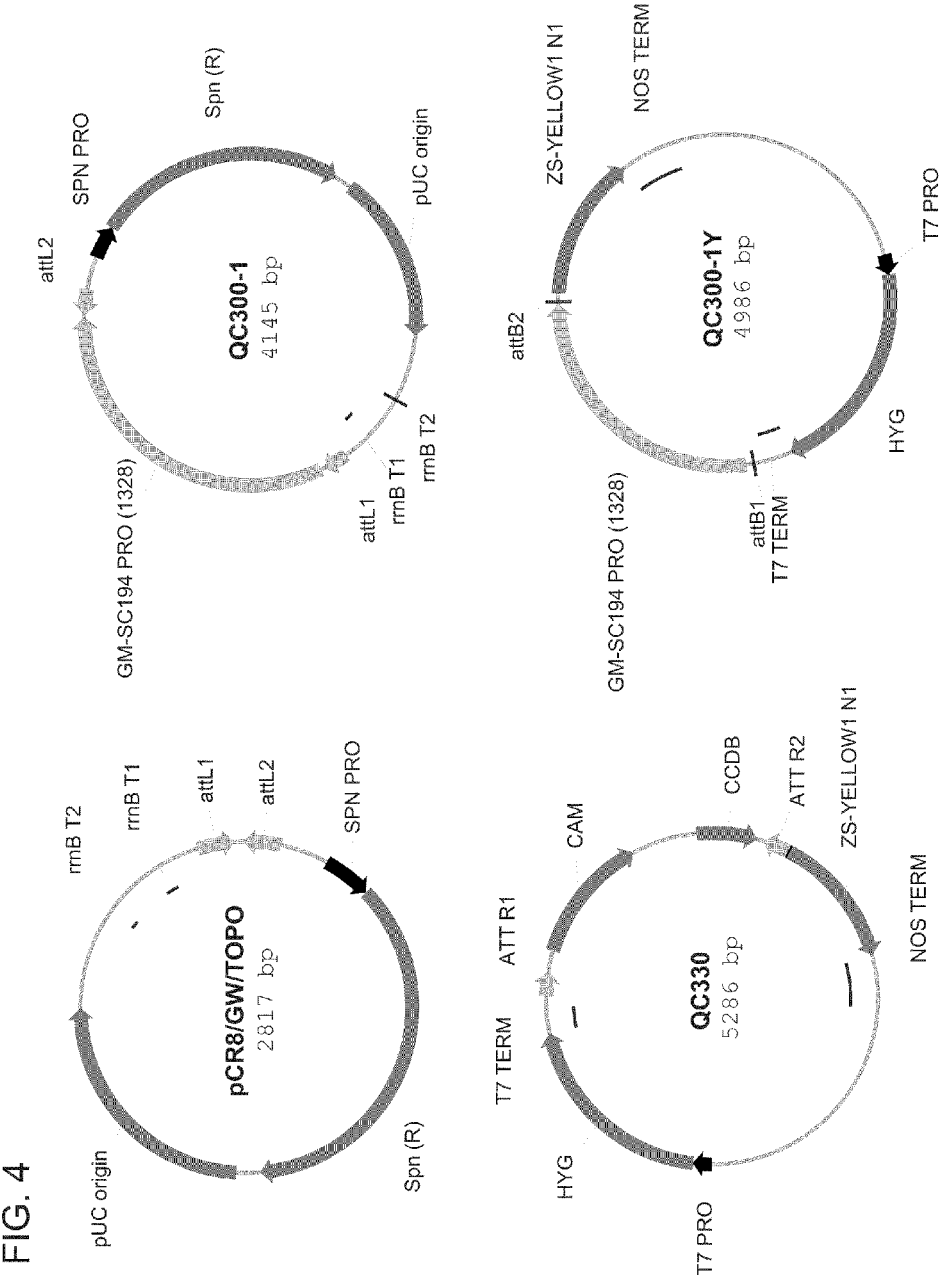

FIG. 4 displays schematic representations of a Gateway cloning entry vector pCR8/GW/TOPO (Invitrogen), the construct QC300-1 created by cloning the full length SC194 promoter into pCR8/GW/TOPO, a Gateway cloning destination vector QC330 containing a reporter ZS-YELLOW1 N1, and a final construct QC300-1Y with the 1328 bp truncated SC194 promoter (SEQ ID NO:2) placed in front of the ZS-YELLOW1 N1 reporter gene. Promoter deletion constructs QC300-2Y, QC300-3Y, QC300-4Y, QC300-5Y, and QC300-6Y containing the 1134, 932, 685, 472, and 237 bp truncated SC194 promoters, respectively, have similar map configurations, the difference being in the length of the promoter.

Figure 5:
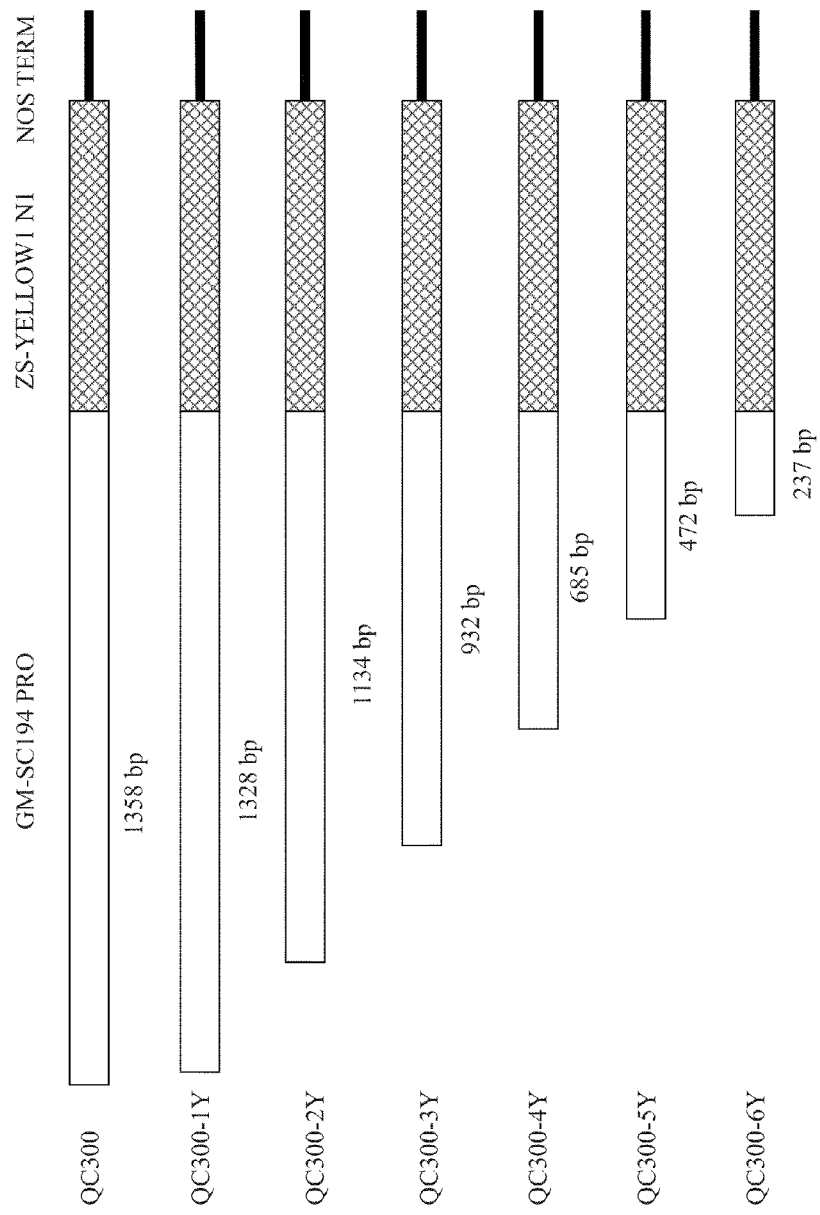

FIG. 5 is a linear schematic of the SC194 promoter constructs QC300, QC300-1Y, QC300-2Y, QC300-3Y, QC300-4Y, QC300-5Y, and QC300-6Y wherein the reporter ZS-YELLOW1N1 is operably linked to the full length SC194 promoter and the progressive truncations of the SC194 promoter.

Figure 6:
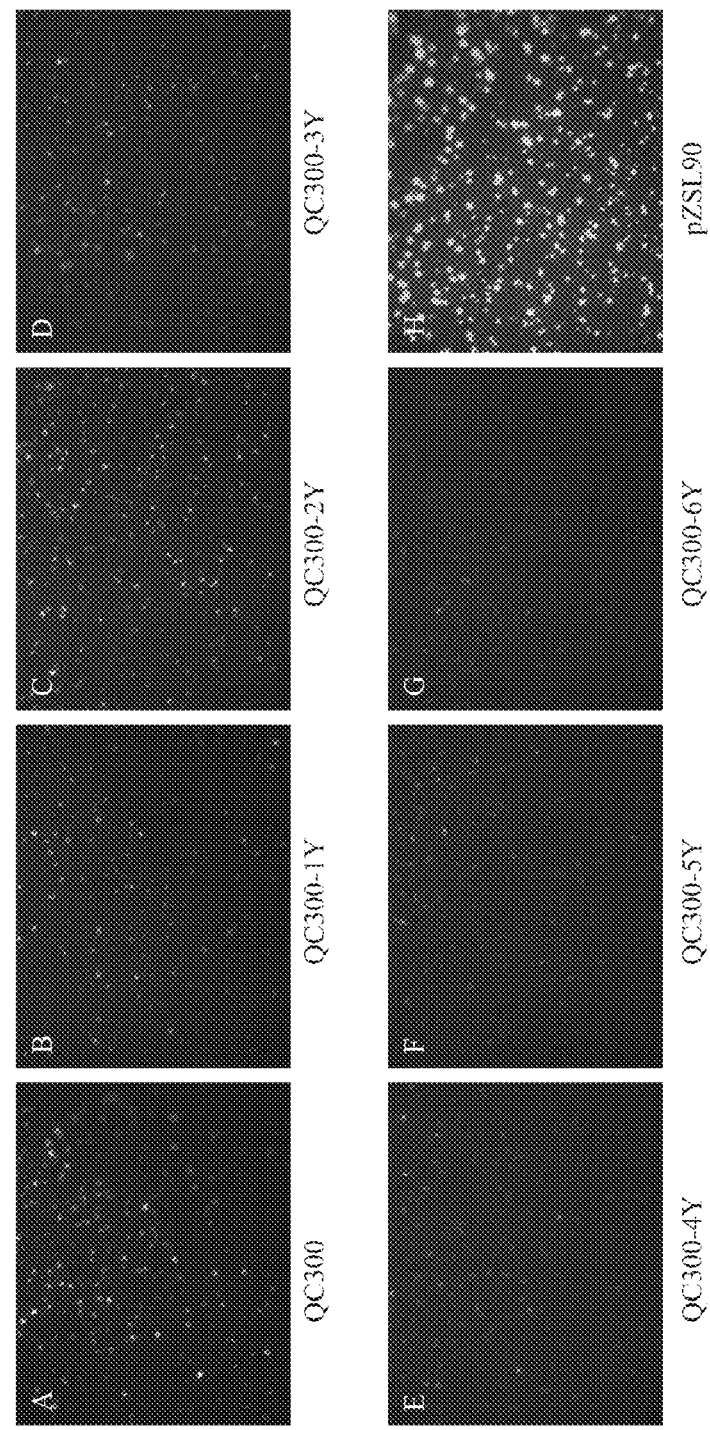

FIG. 6 displays the transient expression of the fluorescent protein reporter gene ZS-YELLOW1 N1 in the cotyledons of germinating soybean seeds. The reporter gene is driven by the full length SC194 promoter in construct QC300, or driven by the SC194 promoter or the progressively truncated SC194 promoters in the transient expression constructs QC300-1Y to QC300-6Y. Construct pZSL90 represents the positive control (constitutive promoter SCP1 drives the same reporter gene).

Figure 7:

FIG. 7 displays the stable expression of the fluorescent protein reporter gene ZS-YELLOW1 N1 in the floral and other tissues of transgenic soybean plants containing a single copy of the transgene construct QC302. The green color indicates ZS-YELLOW1 N1 gene expression. The red color is background auto fluorescence from plant green tissues.

DETAILED DESCRIPTION OF THE INVENTION

The disclosure of all patents, patent applications, and publications cited herein are incorporated by reference in their entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

In the context of this disclosure, a number of terms shall be utilized.

The term "promoter" refers to a nucleotide sequence capable of controlling the expression of a coding sequence or functional RNA. Functional RNA includes, but is not limited to, transfer RNA (tRNA) and ribosomal RNA (rRNA). Numerous examples of promoters may be found in the compilation by Okamuro and Goldberg (Biochemistry of Plants 15:1-82 (1989)). The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". It is further recognized that, since in most cases the exact boundaries of regulatory sequences have not been completely defined, DNA fragments of some variation may have identical promoter activity.

An "intron" is an intervening sequence in a gene that is transcribed into RNA and then excised in the process of generating the mature mRNA. The term is also used for the excised RNA sequences. An "exon" is a portion of the sequence of a gene that is transcribed and is found in the mature messenger RNA derived from the gene, and is not necessarily a part of the sequence that encodes the final gene product.

A "flower" is a complex structure consisting of pedicel, sepal, petal, stamen, and carpel. A stamen comprises an anther, pollen and filament. A carpel comprises a stigma, style and ovary. An ovary comprises an ovule, embryo sac, and egg cell. Soybean pods develop from the pistil. It is likely that a gene expressed in the pistil of a flower continues to express in early pod. A "flower cell" is a cell from any one of these structures. Flower promoters in general include promoters that direct gene expression in any of the above tissues or cell types.

The term "flower crop" or "flowering plants" are plants that produce flowers that are marketable within the floriculture industry. Flower crops include both cut flowers and potted flowering plants. Cut flowers are plants that generate flowers that can be cut from the plant and can be used in fresh flower arrangements. Flower crops include roses, carnations, Gerberas, Chrysanthemums, tulips, Gladiolis, Alstroemerias, Anthuriums, lisianthuses, larkspurs, irises, orchids, snapdragons, African violets, azaleas, in addition to other less popular flower crops.

The terms "flower-specific promoter" or "flower-preferred promoter" may be used interchangeably herein and refer to promoters active in flower, with promoter activity being significantly higher in flower tissue versus non-flower tissue. "Preferentially initiates transcription", when describing a particular cell type, refers to the relative level of transcription in that particular cell type as opposed to other cell types. The described SC194 promoters are promoters that preferentially initiate transcription in flower cells. Preferably, the promoter activity in terms of expression levels of an operably linked sequence is more than ten-fold higher in flower tissue than non-flower tissue. More preferably, the promoter activity is present in flower tissue while undetectable in non-flower tissue.

As used herein, an "SC194 promoter" refers to one type of flower-specific promoter. The native SC194 promoter (or full-length native SC194 promoter) is the native promoter of the putative soybean SC194 polypeptide, which is a novel protein without significant homology to any known protein in public databases. The "SC194 promoter", as used herein, also refers to fragments of the full-length native promoter that retain significant promoter activity. For example, an SC194 promoter of the present invention can be the full-length promoter (SEQ ID NO:1) or a promoter-functioning fragment thereof, which includes, among others, the polynucleotides of SEQ ID NOs: 2, 3, 4, 5, 6 and 7. An SC194 promoter also includes variants that are substantially similar and functionally equivalent to any portion of the nucleotide sequence set forth in SEQ ID NOs: 1, 2, 3, 4, 5, 6, or 7, or sequences therebetween.

An "isolated nucleic acid fragment" or "isolated polynucleotide" refers to a polymer of ribonucleotides (RNA) or deoxyribonucleotides (DNA) that is single-stranded or double-stranded, optionally containing synthetic, non-natural or altered nucleotide bases. An isolated polynucleotide in the form of DNA may be comprised of one or more segments of cDNA, genomic DNA or synthetic DNA.

The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

A "heterologous nucleic acid fragment" or "heterologous nucleotide sequence" refers to a nucleotide sequence that is not naturally occurring with the plant promoter sequence of the invention. While this nucleotide sequence is heterologous to the promoter sequence, it may be homologous, or native, or heterologous, or foreign, to the plant host. However, it is recognized that the instant promoters may be used with their native coding sequences to increase or decrease expression resulting in a change in phenotype in the transformed seed.

The terms "fragment (or variant) that is functionally equivalent" and "functionally equivalent fragment (or variant)" are used interchangeably herein. These terms refer to a portion or subsequence or variant of the promoter sequence of the present invention in which the ability to initiate transcription or drive gene expression (such as to produce a certain phenotype) is retained. Fragments and variants can be obtained via methods such as site-directed mutagenesis and synthetic construction. As with the provided promoter sequences described herein, the contemplated fragments and variants operate to promote the flower-preferred expression of an operably linked heterologous nucleic acid sequence, forming a recombinant DNA construct (also, a chimeric gene). For example, the fragment or variant can be used in the design of recombinant DNA constructs to produce the desired phenotype in a transformed plant. Recombinant DNA constructs can be designed for use in co-suppression or antisense by linking a promoter fragment or variant thereof in the appropriate orientation relative to a heterologous nucleotide sequence.

In some aspects of the present invention, the promoter fragments can comprise at least about 20 contiguous nucleotides, or at least about 50 contiguous nucleotides, or at least about 75 contiguous nucleotides, or at least about 100 contiguous nucleotides of SEQ ID NO:1, SEQ ID NO:2, SEQ ID NO:3, SEQ ID NO:4, SEQ ID NO:5, SEQ ID NO:6, or SEQ ID NO:7. In another aspect, a promoter fragment is the nucleotide sequence set forth in SEQ ID NO:2, SEQ ID NO:3, SEQ ID NO:4, SEQ ID NO:5, SEQ ID NO:6, or SEQ ID NO:7. The nucleotides of such fragments will usually comprise the TATA recognition sequence of the particular promoter sequence. Such fragments may be obtained by use of restriction enzymes to cleave the naturally occurring promoter nucleotide sequences disclosed herein, by synthesizing a nucleotide sequence from the naturally occurring promoter DNA sequence, or may be obtained through the use of PCR technology. See particularly, Mullis et al., Methods Enzymol. 155:335-350 (1987), and Higuchi, R. In PCR Technology: Principles and Applications for DNA Amplifications; Erlich, H. A., Ed.; Stockton Press Inc.: New York, 1989.

The terms "substantially similar" and "corresponding substantially" as used herein refer to nucleic acid sequences, particularly promoter sequences, wherein changes in one or more nucleotide bases do not substantially alter the ability of the promoter to initiate transcription or drive gene expression or produce a certain phenotype. These terms also refer to modifications, including deletions and variants, of the nucleic acid sequences of the instant invention by way of deletion or insertion of one or more nucleotides that do not substantially alter the functional properties of the resulting promoter relative to the initial, unmodified promoter. It is therefore understood, as those skilled in the art will appreciate, that the invention encompasses more than the specific exemplary sequences.

In one example of substantially similar, substantially similar nucleic acid sequences include those that are also defined by their ability to hybridize to the disclosed nucleic acid sequences, or portions thereof. Substantially similar nucleic acid sequences include those sequences that hybridize, under moderately stringent conditions (for example, 0.5×SSC, 0.1% SDS, 60° C.) with the sequences exemplified herein, or to any portion of the nucleotide sequences reported herein and which are functionally equivalent to the promoter of the invention. Estimates of such homology are provided by either DNA-DNA or DNA-RNA hybridization under conditions of stringency as is well understood by those skilled in the art (Hames and Higgins, Eds.; In Nucleic Acid Hybridisation; IRL Press: Oxford, U.K., 1985). Stringency conditions can be adjusted to screen for moderately similar fragments, such as homologous sequences from distantly related organisms, to highly similar fragments, such as genes that duplicate functional enzymes from closely related organisms. Post-hybridization washes partially determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. Another set of stringent conditions uses higher temperatures in which the washes are identical to those above except for the temperature of the final two 30 min washes in 0.2× SSC, 0.5% SDS is increased to 60° C. Another set of highly stringent conditions uses two final washes in 0.1×SSC, 0.1% SDS at 65° C.

In some examples, substantially similar nucleic acid sequences are those sequences that are at least 80% identical to the nucleic acid sequences reported herein or which are at least 80% identical to any portion of the nucleotide sequences reported herein. In some instances, substantially similar nucleic acid sequences are those that are at least 90% identical to the nucleic acid sequences reported herein, or at least 90% identical to any portion of the nucleotide sequences reported herein. In some examples, substantially similar nucleic acid sequences are those that are at least 95% identical to the nucleic acid sequences reported herein, or are at least 95% identical to any portion of the nucleotide sequences reported herein. It is well understood by one skilled in the art that many levels of sequence identity are useful in identifying related polynucleotide sequences. Useful examples of percent identities are those listed above, or also any integer percentage from 80% to 100%, such as, for example, 81%, 82%, 83%, 84%, 85%, 86%, 87%, 88%, 89%, 90%, 91%, 92%, 93%, 94%, 95%, 96%, 97%, 98% and 99%.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid sequence for improved expression in a host cell, it is desirable to design the nucleic acid sequence such that its frequency of codon usage approaches the frequency of preferred codon usage of the host cell.

Sequence alignments and percent similarity calculations may be determined using the Megalign program of the LASARGENE bioinformatics computing suite (DNASTAR Inc., Madison, Wis.). Multiple alignment of the sequences are performed using the Clustal method of alignment (Higgins and Sharp, CABIOS 5:151-153 (1989)) with the default parameters (GAP PENALTY=10, GAP LENGTH PENALTY=10). Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are GAP PENALTY=10, GAP LENGTH PENALTY=10, KTUPLE=2, GAP PENALTY=5, WINDOW=4 and DIAGONALS SAVED=4. A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Altschul, S. F. et al., J. Mol. Biol. 215:403-410 (1993)) and Gapped Blast (Altschul, S. F. et al., Nucleic Acids Res. 25:3389-3402 (1997)). BLASTN refers to a BLAST program that compares a nucleotide query sequence against a nucleotide sequence database.

The term "gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" or "recombinant expression construct", which are used interchangeably, refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, and arranged in a manner different than that found in nature. "Endogenous gene" refers to a native gene in its natural location in the genome of an organism. A "foreign" gene refers to a gene not normally found in the host organism, which is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that encodes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, and are not limited to, promoters, enhancers, translation leader sequences, introns, and polyadenylation recognition sequences.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D., Molecular Biotechnology 3:225 (1995)).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized as affecting the addition of polyadenylic acid tracts to the 3' end of the mRNA precursor. The use of different 3' non-coding sequences is exemplified by Ingelbrecht et al., Plant Cell 1:671-680 (1989).

"RNA transcript" refers to a product resulting from RNA polymerase-catalyzed transcription of a DNA sequence. When an RNA transcript is a perfect complementary copy of a DNA sequence, it is referred to as a primary transcript, or it may be a RNA sequence derived from posttranscriptional processing of a primary transcript and is referred to as a mature RNA. "Messenger RNA" ("mRNA") refers to RNA that is without introns and that can be translated into protein by the cell. "cDNA" refers to a DNA that is complementary to and synthesized from an mRNA template using the enzyme reverse transcriptase. The cDNA can be single-stranded or converted into the double-stranded using the Klenow fragment of DNA polymerase I. "Sense" RNA refers to RNA transcript that includes mRNA and so can be translated into protein within a cell or in vitro. "Antisense RNA" refers to a RNA transcript that is complementary to all or part of a target primary transcript or mRNA and that blocks expression or transcripts accumulation of a target gene. The complementarity of an antisense RNA may be with any part of the specific gene transcript, i.e. at the 5' non-coding sequence, 3' non-coding sequence, introns, or the coding sequence. "Functional RNA" refers to antisense RNA, ribozyme RNA, or other RNA that may not be translated yet has an effect on cellular processes.

The term "operably linked" refers to the association of nucleic acid sequences on a single polynucleotide so that the function of one is affected by the other. For example, a promoter is operably linked with a heterologous nucleotide sequence, e.g., a coding sequence, when it is capable of affecting the expression of that heterologous nucleotide sequence (i.e., for example, the coding sequence is under the transcriptional control of the promoter). A coding sequence can be operably linked to promoter sequences in sense or antisense orientation.

The terms "initiate transcription", "initiate expression", "drive transcription", and "drive expression" are used interchangeably herein and all refer to the primary function of a promoter. As detailed throughout this disclosure, a promoter is a non-coding genomic DNA sequence, usually upstream (5') to the relevant coding sequence, and its primary function is to act as a binding site for RNA polymerase and initiate transcription by the RNA polymerase. Additionally, there is "expression" of RNA, including functional RNA, or the expression of polypeptide for operably linked encoding nucleotide sequences, as the transcribed RNA ultimately is translated into the corresponding polypeptide.

The term "expression", as used herein, refers to the production of a functional end-product, e.g., an mRNA or a protein (precursor or mature).

The term "recombinant DNA construct" or "recombinant expression construct" is used interchangeably and refers to a discrete polynucleotide into which a nucleic acid sequence or fragment can be moved. Preferably, it is a plasmid vector or a fragment thereof comprising the promoters of the present invention. The choice of plasmid vector is dependent upon the method that will be used to transform host plants. The skilled artisan is well aware of the genetic elements that must be present on the plasmid vector in order to successfully transform, select and propagate host cells containing the recombinant DNA construct. The skilled artisan will also recognize that different independent transformation events will result in different levels and patterns of expression (Jones et al., EMBO J. 4:2411-2418 (1985); De Almeida et al., Mol. Gen. Genetics 218:78-86 (1989)), and thus that multiple events must be screened in order to obtain lines displaying the desired expression level and pattern. Such screening may be accomplished by PCR and Southern analysis of DNA, RT-PCR and Northern analysis of mRNA expression, Western analysis of protein expression, or phenotypic analysis.

Expression or overexpression of a gene involves transcription of the gene and translation of the mRNA into a precursor or mature protein. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression or transcript accumulation of identical or substantially similar foreign or endogenous genes (U.S. Pat. No. 5,231,020). The mechanism of co-suppression may be at the DNA level (such as DNA methylation), at the transcriptional level, or at post-transcriptional level.

Co-suppression constructs in plants previously have been designed by focusing on overexpression of a nucleic acid sequence having homology to an endogenous mRNA, in the sense orientation, which results in the reduction of all RNA having homology to the overexpressed sequence (see Vaucheret et al., Plant J. 16:651-659 (1998); and Gura, Nature 404:804-808 (2000)). The overall efficiency of this phenomenon is low, and the extent of the RNA reduction is widely variable. Recent work has described the use of "hairpin" structures that incorporate all, or part, of an mRNA encoding sequence in a complementary orientation that results in a potential "stem-loop" structure for the expressed RNA (WO99/53050 and WO02/00904). This increases the frequency of co-suppression in the recovered transgenic plants. Another variation describes the use of plant viral sequences to direct the suppression, or "silencing", of proximal mRNA encoding sequences (WO98/36083). Neither of these co-suppressing phenomena has been elucidated mechanistically at the molecular level, although genetic evidence has been obtained that may lead to the identification of potential components (Elmayan et al., Plant Cell 10:1747-1757 (1998)).

As stated herein, "suppression" refers to a reduction of the level of enzyme activity or protein functionality (e.g., a phenotype associated with a protein) detectable in a transgenic plant when compared to the level of enzyme activity or protein functionality detectable in a non-transgenic or wild type plant with the native enzyme or protein. The level of enzyme activity in a plant with the native enzyme is referred to herein as "wild type" activity. The level of protein functionality in a plant with the native protein is referred to herein as "wild type" functionality. The term "suppression" includes lower, reduce, decline, decrease, inhibit, eliminate and prevent. This reduction may be due to a decrease in translation of the native mRNA into an active enzyme or functional protein. It may also be due to the transcription of the native DNA into decreased amounts of mRNA and/or to rapid degradation of the native mRNA. The term "native enzyme" refers to an enzyme that is produced naturally in a non-transgenic or wild type cell. The terms "non-transgenic" and "wild type" are used interchangeably herein.

"Altering expression" refers to the production of gene product(s) in transgenic organisms in amounts or proportions that differ significantly from the amount of the gene product(s) produced by the corresponding wild-type organisms (i.e., expression is increased or decreased).

"Transformation" refers to the transfer of a nucleic acid fragment into the genome of a host organism, resulting in genetically stable inheritance. Host organisms containing the transformed nucleic acid fragments are referred to as "transgenic" organisms. Thus, a "transgenic plant cell" as used herein refers to a plant cell containing the transformed nucleic acid fragments. The preferred method of soybean cell transformation is use of particle-accelerated or "gene gun" transformation technology (Klein, T., Nature (London) 327:70-73 (1987); U.S. Pat. No. 4,945,050).

"Transient expression" refers to the temporary expression of often reporter genes such as β-glucuronidase (GUS), fluorescent protein genes GFP, ZS-YELLOW1 N1, AM-CYAN1, DS-RED in selected certain cell types of the host organism in which the transgenic gene is introduced temporally by a transformation method. The transformed materials of the host organism are subsequently discarded after the transient gene expression assay.

A "marketable flower trait" is a characteristic or phenotype of the flower of a plant such as the color, scent or morphology of a flower. The marketable flower trait is a characteristic of a flower that is of high regard to a flower crop consumer in deciding whether to purchase the flower crop.

The phrase "genes involved in anthocyanin biosynthesis" refers to genes that encode proteins that play a role in converting metabolic precursors into the one of a number of anthocyanins. Examples of genes involved in the biosynthesis of anthocyanin are dyhydroflavonol 4-reductase, flavonoid 3,5-hydroxylase, chalcone synthase, chalcone isomerase, flavonoid 3-hydroxylase, anthocyanin synthase, and UDP-glucose 3-O-flavonoid glucosyl transferase (see, e.g., Mori et al., Plant Cell Reports 22:415-421 (2004)).

The phrase "genes involved in the biosynthesis of fragrant fatty acid derivatives" refers to genes that encode proteins that play a role in manipulating the biosynthesis of fragrant fatty acid derivatives such as terpenoids, phenylpropanoids, and benzenoids in flowers (see, e.g., Tanaka et al., Plant Cell, Tissue and Organ Culture 80:1-24 (2005)). Examples of such genes include S-linalool synthase, acetyl CoA:benzylalcohol acetyltransferase, benzyl CoA:benzylalcohol benzoyl transferase, S-adenosyl-L-methionine:benzoic acid carboxyl methyl transferase (BAMT), mycrene synthases, (E)-β-ocimene synthase, orcinol O-methyltransferase, and limonene synthases (see, e.g., Tanaka et al., supra).

The term "flower homeotic genes" or "flower morphology modifying genes" refers to genes that are involved in pathways associated with flower morphology. A modification of flower morphology can lead to a novel form of the respective flower that can enhance its value in the flower crop marketplace. Morphology can include the size, shape, or petal pattern of a flower. Some example of flower homeotic genes include genes involved in cell-fate determination (in ABC combinatorial model of gene expression), including AGAMOUS, which determines carpel fate in the central whorl, APETALA3, which determines the sepal fate in the outer whorl, and PISTILLATA, which determines petal development in the second whorl (Espinosa-Soto et al., *Plant Cell* 16:2923-2939 (2004)).

Standard recombinant DNA and molecular cloning techniques used herein are well known in the art and are described more fully in Sambrook, J. et al., In Molecular Cloning: A Laboratory Manual; 2$^{nd}$ ed.; Cold Spring Harbor Laboratory Press: Cold Spring Harbor, N.Y., 1989 (hereinafter "Sambrook et al., 1989") or Ausubel, F. M., Brent, R., Kingston, R. E., Moore, D. D., Seidman, J. G., Smith, J. A. and Struhl, K., Eds.; In Current Protocols in Molecular Biology; John Wiley and Sons: New York, 1990 (hereinafter "Ausubel et al., 1990").

"PCR" or "Polymerase Chain Reaction" is a technique for the synthesis of large quantities of specific DNA segments consisting of a series of repetitive cycles (Perkin Elmer Cetus Instruments, Norwalk, Conn.). Typically, the double stranded DNA is heat denatured; the two primers complementary to the 3' boundaries of the target segment are annealed at low temperature and then extended at an intermediate temperature. One set of these three consecutive steps comprises a cycle.

Embodiments of the present invention include isolated polynucleotides comprising a nucleotide sequence that is a promoter. In some instances, the nucleotide sequence includes one or more of the following:
 a) the sequence set forth in SEQ ID NO:1 or a full-length complement thereof; or
 b) a nucleotide sequence comprising a sequence having at least 90% sequence identity, based on the BLASTN method of alignment, when compared to the sequence set forth in SEQ ID NO:1.

In other aspects, the nucleotide sequence includes one or more of the following:
 (a) a nucleotide sequence comprising a fragment of SEQ ID NO:1, SEQ ID NO:2, SEQ ID NO:3, SEQ ID NO:4, SEQ ID NO:5, SEQ ID NO:6, or SEQ ID NO:7, or a full-length complement thereof; or
 (b) a nucleotide sequence comprising a sequence having at least 90% sequence identity, based on the BLASTN method of alignment, when compared to the nucleotide sequence of (a).

The nucleotide sequences of the present invention can be referred to as a promoter or as having promoter-like activity. In some embodiments the nucleotide sequence is a promoter that preferentially initiates transcription in a plant flower cell. Such promoter is referred to as a flower-specific promoter. Preferably the promoter of the present invention is the soybean "SC194" promoter.

In a preferred embodiment, the promoter comprises the nucleotide sequence set forth in SEQ ID NO:1, SEQ ID NO:2, SEQ ID NO:3, SEQ ID NO:4, SEQ ID NO:5, SEQ ID NO:6, or SEQ ID NO:7. The present invention also includes nucleic acid fragments, variants, and complements of the aforementioned nucleotide sequences or promoters, provided that they are substantially similar and functionally equivalent to the nucleotide sequence set forth in these nucleotide sequences. A nucleic acid fragment or variant that is functionally equivalent to the present SC194 promoter is any nucleic acid fragment or variant that is capable of initiating the expression, preferably initiating flower-specific expression, of a coding sequence or functional RNA in a similar manner to the SC194 promoter. The expression patterns of SC194 gene and its promoter are set forth in Examples 1, 2, 7, and 8. In one example, the expression pattern of a SC194 promoter fragment or variant will have expression patterns similar to that of the SC194 promoter.

In some aspects, a recombinant DNA construct can be formed in part by operably linking at least one of the promoters of the present invention to any heterologous nucleotide sequence. The heterologous nucleotide sequence can be expressed in a cell as either a functional RNA or a polypeptide. The cell for expression includes a plant or bacterial cell, preferably a plant cell. The recombinant DNA construct preferably includes the SC194 promoter. The recombinant DNA construct preferably includes a heterologous nucleotide sequence that encodes a protein that plays a role in flower color formation, fragrance production, or shape/morphology development of the flower. The color of a flower can be altered transgenically by expressing genes involved in betalain, carotenoid, or flavanoid biosynthesis. In regard to genes involved in the biosynthesis of anthocyanin, dyhydroflavonol 4-reductase, flavonoid 3,5-hydroxylase, chalcone synthase, chalcone isomerase, flavonoid 3-hydroxylase, anthocyanin synthase, and UDP-glucose 3-O-flavonoid glucosyl transferase are some examples. The scent of a flower can be altered transgenically by expressing genes that manipulate the biosynthesis of fragrant fatty acid derivatives such as terpenoids, phenylpropanoids, and benzenoids in flowers. Some embodiments of the invention include a heterologous nucleotide sequence that is selected from S-linalool synthase, acetyl CoA:benzylalcohol acetyltransferase, benzyl CoA:benzylalcohol benzoyl transferase, S-adenosyl-L-methionine:benzoic acid carboxyl methyl transferase, mycrene synthases, (E)-β-ocimene synthase, orcinol O-methyltransferase, or limonene synthases. Flower structures/morphologies can be altered transgenically by expressing flower homeotic genes to create novel ornamental varieties. Some embodiments of the invention include a heterologous nucleotide sequence that is selected from genes such as, for example, AGAMOUS, APETALA3, and PISTILLATA.

It is recognized that the instant promoters may be used with their native coding sequences to increase or decrease expression in flower tissue. The selection of the heterologous nucleic acid fragment depends upon the desired application or phenotype to be achieved. The various nucleic acid sequences can be manipulated so as to provide for the nucleic acid sequences in the proper orientation.

Plasmid vectors comprising the instant recombinant DNA construct can be constructed. The choice of plasmid vector is dependent upon the method that will be used to transform host cells. The skilled artisan is well aware of the genetic elements that must be present on the plasmid vector in order to successfully transform, select and propagate host cells containing the recombinant DNA construct.

The described polynucleotide embodiments encompass isolated or substantially purified nucleic acid compositions. An "isolated" or "purified" nucleic acid molecule, or biologically active portion thereof, is substantially free of other cellular material or culture medium when produced by recombinant techniques, or substantially free of chemical precursors or other chemicals when chemically synthesized. An "isolated" nucleic acid is essentially free of sequences (preferably protein encoding sequences) that naturally flank the polynucleotide (i.e., sequences located at the 5' and 3' ends of the nucleic acid) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequences that naturally flank the polynucleotide in genomic DNA of the cell from which the polynucleotide is derived.

In another embodiment, the present invention includes host cells comprising either the recombinant DNA constructs or isolated polynucleotides of the present invention. Examples of the host cells of the present invention include, and are not limited to, yeast, bacteria, and plants, including flower crops such as, e.g., rose, carnation, Gerbera, Chrysanthemum, tulip, Gladioli, Alstroemeria, Anthurium, lisianthus, larkspur, irises, orchid, snapdragon, African violet, or azalea. Preferably, the host cells are plant cells, and more preferably, flower crop cells, and more preferably, Gerbera, rose, carnation, Chrysanthemum, or tulip cells.

Methods for transforming dicots, primarily by use of Agrobacterium tumefaciens, and obtaining transgenic plants have been published, among others, for cotton (U.S. Pat. No. 5,004,863, U.S. Pat. No. 5,159,135); soybean (U.S. Pat. No. 5,569,834, U.S. Pat. No. 5,416,011); Brassica (U.S. Pat. No. 5,463,174); peanut (Cheng et al., Plant Cell Rep. 15:653-657 (1996); McKently et al., Plant Cell Rep. 14:699-703 (1995)); papaya (Ling et al., Bio/technology 9:752-758 (1991)); and pea (Grant et al., Plant Cell Rep. 15:254-258 (1995)). For a review of other commonly used methods of plant transformation see Newell, C. A., Mol. Biotechnol. 16:53-65 (2000). One of these methods of transformation uses Agrobacterium rhizogenes (Tepfler, M. and Casse-Delbart, F., Microbiol. Sci. 4:24-28 (1987)). Transformation of soybeans using direct delivery of DNA has been published using PEG fusion (WO 92/17598), electroporation (Chowrira et al., Mol. Biotechnol. 3:17-23 (1995); Christou et al., Proc. Natl. Acad. Sci. U.S.A. 84:3962-3966 (1987)), microinjection (Neuhaus et al., Physiol. Plant. 79:213-217 (1990)), or particle bombardment (McCabe et al., Biotechnology 6:923 (1988); Christou et al., Plant Physiol. 87:671-674 (1988)).

In another embodiment, the present invention includes transgenic plants comprising the recombinant DNA constructs provided herein. The transgenic plants are selected from, for example, one of a number of various flower crops including roses, carnations, Gerberas, Chrysanthemums, tulips, Gladiolis, Alstroemerias, Anthuriums, lisianthuses, larkspurs, irises, orchids, snapdragons, African violets, azaleas, in addition to other less popular flower crops.

In some embodiments of the invention, there are provided transgenic seeds produced by the transgenic plants provided. Such seeds are able to produce another generation of transgenic plants.

There are a variety of methods for the regeneration of plants from plant tissues. The particular method of regeneration will depend on the starting plant tissue and the particular plant species to be regenerated. The regeneration, development and cultivation of plants from single plant protoplast transformants or from various transformed explants is well known in the art (Weissbach and Weissbach, Eds.; In Methods for Plant Molecular Biology; Academic Press, Inc.: San Diego, Calif., 1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

In addition to the above discussed procedures, there are generally available standard resource materials that describe specific conditions and procedures for the construction, manipulation and isolation of macromolecules (e.g., DNA molecules, plasmids, and the like), generation of recombinant DNA fragments and recombinant expression constructs, and the screening and isolating of clones (see, for example, Sambrook et al., 1989; Maliga et al., In Methods in Plant Molecular Biology; Cold Spring Harbor Press, 1995; Birren et al., In Genome Analysis: Detecting Genes, 1; Cold Spring Harbor: New York, 1998; Birren et al., In Genome Analysis: Analyzing DNA, 2; Cold Spring Harbor: New York, 1998; Clark, Ed., In Plant Molecular Biology: A Laboratory Manual; Springer: New York, 1997).

The skilled artisan will also recognize that different independent transformation events will result in different levels and patterns of expression of the chimeric genes (Jones et al., EMBO J. 4:2411-2418 (1985); De Almeida et al., Mol. Gen. Genetics 218:78-86 (1989)). Thus, multiple events must be screened in order to obtain lines displaying the desired expression level and pattern. Such screening may be accomplished by northern analysis of mRNA expression, western analysis of protein expression, or phenotypic analysis. Also of interest are seeds obtained from transformed plants displaying the desired expression profile.

The level of activity of the SC194 promoter in flowers is in some cases, comparable to that of many known strong promoters such as the CaMV 35S promoter (Atanassova et al., Plant Mol. Biol. 37:275-285 (1998); Battraw and Hall, Plant Mol. Biol. 15:527-538 (1990); Holtorf et al., Plant Mol. Biol. 29:637-646 (1995); Jefferson et al., EMBO J. 6:3901-3907 (1987); Wilmink et al., Plant Mol. Biol. 28:949-955 (1995)), the Arabidopsis oleosin promoters (Plant et al., Plant Mol. Biol. 25:193-205 (1994); Li, Texas A&M University Ph.D. dissertation, pp. 107-128 (1997)), the Arabidopsis ubiquitin extension protein promoters (Callis et al., J. Biol. Chem. 265(21):12486-12493 (1990)), a tomato ubiquitin gene promoter (Rollfinke et al., Gene 211:267-276 (1998)), a soybean heat shock protein promoter (Raschke et al., J. Mol. Biol. 199(4):549-557 (1988)), and a maize H3 histone gene promoter (Atanassova et al., Plant Mol. Biol. 37:275-285 (1998)).

In some embodiments, the promoters of the present invention are useful when flower-specific expression of a target heterologous nucleic acid fragment is required. Another useful feature of the promoters is its expression profile having high levels in developing flowers and low levels in young developing seeds (See Example 1). The promoters of the present invention are most active in developing flower buds and open flowers, while still having activity although approximately ten times lower in developing seeds. Thus, the promoters can be used for gene expression or gene silencing in flowers, especially when gene expression or gene silencing is desired predominantly in flowers along with a lower degree in developing seeds.

In some embodiments, the promoters of the present invention are used to construct recombinant DNA constructs that can be used to reduce expression of at least one heterologous nucleic acid sequence in a plant cell. To accomplish this, a recombinant DNA construct can be constructed by linking the heterologous nucleic acid sequence to a promoter of the present invention. (See, e.g., U.S. Pat. No. 5,231,020, WO99/53050, WO02/00904, and WO98/36083 for methodology to block plant gene expression via cosuppression.) Alternatively, recombinant DNA constructs designed to express antisense RNA for a heterologous nucleic acid fragment can be constructed by linking the fragment in reverse orientation to a promoter of the present invention. (See, e.g., U.S. Pat. No. 5,107,065 for methodology to block plant gene expression via antisense RNA.) Either the cosuppression or antisense chimeric gene can be introduced into plants via transformation. Transformants, wherein expression of the heterologous nucleic acid sequence is decreased or eliminated, are then selected.

There are embodiments of the present invention that include promoters of the present invention being utilized for methods of altering (increasing or decreasing) the expression of at least one heterologous nucleic acid sequence in a plant cell which comprises: transforming a plant cell with a recombinant DNA expression construct described herein; growing fertile mature plants from the transformed plant cell; and selecting plants containing a transformed plant cell wherein the expression of the heterologous nucleotide sequence is altered (increased or decreased).

Transformation and selection can be accomplished using methods well-known to those skilled in the art including, but not limited to, the methods described herein.

There are provided some embodiments that include methods of expressing a coding sequence in a plant that is a flower crop comprising: introducing a recombinant DNA construct disclosed herein into the plant; growing the plant; and selecting a plant displaying expression of the coding sequence; wherein the nucleotide sequence comprises: a nucleotide sequence comprising the sequence set forth in SEQ ID NO:1 or a full-length complement thereof; a nucleotide sequence comprising a fragment of the sequence set forth in SEQ ID NO:1, SEQ ID NO:2, SEQ ID NO:3, SEQ ID NO:4, SEQ ID NO:5, SEQ ID NO:6, or SEQ ID NO:7, or a full-length complement thereof, or in alternative embodiments, the sequence set forth in SEQ ID NO:2, SEQ ID NO:3, SEQ ID NO:4, SEQ ID NO:5, SEQ ID NO:6, or SEQ ID NO:7; or a nucleotide sequence comprising a sequence having at least 90% sequence identity, based on the BLASTN method of alignment, when compared to the sequence set forth in SEQ ID NO:1; wherein said nucleotide sequence initiates transcription in a flower cell of the plant.

Furthermore, some embodiments of the present invention include methods of transgenically altering a marketable flower trait of a flowering plant, comprising: introducing a recombinant DNA construct disclosed herein into the flowering plant; growing a fertile, mature flowering plant resulting from the introducing step; and selecting a flowering plant expressing the heterologous nucleotide sequence in flower tissue based on the altered marketable flower trait.

As further described in the Examples below, the promoter activity of the soybean genomic DNA fragment sequence SEQ ID NO:1 upstream of the SC194 protein coding sequence was assessed by linking the fragment to a yellow fluorescence reporter gene, ZS-YELLOW1 N1 (YFP) (Matz et al., Nat. Biotechnol. 17:969-973 (1999)), transforming the promoter::YFP expression cassette into soybean, and analyzing YFP expression in various cell types of the transgenic plants (see Example 7 and 8). All parts of the transgenic plants were analyzed and YFP expression was predominantly detected in flowers. These results indicated that the nucleic acid fragment contained flower-preferred promoter.

Some embodiments of the present invention provide recombinant DNA constructs comprising at least one isopentenyl transferase nucleic acid sequence operably linked to a provide promoter, preferably a SC194 promoter. The isopentenyl transferase plays a key step in the biosynthesis of plant cytokinin (Kakimoto, J. Plant Res. 116:233-239 (2003)). Elevated levels of cytokinin in plant cells might help to delay floral senescence and abortion which may present a potential way to improve crop yields (Chang et al., Plant Physiol. 132:2174-2183 (2003); Young et al., Plant J. 38:910-922 (2004)).

Utilities for Flower-Specific Promoters

The color, scent or morphology of a flower represents marketable flower traits, or characteristics/phenotypes of a flower that consumers, particularly floriculturalists, consider when determining which flowers are desirable and will be purchased. Hence, it would be beneficial to be able to alter these characteristics in order to satisfy the desires of consumers. Transgenic technologies can be implemented in order to achieve such results.

The phenotype of a flower can be altered transgenically by expressing genes, preferably in flower tissue, that play a role in color formation, fragrance production, or shape/morphology development of the flower. This type of alteration is particularly useful in the floriculture industry, and particularly useful for flowering plants.

The color of a flower is mainly the result of three types of pigment: flavanoids, carotenoids, and betalains. The flavanoids are the most common of the three and they contribute to colors ranging from yellow to red to blue, with anthocyanins being the major flavanoid. Carotenoids are C-40 tetraterpenoids that contribute to the majority of yellow hues and contribute to orange/red, bronze and brown colors, e.g., that seen in roses and chrysanthemums. Betalains are the least abundant and contribute to various hues of ivory, yellow, orange, red and violet. The color of a flower can be altered transgenically by expressing genes involved in, e.g., betalain, carotenoid, or flavanoid biosynthesis. In one example, the color of a flower can be altered transgenically by expressing genes involved in the biosynthesis of anthocyanin, for example, dyhydroflavonol 4-reductase, flavonoid 3,5-hydroxylase, chalcone synthase, chalcone isomerase, flavonoid 3-hydroxylase, anthocyanin synthase, and UDP-glucose 3-O-flavonoid glucosyl transferase. In some aspects of the invention, the gene involved in anthocyanin biosynthesis is the flavonoid 3,5-hydroxylase gene (see, e.g., Mori et al., supra). This type of alteration is particularly useful in the floriculture industry, providing novel flower colors in flower crops.

In addition to color, the scent of a flower can be altered transgenically by expressing genes that manipulate the biosynthesis of fragrant fatty acid derivatives such as terpenoids, phenylpropanoids, and benzenoids in flowers (see, e.g., Tanaka et al., supra). Genes involved in the biosynthesis of fragrant fatty acid derivatives can be operably linked to the flower-specific promoters presently described for preferential expression in flower tissue. The preferential expression in flower tissue can be utilized to generate new and desirable fragrances to enhance the demand for the underlying cut flower. A number of known genes that are involved in the biosynthesis of floral scents are described below. A strong sweet scent can be generated in a flower by introducing or upregulating expression of S-linalool synthase, which was earlier isolated from Clarkia breweri. Two genes that are responsible for the production of benzylacetate and benzylbenzoate are acetyl CoA:benzylalcohol acetyltransferase and benzyl CoA:benzylalcohol benzoyl transferase, respectively. These transferases were also reported to have been isolated from C. breweri. A phenylpropanoid floral scent, methylbenzoate, is synthesized in part by S-adenosyl-L-methionine: benzoic acid carboxyl methyl transferase (BAMT), which catalyzes the final step in the biosynthesis of methyl benzoate. BAMT is known to have a significant role in the emission of methyl benzoate in snapdragon flowers. Two monoterpenes, mycrene and (E)-β-ocimene, from snapdragon are known to be synthesized in part by the terpene synthases: mycrene synthases and (E)-β-ocimene synthases. Other genes involved in biosynthesis of floral scents have been reported and are being newly discovered, many of which are isolated from rose. Some genes involved in scent production in the rose include orcinol O-methyltransferase, for synthesis of S-adenosylmethionine, and limonene synthases (see, e.g., Tanaka et al., supra).

Flower structures/morphologies can be altered transgenically by expressing flower homeotic genes to create novel ornamental varieties. The flower homeotic genes that are determinative of flower morphology include genes such as AGAMOUS, APETALA3, PISTILLATA, and others that are known and/or are being elucidated (see, e.g., Espinosa-Soto et al., supra).

EXAMPLES

Aspects of the present invention are exemplified in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

In the discussion below, parts and percentages are by weight and degrees are Celsius, unless otherwise stated. Sequences of promoters, cDNA, adaptors, and primers listed herein are in the 5' to 3' orientation unless described otherwise. Techniques in molecular biology were typically performed as described in Ausubel et al., 1990 or Sambrook et al., 1989.

Example 1

Lynx MPSS Profiling of Soybean Genes Preferably Expressed in Flowers

Soybean expression sequence tags (ESTs) were generated by sequencing randomly selected clones from cDNA libraries constructed from different soybean tissues. Multiple EST sequences may have different lengths representing different regions of the same soybean gene. For those EST sequences representing the same gene that are found more frequently in a flower-specific cDNA library, there is a possibility that the representative gene could be a flower preferred gene candidate. Multiple EST sequences representing the same soybean gene were compiled electronically based on their overlapping sequence homology into a full length sequence representing a unique gene. These assembled, unique gene sequences were cumulatively collected and the information was stored in a searchable database. Flower specific candidate genes were identified by searching this database to find gene sequences that are frequently found in flower libraries but are rarely found in other tissue libraries, or not found in other tissue libraries.

One unique gene, PSO375649, was identified in the search as a flower specific gene candidate since all of the ESTs representing PSO375649 were found only in flower tissue. PSO375649 cDNA sequence (SEQ ID NO:19) as well as its putative translated protein sequence (SEQ ID NO:20) were used to search National Center for Biotechnology Information (NCBI) databases. PSO375649 was found to represent a novel soybean gene without significant homology to any known gene. PSO375649 was subsequently named after its genomic DNA clone lab name SC194.

A more sensitive gene expression profiling methodology MPSS (Mass Parallel Signature Sequence) transcript profiling technique (Brenner et al., Proc. Natl. Acad. Sci. USA 97:1665-70 (2000)) was used to confirm PSO375649 as a flower specific gene. The MPSS technology involves the generation of 17 base signature tags from mRNA samples that have been reverse transcribed from poly A+ RNA isolated using standard molecular biology techniques (Sambrook et al., 1989). The tags are simultaneously sequenced and assigned to genes or ESTs. The abundance of these tags is given a number value that is normalized to parts per million (PPM) which then allows the tag expression, or tag abundance, to be compared across different tissues. Genome wide gene expressions can be profiled simultaneously using this technology. Since each 17 base tag is long enough to be specific to only one or a few genes in any genome, the MPSS platform can be used to determine the expression pattern of a particular gene and its expression levels in different tissues.

MPSS gene expression profiles were generated from different soybean tissues over time, and the profiles were accumulated in a searchable database. PSO375649 cDNA sequence SEQ ID NO:19 was used to search the MPSS database to identify a MPSS tag sequence (SEQ ID NO:24) that is identical to a 17 base pair region from position 352 to 368 in the PSO375649 cDNA sequence. The identified MPSS tag was then used to search the MPSS database to reveal its abundance in different soybean tissues. As illustrated in Table 1, the PSO375649 gene was confirmed to be highly abundant in flowers and pods, a desired expression profile for its promoter to be able to express genes in flowers and in early developing pods.

TABLE 1

| Target Gene | PSO375649 |
|---|---|
| MPSS Tag Sequence | SEQ ID NO: 24 |
| Flower | 4818 |
| Pod | 61 |
| Flower Bud | 2759 |
| Lateral Root | 0 |
| Leaf | 0 |
| Petiole | 0 |
| Primary Root | 0 |
| Seed | 17 |
| Stem | 0 |

Example 2

Quantitative RT-PCR Profiles of SC194 Gene Expression in Soybean

The MPSS profiles of SC194 gene, PSO375649, was confirmed and extended by analyzing 14 different soybean tissues using the relative quantitative RT-PCR (qRT-PCR) technique with a 7500 real time PCR system (Applied Biosystems, Foster City, Calif.).

Fourteen soybean tissues (somatic embryo, somatic embryo grown one week on charcoal plate, leaf, leaf petiole, root, flower bud, open flower, R3 pod, R4 seed, R4 pod coat, R5 seed, R5 pod coat, R6 seed, R6 pod coat) were collected from cultivar 'Jack' and flash frozen in liquid nitrogen. The seed and pod development stages were defined according to descriptions in Fehr and Caviness, IWSRBC 80:1-12 (1977). Total RNA was extracted with Trizol reagents (Invitrogen, Carlsbad, Calif.) and treated with DNase I to remove any trace amount of genomic DNA contamination. The first strand cDNA was synthesized with Superscript III reverse transcriptase (Invitrogen).

PCR analysis was performed to confirm that the cDNA was free of genomic DNA. The forward and reverse primers used for PCR analysis are shown in SEQ ID NO:21 and SEQ ID NO:22, respectively The primers are specific to the 5'UTR intron/exon junction region of a soybean S-adenosylmethionine synthetase gene promoter (WO00/37662). PCR using this primer set amplifies a 967 bp DNA fragment from any soybean genomic DNA template and a 376 bp DNA fragment from the cDNA template. The genomic DNA-free cDNA aliquots were used in qRT-PCR analysis of PSO375649 using gene-specific primers SEQ ID NO:25 and SEQ ID NO:26. An endogenous soybean ATP sulfurylase gene was used as an internal control for normalization with primers SEQ ID NO:27 and SEQ ID NO:28 and soybean wild type genomic DNA was used as the calibrator for relative quantification.

The qRT-PCR profiling of the SC194 gene expression confirmed its predominant flower expression and also showed ongoing expression at levels more than ten fold lower during early pod and seed development (see FIG. 1).

Example 3

Isolation of Soybean SC194 Promoter

The soybean genomic DNA fragment corresponding to the SC194 promoter was isolated using a polymerase chain reaction (PCR) based approach called genome walking using the Universal GenomeWalker™ kit from Clontech™ (Product User Manual No. PT3042-1).

Soybean genomic DNA samples were digested, separately, to completion with four restriction enzymes DraI, EcoRV, HpaI, or PmlI, each of which generates DNA fragments having blunt ends. Double strand adaptors supplied in the GenomeWalker™ kit were added to the blunt ends of the genomic DNA fragments by DNA ligase. Two rounds of PCR were performed to amplify the SC194 corresponding genomic DNA fragment using two nested primers supplied in the Universal GenomeWalker™ kit that are specific to the adaptor sequence (AP1 and AP2, for the first and second adaptor primer, respectively), and two SC194 gene specific primers (GSP1 and GSP2) designed based on the 5' coding sequence of SC194 (PSO375649). The oligonucleotide sequences of the four primers are shown in SEQ ID NO:15 (GSP1), SEQ ID NO:16 (AP1), SEQ ID NO:17 (GSP2), and SEQ ID NO:18 (AP2). The GSP2 primer contains a recognition site for the restriction enzyme NcoI. The AP2 primer from the Universal GenomeWalker™ kit contains a SalI restriction site. The 3' end of the adaptor sequence SEQ ID NO:23 contains a XmaI recognition site downstream to the corresponding SalI restriction site in AP2 primer.

The AP1 and the GSP1 primers were used in the first round PCR using each of the adaptor ligated genomic DNA samples (DraI, EcoRV, HpaI or PmlI) under conditions defined in the GenomeWalker™ protocol. Cycle conditions were 94° C. for 4 minutes; 35 cycles of 94° C. for 30 seconds, 60° C. for 1 minute, and 68° C. for 3 minutes; and a final 68° C. for 5 minutes before holding at 4° C. One microliter from each of the first round PCR products was used as templates for the second round PCR with the AP2 and GSP2 primers. Cycle conditions for second round PCR were 94° C. for 4 minutes; 25 cycles of 94° C. for 30 seconds, 60° C. for 1 minute, and 68° C. for 3 minutes; and a final 68° C. for 5 minutes before holding at 4° C. Agarose gels were run to identify specific PCR product with an optimal fragment length. An approximately 1.3 Kb PCR product was detected and subsequently cloned into pCR2.1-TOPO vector by TOPO TA cloning (Invitrogen). Sequencing of the cloned PCR products revealed that its 3' end matched the 84 bp 5' end of the PSO375649 cDNA sequence, indicating that the PCR product was indeed the corresponding SC194 genomic DNA fragment. The 1358 bp genomic DNA sequence upstream of the putative SC194 start codon ATG is herein designated as soybean SC194 promoter (SEQ ID NO:1).

Example 4

SC194 Promoter Copy Number Analysis

Southern hybridization analysis was performed to determine whether there were other sequences in the soybean genome with high similarity to the SC194 promoter. Soybean 'Jack' wild type genomic DNA was digested with nine different restriction enzymes BamHI, BglII, DraI, EcoRI, EcoRV, HindIII, MfeI, NdeI, and SpeI, each separately, and distributed in a 0.7% agarose gel by electrophoresis. Each of the digested DNA samples was blotted onto a Nylon membrane and hybridized with digoxigenin (DIG) labeled SC194 promoter DNA probe according to the standard protocol (Roche Applied Science, Indianapolis, Ind.). The SC194 promoter probe was labeled by PCR using the DIG DNA labeling kit (Roche Applied Science) with two gene specific primers SEQ ID NO:12 and SEQ ID NO:8 to make a 685 bp probe described in SEQ ID NO:5 covering the 3' half of SC194 promoter sequence.

Since none of the above nine different restriction enzymes cuts inside the SC194 probe region as illustrated in FIG. 2B, a single band is expected to be hybridized by the SC194 probe in each of the lanes if there is only a single copy of the SC194 promoter sequence in soybean genome. A strong major band and a weak minor band were detected in each of eight digestion lanes, BamHI, BglII, DraI, EcoRI, EcoRV, HindIII, MfeI, and NdeI, suggesting that there is, in addition to the SC194 promoter sequence, another sequence with enough similarity to the SC194 promoter sequence to be hybridized though less effectively by the same SC194 probe (FIG. 2A). The fact that only one band was detected on the Southern blot of the SpeI digestion could be explained if two bands representing the SC194 promoter sequence and the other similar sequence, respectively, were similar in size to show as one overlapping band, or if the other similar sequence resulted in a band too small to be kept on the blot (any band smaller than 1 Kb would run out of the agarose gel under the experiment conditions).

Example 5

SC194:YFP Reporter Constructs and Soybean Transformation

The cloned SC194 promoter PCR fragment described in EXAMPLE 3 was digested with XmaI and NcoI, gel purified using a DNA gel extraction kit (Qiagen, Valencia, Calif.) and directionally cloned into the XmaI and NcoI site of a Gateway cloning ready vector QC299 (FIG. 3 and SEQ ID NO:40) containing a promoter-less fluorescent reporter gene ZS-YELLOW1 N1 (YFP) to make the reporter construct QC300 (SEQ ID NO:41) with the soybean SC194 promoter driving the YFP gene expression (FIG. 3). The SC194:YFP expression cassette in construct QC300 was linked to the SAMS:ALS (S-adenosyl methionine synthetase:acetolactate synthase) expression cassette in construct PHP25224 (FIG. 3 and SEQ ID NO:42) by Gateway cloning to create construct QC302 (FIG. 3 and SEQ ID NO:43). The linked SC194:YFP and SAMS:ALS cassettes were released as a 6431 bp DNA fragment from construct QC302 bp AscI restriction digestion, separated from the vector backbone fragment by agarose gel electrophoresis, and purified from the gel using a Qiagen DNA gel extraction kit. The purified DNA fragment was used to transform soybean cultivar Jack using the particle gun bombardment method (Klein et al., Nature 327:70-73 (1987); U.S. Pat. No. 4,945,050) to study the SC194 promoter activity in stably transformed soybean plants.

Soybean somatic embryos from the Jack cultivar were induced as follows. Cotyledons (smaller than 3 mm in length) were dissected from surface-sterilized, immature seeds and were cultured for 6-10 weeks under fluorescent light at 26° C. on a Murashige and Skoog media ("MS media") containing 0.7% agar and supplemented with 10 mg/ml 2,4-dichlorophenoxyacetic acid (2,4-D). Globular stage somatic embryos, which produced secondary embryos, were then excised and placed into flasks containing liquid MS medium supplemented with 2,4-D (10 mg/ml) and cultured in the light on a rotary shaker. After repeated selection for clusters of somatic embryos that multiplied as early, globular staged embryos, the soybean embryogenic suspension cultures were maintained in 35 ml liquid media on a rotary shaker, 150 rpm, at 26° C. with fluorescent lights on a 16:8 hour day/night schedule. Cultures were subcultured every two weeks by inoculating approximately 35 mg of tissue into 35 ml of the same fresh liquid MS medium.

Soybean embryogenic suspension cultures were then transformed by the method of particle gun bombardment using a DuPont Biolistic™ PDS1000/HE instrument (helium retrofit) (Bio-Rad Laboratories, Hercules, Calif.). To 50 µl of a 60 mg/ml 1.0 mm gold particle suspension were added (in order): 30 µl of 10 ng/µl SC194:YFP+SAMS:ALS DNA fragment, 20 µl of 0.1 M spermidine, and 25 µl of 5 M $CaCl_2$. The particle preparation was then agitated for 3 minutes, spun in a centrifuge for 10 seconds and the supernatant removed. The DNA-coated particles were then washed once in 400 µl 100% ethanol and resuspended in 45 µl of 100% ethanol. The DNA/particle suspension was sonicated three times for one second each. 5 µl of the DNA-coated gold particles was then loaded on each macro carrier disk.

Approximately 300-400 mg of a two-week-old suspension culture was placed in an empty 60×15 mm Petri dish and the residual liquid removed from the tissue with a pipette. For each transformation experiment, approximately 5 to 10 plates of tissue were bombarded. Membrane rupture pressure was set at 1100 psi and the chamber was evacuated to a vacuum of 28 inches mercury. The tissue was placed approximately 3.5 inches away from the retaining screen and bombarded once. Following bombardment, the tissue was divided in half and placed back into liquid media and cultured as described above.

Five to seven days post bombardment, the liquid media was exchanged with fresh media containing 100 ng/ml chlorsulfuron as selection agent. This selective media was refreshed weekly. Seven to eight weeks post bombardment, green, transformed tissue was observed growing from untransformed, necrotic embryogenic clusters. Isolated green tissue was removed and inoculated into individual flasks to generate new, clonally propagated, transformed embryogenic suspension cultures. Each clonally propagated culture was treated as an independent transformation event and subcultured in the same liquid MS media supplemented with 2,4-D (10 mg/ml) and 100 ng/ml chlorsulfuron selection agent to increase mass. The embryogenic suspension cultures were then transferred to solid agar MS media plates without 2,4-D supplement to allow somatic embryos to develop. A sample of each event was collected at this stage for PCR and quantitative PCR analysis.

Cotyledon stage somatic embryos were dried-down (by transferring them into an empty small Petri dish that was seated on top of a 10 cm Petri dish to allow slow dry down) to mimic the last stages of soybean seed development. Dried-down embryos were placed on germination solid media, and transgenic soybean plantlets were regenerated. The transgenic plants were then transferred to soil and maintained in growth chambers for seed production.

Genomic DNA was extracted from somatic embryo samples and analyzed by quantitative PCR using the 7500 real time PCR system (Applied Biosystems) with gene-specific primers and 6-carboxyfluorescein (FAM)-labeled fluorescence probes to check copy numbers of both the SAMS:ALS expression cassette and the SC194:YFP expression cassette. The qPCR analysis was done in duplex reactions with a heat shock protein (HSP) gene as the endogenous control and a transgenic DNA sample with a known single copy of SAMS:ALS or YFP transgene as the calibrator using the relative quantification methodology. The endogenous control HSP probe was labeled with VIC (Applera Corporation, Norwalk, Conn.) and the target gene SAMS or YFP probe was labeled with FAM for the simultaneous detection of both fluorescent probes in the same duplex reactions. The primers and probes used in the qPCR analysis are listed below.

SAMS forward primer: SEQ ID NO:29
FAM labeled SAMS probe: SEQ ID NO:30
SAMS reverse primer: SEQ ID NO:31
YFP forward primer: SEQ ID NO:32
FAM labeled YFP probe: SEQ ID NO:33
YFP reverse primer: SEQ ID NO:34
HSP forward primer: SEQ ID NO:35
VIC labeled HSP probe: SEQ ID NO:36
FAM labeled DNA oligo probes and VIC labeled oligo probes were obtained from Sigma Genosys (The Woodlands, Tex.).

Only transgenic soybean events containing 1 or 2 copies of both the SAMS:ALS expression cassette and the SC194:YFP expression cassette Were selected for further gene expression evaluation and seed production (see Table 2). Events negative for YFP qPCR or with more than 2 copies for the SAMS or YFP qPCR were terminated. YFP expression detection in flowers as described in EXAMPLE 8 is also recorded in the same table.

TABLE 2

| Event ID | SAMS qPCR | YFP qPCR | YFP Expression |
|---|---|---|---|
| 4775.1.1 | 1.30 | 1.16 | − |
| 4775.1.3 | 1.01 | 1.26 | − |
| 4775.3.1 | 1.24 | 1.33 | + |
| 4775.3.2 | 1.17 | 1.36 | − |
| 4775.3.3 | 1.79 | 1.38 | + |
| 4775.3.4 | 2.08 | 1.29 | + |
| 4775.4.1 | 1.18 | 1.43 | + |
| 4775.5.1 | 1.47 | 1.11 | + |
| 4775.6.2 | 0.93 | 1.06 | + |
| 4775.7.2 | 1.43 | 1.20 | + |
| 4775.1.4 | 1.31 | 1.39 | − |
| 4775.2.2 | 1.12 | 1.13 | + |
| 4775.3.5 | 1.28 | 1.89 | − |
| 4775.3.6 | 2.48 | 1.17 | + |
| 4775.3.7 | 1.30 | 1.21 | + |
| 4775.8.2 | 1.28 | 1.30 | + |
| 4775.2.3 | 2.33 | 1.91 | + |

Example 6

Construction of SC194 Promoter Deletion Constructs

To define the transcriptional elements controlling the SC194 promoter activity, six 5' unidirectional deletion fragments SEQ ID NO:2 of 1328 bp, SEQ ID NO:3 of 1134 bp, SEQ ID NO:4 of 932 bp, SEQ ID NO:5 of 685 bp, SEQ ID NO:6 of 472 bp, and SEQ ID NO:7 of 237 bp were made by utilizing PCR amplification and the full length soybean SC194 promoter contained in the original construct QC300 (FIG. 3) as DNA template. The same antisense primer (SEQ ID NO:8) was used in the amplification of the six SC194 promoter fragments by pairing with different sense primers SEQ ID NOs: 9, 10, 11, 12, 13, and 14 respectively, to produce the promoter fragments represented by SEQ ID NOs: 2, 3, 4, 5, 6, and 7.

Each of the PCR amplified promoter DNA fragments was cloned into the Gateway cloning ready TA cloning vector pCR8/GW/TOPO (Invitrogen, Carlsbad, Calif.; FIG. 4 and SEQ ID NO:44), and clones with the insert in correct orientation, relative to the Gateway recombination sites attL1 and attL2 in the pCR8/GW/TOPO vector, were selected by AflII restriction enzyme digestion analysis or sequence confirmation (see the example map QC300-1 (SEQ ID NO:45) in FIG. 4, which contains the 1328 SC194 promoter deletion fragment SEQ ID NO:2). The maps of constructs QC300-2, QC300-3, QC300-4, QC300-5, and QC300-6 containing the SC194 promoter deletion fragments SEQ ID NOs:3, 4, 5, 6, and 7 were similar. The promoter fragment in the right orientation was subsequently cloned into the Gateway destination vector QC330 (FIG. 4 and SEQ ID NO:46) by Gateway LR clonase reaction (Invitrogen) to place the promoter fragment in front of the reporter gene YFP (see the example map QC300-1Y (SEQ ID NO:47) in FIG. 4, which contains the 1328 SC194 promoter deletion fragment SEQ ID NO:2). A 21 bp Gateway recombination site attB2 (SEQ ID NO:39) was inserted between the promoter and the YFP reporter gene coding region as a result of the Gateway cloning process. Another 21 bp Gateway recombination site attB1 (SEQ ID NO:38) was left at the 5' end of the SC194 promoter. The maps of constructs QC300-2Y (SEQ ID NO:48), QC300-3Y (SEQ ID NO:49), QC300-4Y (SEQ ID NO:50), QC300-5Y (SEQ ID NO:51), and QC300-6Y (SEQ ID NO:52) containing the SC194 promoter deletion fragments SEQ ID NOs: 3, 4, 5, 6, and 7 were similar.

The SC194:YFP promoter deletion constructs QC300-1Y, QC300-2Y, QC300-3Y, QC300-4Y, QC300-5Y, and QC300-6Y were ready to be transformed into germinating soybean cotyledons by gene gun bombardment method for transient gene expression study. The 1358 bp full length SC194 promoter in construct QC300 was included as a positive control for transient expression analysis. A simple schematic description of the six SC194 promoter deletion fragments can be found in FIG. 5.

Example 7

Transient Expression Analysis of SC194:YFP Constructs

Full length SC194 promoter construct QC300 and its series deletion constructs QC300-1Y, 2Y, 3Y, 4Y, 5Y, and 6Y were tested by the YFP gene transient expression assay using germinating soybean cotyledons as the target tissue. Soybean seeds were rinsed with 10% Tween 20 in sterile water, surface-sterilized with 70% ethanol for 2 minutes and then by 6% sodium hypochloride for 15 minutes. After rinsing, the seeds were placed on wet filter paper in a Petri dish to germinate for 4-6 days under fluorescent light at 26° C. Green cotyledons were excised and placed inner side up on a 0.7% agar plate containing MS media for particle gun bombardment.

The DNA and gold particle mixtures were prepared similarly as described in EXAMPLE 5 except with more DNA (100 ng/μl). The bombardments were also carried out under similar parameters as described in EXAMPLE 5. YFP expression was checked under a Leica MZFLIII stereo microscope equipped with UV light source and appropriate light filters (Leica Microsystems Inc., Bannockburn, Ill.), and all microscopic pictures were taken under the same camera settings: 1.06 gamma, 0.0% gain, and 0.58 seconds exposure approximately 24 hours after bombardment with 8× magnification.

The full length SC194 promoter construct QC300 expressed YFP but much weaker than the positive control construct pZSL90 (SEQ ID NO:53), which contained a strong constitutive promoter SCP1 (U.S. Pat. No. 6,072,050), in transient expression assay as shown by the different size green dots (FIG. 6A, H). Each dot represented a single cotyledon cell which appeared larger if the fluorescence was strong or smaller if the fluorescence was weak, even under the same magnification. The QC300-1Y and QC300-2Y constructs containing, respectively, the 1328 bp and 1134 bp truncated SC194 promoter fragments and with the attB2 Gateway recombination site (Invitrogen) inserted between the SC194 promoter and the YFP had similar expression that also appeared to be weaker than the full length SC194 promoter (FIG. 6B, C). The 932 bp truncated SC194 promoter construct QC300-3Y (FIG. 6D) had obviously lower expression than the above three longer SC194 promoter constructs. Further truncations of the SC194 promoter to 685 bp in construct QC300-4Y and to 472 bp in construct QC300-5Y further reduced the promoter activity as indicated by the fewer and smaller fluorescence dots (FIG. 6E, F). But even when the SC194 promoter was truncated to the 237 bp minimal size in construct QC300-6Y, the promoter fragment still retained very low level activity with only a few faint green dots barely detectable (FIG. 6G).

Example 8

SC194:YFP Expression in Stable Transgenic Soybean Plants

YFP gene expression was checked at different stages of transgenic plant development for yellow fluorescence emission under a Leica MZFLIII stereo microscope equipped with UV light source and appropriate light filters (Leica Microsystems Inc., Bannockburn, Ill.). No specific yellow fluorescence was detected during somatic embryo development or in vegetative tissues such as leaf, petiole, stem, or root of the transgenic plants. Fluorescence was only detected in flowers.

A soybean flower consists of five sepals, five petals including one standard large upper petal, two large side petals, and two small fused lower petals called kneel to enclose ten stamens and one pistil. The filaments of the ten stamens fuse together to form a sheath to enclose the pistil and separate into 10 branches only at the top to each bear an anther. The pistil consists of a stigma, a style, and an ovary in which there are normally 2-4 ovules that will eventually develop into seeds.

Specific fluorescence signal (green color) was first detected at the junctions between anthers and filaments, and also in the distal part of petals in young flower bud when the petals were still completely enclosed by sepals (FIG. 7A). In older flower bud and open flower, fluorescence spread throughout all petals and the entire filaments but still concentrated at the anther and filament junctions (FIG. 7B, C, D). No specific fluorescence was detected in sepals or in flower pedicle, which displayed red auto fluorescence resulting from plant green tissues (FIG. 7A, C, D). Fluorescence was detected in the style but not in the ovary part of the pistil (FIG. 7F). It seemed that under higher magnification no YFP fluorescence was detectable in stigma or in pollen, though it is noted that auto fluorescence was strong in pollen (FIG. 7E, G). The yellow auto fluorescence in pollen was even stronger under a non-specific UV light filter, while YFP-specific greenish fluorescence disappeared under the same non-specific filter. When an open flower was dissected longitudinally to expose the inside of the ovary, no fluorescence was detected in the inside ovary wall or in any of the ovules (FIG. 7D). Similarly, no fluorescence was detected in any part of young or old developing pod or seeds (FIG. 7H).

In conclusion, the SC194:YFP expression was only detected in petals, filaments, style, and was strongest in the anther and filament junctions of a soybean flower. The expression was first detectable in young flower buds when the petals were still completely enclosed by sepals. No expression was detectable in other parts of the flower such ovary, stigma, or pollens or other tissues such as leaf, root, petiole, pod coat, or developing seeds of transgenic soybean plants.

Twelve out of 17 transgenic events expressed YFP in the same manner as described in details above (Table 2). The other five events contained the transgene as revealed by qPCR but failed to express YFP.

What is claimed is:

1. A recombinant DNA construct comprising a nucleotide sequence comprising the sequence set forth in SEQ ID NO:1 operably linked to at least one heterologous sequence, wherein said nucleotide sequence is a promoter.

2. The recombinant DNA construct of claim 1, wherein the heterologous nucleotide sequence encodes a gene involved in anthocyanin biosynthesis, a gene involved in the synthesis of fragrant fatty acid derivatives, a gene that is determinative of flower morphology, or a gene involved in biosynthesis of plant cytokinin.

3. The recombinant DNA construct of claim 2, wherein the gene involved in anthocyanin biosynthesis is dyhydroflavonol 4-reductase, flavonoid 3,5-hydroxylase, chalcone synthase, chalcone isomerase, flavonoid 3-hydroxylase, anthocyanin synthase, or UDP-glucose 3-O-flavonoid glucosyl transferase.

4. The recombinant DNA construct of claim 2, wherein the gene involved in the synthesis of fragrant fatty acid derivatives is S-linalool synthase, acetyl CoA:benzylalcohol acetyltransferase, benzyl CoA:benzylalcohol benzoyl transferase, S-adenosyl-L-methionine:benzoic acid carboxyl methyl transferase, mycrene synthase, (E)-β-ocimene synthase, orcinol O-methyltransferase, or limonene synthase.

5. The recombinant DNA construct of claim 2, wherein the gene that is determinative of flower morphology is AGAMOUS, APETALA, or PISTILLATA.

6. The recombinant DNA construct of claim 2, wherein the gene involved in biosynthesis of plant cytokinin is isopentenyl transferase.

7. A vector comprising the recombinant DNA construct of claim 1.

8. An isolated cell comprising the recombinant DNA construct of claim 1.

9. The cell of claim 8, wherein the cell is a plant cell.

10. A transgenic plant having stably incorporated into its genome the recombinant DNA construct of claim 1.

11. The transgenic plant of claim 10, wherein the plant is a flowering plant.

12. The transgenic plant of claim 11, wherein the flowering plant is rose, carnation, Gerbera, Chrysanthemum, tulip, Gladioli, Alstroemeria, Anthurium, lisianthus, larkspur, irises, orchid, snapdragon, African violet, or azalea.

13. A transgenic seed produced by the transgenic plant of claim 12, wherein the transgenic seed comprises the recombinant DNA construct.

14. A method of expressing a coding sequence or a functional RNA in a plant comprising:
   a) introducing the recombinant DNA construct of claim 1 into the plant, wherein the at least one heterologous sequence comprises a coding sequence or encodes a functional RNA;
   b) growing the plant of step a); and,
   c) selecting a plant displaying expression of the coding sequence or the functional RNA of the recombinant DNA construct.

15. A method of transgenically altering a marketable flower trait of a flowering plant, comprising:
   a) introducing a recombinant DNA construct of claim 1 into the plant;
   b) growing a fertile, mature plant resulting from step a); and
   c) selecting a plant expressing the at least one heterologous nucleotide sequence in at least one plant tissue based on the altered marketable trait.

16. The method of claim 15 wherein the marketable flower trait is color, morphology, or fragrance.

* * * * *